United States Patent
Klein et al.

(10) Patent No.: US 9,901,660 B2
(45) Date of Patent: Feb. 27, 2018

(54) LOW FRICTION HYDROGELS AND HYDROGEL-CONTAINING COMPOSITE MATERIALS

(71) Applicant: Yeda Research and Development Co. Ltd., Rehovot (IL)

(72) Inventors: Jacob Klein, Rehovot (IL); Ronit Goldberg, Rehovot (IL); Noa Iuster, Rehovot (IL); Raya Sorkin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 56 days.

(21) Appl. No.: 14/902,574

(22) PCT Filed: Jul. 3, 2014

(86) PCT No.: PCT/IL2014/050604
§ 371 (c)(1),
(2) Date: Jan. 3, 2016

(87) PCT Pub. No.: WO2015/001564
PCT Pub. Date: Jan. 8, 2015

(65) Prior Publication Data
US 2016/0175488 A1    Jun. 23, 2016

Related U.S. Application Data

(60) Provisional application No. 61/842,995, filed on Jul. 4, 2013.

(51) Int. Cl.
*A61K 9/127* (2006.01)
*A61L 27/52* (2006.01)
(Continued)

(52) U.S. Cl.
CPC ............ *A61L 27/52* (2013.01); *A61K 9/0019* (2013.01); *A61K 9/0024* (2013.01); *A61L 27/34* (2013.01);
(Continued)

(58) Field of Classification Search
None
See application file for complete search history.

(56) References Cited

U.S. PATENT DOCUMENTS 6,048,546 A * 4/2000 Sasaki ................. A61K 9/1272
264/4.1
2006/0270781 A1* 11/2006 Ruberti ................. A61F 2/442
524/503
(Continued)

FOREIGN PATENT DOCUMENTS

WO    WO 01/15750    3/2001
WO    WO 2008/018796    2/2008
(Continued)

OTHER PUBLICATIONS

The effect of added liposomes on the rheological properties of a hydrogel, Mourtas et al. 2007, p. 611-619, Journal of Colloid and interface science, 317, 2008.*
(Continued)

*Primary Examiner* — Peter A Salamon

(57) ABSTRACT

Hydrogels and composite material containing hydrogels and liposomes dispersed therein, which exhibit a reduced friction coefficient compared to neat hydrogels or composites containing hydrogels, processes for preparing the same, and methods for using the same are disclosed.

29 Claims, 25 Drawing Sheets

(51) Int. Cl.
| | |
|---|---|
| A61L 27/34 | (2006.01) |
| A61K 9/00 | (2006.01) |
| C09D 133/06 | (2006.01) |
| A61L 27/44 | (2006.01) |
| C08F 2/10 | (2006.01) |
| C08F 2/44 | (2006.01) |

(52) U.S. Cl.
CPC ............... *A61L 27/44* (2013.01); *C08F 2/10* (2013.01); *C08F 2/44* (2013.01); *C09D 133/066* (2013.01); *A61L 2300/626* (2013.01); *A61L 2400/10* (2013.01); *A61L 2430/06* (2013.01); *A61L 2430/10* (2013.01); *A61L 2430/24* (2013.01); *A61L 2430/38* (2013.01)

(56) References Cited

U.S. PATENT DOCUMENTS

| | | | | |
|---|---|---|---|---|
| 2010/0098749 | A1* | 4/2010 | Barenholz | A61K 9/0019 424/450 |
| 2010/0226985 | A1* | 9/2010 | Van Tomme | A61K 9/0024 424/486 |
| 2012/0282324 | A1* | 11/2012 | Xing | A61K 38/1825 424/450 |

FOREIGN PATENT DOCUMENTS

| | | |
|---|---|---|
| WO | WO 2008/038292 | 4/2008 |
| WO | WO 2015/001564 | 1/2015 |

OTHER PUBLICATIONS

Dispersion of DMPC liposomes in contact lenses for ophthalmic drug delivery, Gulsen et al., Sep. 2005, Current Eye Research, 30, 1070-1080.*
Carbopol Polymer Products, Lubrizol Corp, downloaded Jul. 24, 2017, 3 pages.*
International Search Report and the Written Opinion dated Oct. 2, 2014 From the International Searching Authority Re. Application No. PCT/IL2014/050604.
Bavaresco et al. "Study on the Tribological Properties of pHEMA Hydrogels for Use in Artificial Articular Cartilage", Wear, 265: 269-277, 2008.
Brochu "Physico-Chemical Characterization of Layers of Intact Liposomes for Drug Release Applications", Thesis for Obtaining the Diploma for Doctor of Philosophy in Chemical Engineering (Ph.D.), Universite de Sherbrooke, Faculte de Genie, Departement de Genie Chimique, Sherbrooke, Quebec, Canada, 113 P., Feb. 2008.
Cascone et al. "Poly(Vinyl Alcohol) Hydrogels as Hydrophilic Matrices for the Release of Lipophilic Drugs Loaded in PLGA Nanoparticles", Journal of Materials Science: Materials in Medicine, 13: 29-32, 2002.
DiTizio et al. "A Liposomal Hydrogel for the Prevention of Bacterial Adhesion to Catheters", Biomaterials, 19: 1877-1884, 1998.
Dragicevic-Curic et al. "Temoprofin-Loaded Liposomal Gels: Viscoelastic Properties and in Vitro Skin Penetration", International Journal of Pharmaceutics, 373: 77-84, 2009.
Forge et al. "Morphology of Egg Phosphatidylcholine-Cholesterol Single-Bilayer Vesicles, Studied by Freeze-Etch Electron Microscopy", Journal of Membrane Biology, 41: 249-263, 1978.
Freeman et al. "Friction, Wear, and Lubrication of Hydrogels as Synthetic Articular Cartilage", Wear, 241: 129-135, 2000.
Gong "Friction and Lubrication of Hydrogels—Its Richness and Complexity", Soft Matter, 2: 544-552, 2006.
Gulsen et al. "Dispersion of DMPC Liposomes in Contact Lenses for Ophthalmic Drug Delivery", Current Eye Research, 30: 1071-1080, 2005.
Hosny "Ciprofloxacin as Ocular Liposomal Hydrogel", AAPS PharmSciTech, 11(1): 241-246, Mar. 2010.
Hosny "Optimization of Gatifloxacin Liposomal Hydrogel for Enhanced Transcorneal Permeation", Journal of Liposome Research, 20(1): 31-37, 2010.
Hosny "Preparation and Evaluation of Thermosensitive Liposomal Hydrogel for Enhanced Transcorneal Permeation of Ofloxacin", AAPS PharmSciTech, 10(4): 1336-1342, Dec. 2009.
Ishikawa et al. "Lubrication Properties of Hydrogel-Coated Polyethylene Head", Materials Transactions, 45(4): 1041-1044, 2004.
Kang et al. "A New Vaginal Delivery System of Amphotericin B: A Dispersion of Cationic Liposomes in a Thermosensitive Gel", Journal of Drug Targeting, 18(8): 637-644, 2010.
Lajavardi et al. "New Formulation of Vasoactive Intestinal Peptide Using Liposomes in Hyaluronic Acid Gel for Uveitis", Journal of Controlled Release, 139: 22-30, 2009.
Lim et al. "Microencapsulated Islets as Bioartificial Endocrine Pancreas", Science, 210: 908-910, Nov. 21, 1980.
Liu et al. "Behaviors of Liposomes in a Thermo-Responsive Poly(N- Isopropylacrylamide) Hydrogel", Soft Matter, 8: 4517-4523, 2012.
Mahoney et al. "Three-Dimensional Growth and Function of Neural Tissue in Degradable Polyethylene Glycol Hydrogels", Biomaterials, 27: 2265-2274, 2006.
Mourtas et al. "Complex Hydrogel Systems Composed of Polymers, Liposomes, and Cyclodextrins: Implications of Composition on Rheological Properties and Aging", Langmuir, 25(15): 8480-8488, 2009.
Mourtas et al. "Liposomal Drugs Dispersed in Hydrogels. Effect of Liposome, Drug and Gel Properties on Drug Release Kinetics", Colloids and Surfaces B: Biointerfaces, 55: 212-221, 2007.
Mourtas et al. "The Effect of Added Liposomes on the Rheological Properties of a Hydrogel: A Systematic Study", Journal of Colloid and Interface Science, 317(2): 611-619, Epub Sep. 29, 2007. Abstract, Supporting Information.
Moutos et al. "A Biomemetic Three-Dimensional Woven Composite Scaffold for Functional Tissue Engineering of Cartilage", Nature Materials, 6(2): 162-167, Feb. 2007.
Nagarsenker et al. "Preparation and Evaluation of Liposomal Formulations of Tropicamide for Ocular Delivery", International Journal of Pharmaceutics, 190: 63-71, 1999.
Ortan et al. "Rheological Study of a Liposomal Hydrogel Based on Carbopol", Romanian Biotechnological Letters, 16(1/Suppl.): 47-54, 2011.
Pavelic et al. "Liposomal Gels for Vaginal Drug Delivery", International Journal of Pharmaceutics, 219: 139-149, 2001.
Petrtyl et al. "The Initial Bearing Capacities of Subchondral Bone Replacements Considerably Contributing to Chondrogenesis", Acta of Bioengineering and Biomechanics, 12(3): 59-65, 2010.
Ruvinov et al. "The Promotion of Myocardial Repair by the Sequential Delivery of IGF-1 and HGF From an Injectable Alginate Biomaterial in a Model of Acute Myocardial Infarction", Biomaterials, 32: 565-578, 2011.
Serafim et al. "New Hydrogels Based on Gelatin and Acrylamide", U.P.B. Scientific Bulletin, Series B: Chemistry and Materials Science, 75(2): 3-14, 2013.
Shailesh et al. "Development and Evaluation of Muprirocin Loaded Liposomal Hydrogels for Diabetic Wound Healing Properties", Indian Journal of Advances in Chemical Science, 2: 42-45, 2014.
Soni et al. "Experimental Design and Optimization Studies of the Thermoreversible Hydrogel Containing Liposomes for the Controlled Delivery of 5-Fluorouracil", Pharmagene, 1(3): 24-32, 2013.
Szoka Jr. et al. "Comparative Properties and Methods of Preparation of Lipid Vesicles (Liposomes)", Annual Review of Biophysics and Bioengineering, 9: 467-508, 1980.
Ullrich et al. "Encapsulation Stability and Temperature-Dependent Release Kinetics From Hydrogel-Immobilised Liposomes", Journal of Colloid and Interface Science, 394: 380-385, 2013.
Van den Bulcke et al. "Structural and Rheological Properties of Methacrylamide Modified Gelatin Hydrogels", Biomacromolecules, 1:31-38, 2000.
Vecchio et al. "Surfactant Treatment for Osteoarthritis", Rheumatology, 38(10): 1020-1021, Oct. 1999.

(56) References Cited

OTHER PUBLICATIONS

Winterhalter et al. "Liposome Stability and Formation: Experimental Parameters and Theories on the Size Distribution", Chemistry and Physics of Lipids, 64: 35-43, 1993.
Zhou et al. "Studies of Phospholipid Hydration by High-Resolution Magic-Angle Spinning Nuclear Magnetic Resonance", Biophysical Journal, 76: 387-399, Jan. 1999.
Supplementary European Search Report and the European Search Opinion dated Jan. 17, 2017 From the European Patent Office Re. Application No. 14819627.2. (9 Pages).
DiRamio et al. "Poly(Ethylene Glycol) Methacrylate/ Dimethacrylate Hydrogels for Controlled Release of Hydrophobic Drugs", Biotechnology Progess, XP055332866, 21(4): 1281-1288, Published on Web Apr. 28, 2005. p. 1282.
DiTizio et al. "A Liposomal Hydrogel for the Prevention of Bacterial Adhesion to Catheters", Biomaterials, XP004161461, 19(20): 1877-1884, Oct. 1998. Points 2.1, 2.2, .2.3.
Karpushkin et al. "Rheological Properties of Homogeneous and Heterogeneous Poly(2-Hydroxyethyl Methacrylate) Hydrogels", Polymer International, XP055332857, 61(2): 328-336, Published Online Oct. 14, 2011. Fig.8.
Trunfio-Sfarghiu et al. "Multiscale Analysis of the Tribological Role of the Molecular Assemblies of Synovial fluid. Case of a Healthy Joint and Implants", Tribbology International, XP022218079, 40(10-12): 1500-1515, Available Online Apr. 6, 2007. Points 2.1.1, 2.2.1, 3.3.1.1, 3.3.1.3, Table 1, Fig.3.
Verberne et al. "Liposomes as Potential Biolubricant Additives for Wear Reduction in Human Synovial Joints", Wear, XP026924037, 268(7-8): 1037-1042, Available Online Dec. 28, 2009. Points 2.2, 3.1, 3.3, Table 1.

\* cited by examiner

Shear traces of HEMA EGDMA 1% in pure water

Shear traces of symmetric HEMA + MLV HSPC liposome hydrogels

LOW FRICTION HYDROGELS AND HYDROGEL-CONTAINING COMPOSITE MATERIALS

RELATED APPLICATIONS

This application is a National Phase of PCT Patent Application No. PCT/IL2014/050604 having International filing date of Jul. 3, 2014, which claims the benefit of priority under 35 USC § 119(e) of U.S. Provisional Patent Application No. 61/842,995 filed on Jul. 4, 2013. The contents of the above applications are all incorporated by reference as if fully set forth herein in their entirety.

FIELD AND BACKGROUND OF THE INVENTION

The present invention, in some embodiments thereof, relates to material science, and more particularly, but not exclusively, to compositions and methods for reducing the friction coefficient of hydrogels or of composite materials comprising a hydrogel, and to uses of such low friction hydrogels or composite materials containing same.

Lubrication in aqueous media presents a critical challenge in modern material science. Lubrication in aqueous and biological media is often problematic as water on its own is not a good lubricant, while surfaces or surface coatings in water frequently exhibit quite high friction coefficients, higher than 0.08, especially at high loads/pressures. The problem is more evident when extremely low friction is required, particularly at high pressures of up to 100 atmospheres or more, and at low sliding velocities.

Various attempts to provide low friction conditions in aqueous media, and particularly under physiological conditions for treating, inter alia, joint dysfunction, have been made.

Vecchio et al. [Rheumatology (Oxford), 1999, 38(10), pp. 1020-1021] describe the injection of dipalmitoylphosphatidylcholine (DPPC) lipid surfactant solutions in propylene glycol into joints in an attempt to provide a treatment for osteoarthritis.

U.S. Pat. No. 6,800,298 describes a lubricating composition (i.e. a lubricant) comprising dextran-based hydrogel with lipids.

Liposomes are vesicles whose membranes in most cases are based on phospholipid bilayers. They are generally biocompatible and, when modified with other molecules, are widely used in clinical applications, primarily as drug delivery vehicles, as well as in gene therapy and for diagnostic imaging.

WO 2008/038292 discloses, inter alia, multilamellar vesicles or liposomes (MLVs) of several phospholipids above their liquid-crystalline-phase to gel-phase transition temperature (Tm) as possible boundary lubricants in the articular cartilage environment.

WO 2011/158237, by some of the present inventors, discloses, inter alia, a method for lowering the friction coefficient of surfaces, which is effected by applying gel-phase liposomes onto surfaces to form a boundary lubricant layer, wherein the temperature of the surface at the time of lubrication is below the phase transition temperature (Tm) of the liposomes. The described method is suitable for lubricating biological and non-biological surfaces, including the surfaces of a biological tissue in a mammalian subject, e.g., for treating joint dysfunction.

Further studies on surface lubrication by liposomes are described in, for example, Klein et al., Faraday Discuss., 1994, 98, p. 173-188; Goldberg et al., *Advanced Materials*, 2011, 23(23), p. 3517-3521; Goldberg et al., *Chemistry and Physics of Lipids*, 2012, 165, p. 374-381; and Goldberg et al., *Biophys. J.*, 2011, 100(10), p. 2403-2411.

A hydrogel is composed of a three-dimensional fibrous network containing up to 99.9% water. Swelling, or uptake of water, is made possible due to the hydrophilic groups attached to the polymer backbone of such hydrogels. The polymer strands may be chemically crosslinked to various extents between groups in the backbone or side-chains, giving rise to a variety of mechanical properties of the hydrogel. Hydrogels can be biocompatible and based on their synthetic or natural occurring polymeric components, can be biodegradable (e.g., by enzymes) or non-biodegradable. These characteristics gave rise to a great interest from the biomaterial field developing many bio-gels based applications including hydrogel-based scaffolds for tissue engineering applications. Among them are the calcium alginate microcapsules [Lim et al., Science, 1980, 210(4472), p. 908-910], alginate hydrogel for myocardial repair [Ruvinov et al., Biomaterials, 2011, 32(2), p. 565-578], and polyethylene glycol hydrogels for neural tissue [Mahoney et al., Biomaterials, 2006, 27(10), p. 2265-2274].

Poly-HEMA-based hydrogel is biocompatible and its water content could reach more than 70%, resembling that of cartilage. Its Young's modulus may be 1 MPa, depending on the exact hydrogel composition, also similar to that of cartilage. Hence, hydrogels based on polymeric constituents such as poly(2-hydroxylethylmethacrylate) (pHEMA) have been investigated for use as synthetic cartilage replacement substance [Petrtyl et al., Acta of Bioengineering and Biomechanics, 12 (3), 2010].

In a study on the tribological properties of pHEMA-based hydrogels for use in artificial cartilage [Bavaresco et al., Wear, 2008, 265 (3-4), p. 269-277], the friction coefficient and wear as a function of different crosslinking densities, crosslinking agents, sliding speed and contact pressures were investigated.

Freeman et al. [Wear, 2000, 241(2), p. 129-135] studied the tribological behavior of pHEMA surface to a stainless steel ball as a function of the load, lubrication, crosslinking density and the degree of the hydrogel hydration.

Gong et al. [, Soft Matter, 2006. 2 (7), p. 544-552] reported the effect of adding surfactants to the water medium on the friction coefficient of a negatively charged polyelectrolyte hydrogel in a parallel-plate rheometer configuration up to low pressures around 1 atm.

Gulsen et al. [*Current Eye Research,* 2005, 30, p. 1071-1080] teach contact lens compositions with drug delivery capabilities, and specifically teach dispersing exceptionally small dimyristoylphosphatidylcholine (DMPC) SUV liposomes (less than 50 nm or 80 nm in diameter) in poly-2-hydroxyethyl methacrylate (p-HEMA) hydrogels, which are a common contact lens material. The results of this study show that the p-HEMA gels loaded with exceptionally small liposomes are transparent and that these gels release drugs for a period of about 8 days.

DiTizio et al. [*Biomaterials,* 1998, 19, p. 1877-1884] teach a liposomal soft hydrogel system that reduces bacterial adhesion to silicone catheter material.

Nagarsenker et al. [International Journal of Pharmaceutics, 1999, 190, p. 63-71] teach liposomes dispersed in soft polycarbophil gel.

Mourtas et al. [*Langmuir,* 2009, 25(15), p. 8480-8488] teach rheological properties of complex soft and semi-solid hydrogels containing different amounts of liposomes and/or cyclodextrin.

Kang et al. [*Journal of Drug Targeting*, 2010; 18 (8), p. 637-644] teach cationic liposomes composed from less than 50% phosphatidylcholine lipids, dispersed in a soft thermosensitive gel.

Mechanical properties of layers of stable liposomes attached onto solid surfaces, including surfaces of hydrogels, were studied by atomic force microscopy (AFM) force measurements [Brochu, Ph.D. Thesis in the Université de Sherbrooke, Canada, 2008, Id.: 50177338].

Additional prior-art documents include U.S. Patent Application Publication Nos. 20040171740, 20060270781 and 20110293699, and U.S. Pat. Nos. 7,638,137 and 8,273,366.

SUMMARY OF THE INVENTION

The present inventors have uncovered that incorporation of liposomes within hydrogels result in substantial reduction of the friction coefficient of the hydrogels and have therefore designed and successfully practiced compositions comprising a hydrogel, or a composite material comprising the hydrogel, and liposomes, in which the liposomes are dispersed within the hydrogel. Hereinafter, the term "hydrogel" refers also to a composite material containing a hydrogel, unless specified otherwise. The present inventors have demonstrated that these compositions exhibit a substantially reduced friction coefficient as compared to the hydrogel (or a composite material containing same) per se (without the liposomes) and hence can be utilized in various applications in which hydrogels that exhibit low friction coefficient are desired.

According to an aspect of some embodiments of the present invention, there is provided a composition which includes a hydrogel or a composite material containing a hydrogel, and a plurality of liposomes dispersed throughout the bulk of the hydrogel, the composition being characterized by a dynamic shear storage modulus (G') of at least 1000 Pa, wherein:

an average diameter of the liposomes is larger than 80 nm; and/or a degree of crosslinking of the hydrogel is higher than 0.2 molar percent.

According to some of any of the embodiments described herein, the concentration of the liposomes is higher than 4 mM.

According to some of any of the embodiments described herein, the average diameter of the liposomes is larger than 80 nm.

According to some of any of the embodiments described herein, the degree of crosslinking of the hydrogel is higher than 0.2 molar percent.

According to some of any of the embodiments described herein, the degree of crosslinking of the hydrogel is 0.2 molar percent or lower.

According to some of any of the embodiments described herein, the concentration of the liposomes is higher than 4 mM, whereby the degree of crosslinking of the hydrogel is higher or lower than 0.2 molar percent.

According to some of any of the embodiments described herein, the concentration of the liposomes is 4 mM or lower, whereby the degree of crosslinking of the hydrogel is higher or lower than 0.2 molar percent.

According to some of any of the embodiments described herein, the concentration of the liposomes is 4 mM or lower, whereby the degree of crosslinking of the hydrogel is higher or lower than 0.2 molar percent.

According to some of these embodiments, the degree of crosslinking of the hydrogel is higher than 0.2 molar percent.

According to some of any of the embodiments described herein, the average diameter of the liposomes is 80 nm or lower.

According to some of these embodiments, the concentration of the liposomes is higher than 4 mM.

According to some of these embodiments, the concentration of the liposomes is 4 mM or lower.

According to some of any of the embodiments described herein, the degree of crosslinking ranges from 0.5 molar percent to 8 molar percent.

According to some of any of the embodiments described herein, the diameter of the liposomes is greater than 100 nm.

According to some of any of the embodiments described herein, the diameter ranges from 100 nm to 700 nm.

According to some of any of the embodiments described herein, the diameter ranges is larger than 700 nm.

According to some of any of the embodiments described herein, the liposomes further comprise an additional agent selected from the group consisting of a polymer, a hydrogel-forming polymer, cholesterol, a liposome-stabilizing agent, a labeling agent, a bioactive agent and a therapeutically active agent.

According to some embodiments, the additional agent is a polymer, and according to some embodiments it is a hydrogel-forming polymer.

According to some embodiments, the polymer is selected from the group consenting of poly(2-hydroxyethyl methacrylate) (pHEMA), alginate and hyaluronic acid (HA).

According to some embodiments of any of embodiments of the present invention, the additional agent is cholesterol.

According to some embodiments, the concentration of the cholesterol ranges from 1 molar percent to 50 molar percent relative to a total lipid amount of the liposome, or lower.

According to some embodiments, the concentration of cholesterol is 40 molar percent or lower, relative to a total lipid amount of said liposome.

According to some embodiments, the concentration of cholesterol ranges from 1 molar percent to 15 molar percent relative to a total lipid amount of said liposome.

According to some embodiments, the concentration of cholesterol ranges from 5 molar percent to 10 molar percent relative to a total lipid amount of said liposome.

According to some of any of the embodiments described herein, the hydrogel is formed of a hydrogel-forming agent being selected from the group consisting of hydroxyethyl methacrylate (HEMA), hydroxyethyl acrylate (HEA), acrylamide (AAm), methacrylamide (MAAm), acrylic acid (AAc), methacrylic acid (MAAc), hydroxyethyl acrylate (HEA), hexyl methacrylate, N-isopropylacrylamide (NiPAAm)), N-isopropylmethacrylamide, polylactic acid, polyamide, polyethylene-terephthalate (PET), polyvinyl alcohol, polyurethane, polycaprolactone, polyethylene-glycol (PEG), polyethyleneoxide dimethacrylate (PEOdMA), N,N-dimethacrylamide (nnDMAA), hyaluronic acid (HA), HA methacrylate, peptides, saccharides, gelatin, gelatin methacrylate, chitosan, chitosan methacrylate, glycol chitosan, glycol chitosan methacrylate, alginate, alginate methacrylate, cellulose, siloxanes, polysiloxanes, and any oligomer and/or polymer thereof, in any combination thereof.

According to some of any of the embodiments described herein, the hydrogel is formed of hydroxyethyl methacrylate (HEMA) and/or poly hydroxyethyl methacrylate (pHEMA).

According to some of any of the embodiments described herein, the hydrogel further comprises a hydrogel-forming agent which is selected from the group consisting of methacrylic acid, methacrylamide, polyethyleneoxide dimethacrylate, acrylamide and N,N-dimethacrylamide (nnDMAA).

According to some of any of the embodiments described herein, the hydrogel is formed of gelatin methacrylate.

According to some embodiments, a degree of methacrylation in the gelatin methacrylate ranges from 10 percents to 90 percents.

According to some embodiments, the degree of methacrylation in the gelatin methacrylate is 75 percents.

According to some embodiments, the composition as described in any one of the embodiments herein, and any combination thereof, is in a dry form.

In some embodiments, the dry form of the composition can be re-hydrated.

According to another aspect of some embodiments of the present invention, there is provided a process of preparing the composition as described herein, in any one of the embodiments thereof, and any combination thereof, the method comprising mixing an aqueous suspension of the liposomes with a hydrogel-forming agent, as described in any of the respective embodiments herein, in the presence of a crosslinking agent (which optionally can form a part of the hydrogel-forming agent), thereby obtaining the composition.

According to some of any of the embodiments of this aspect of the present invention, the suspension further comprises an initiator.

According to some of any of the embodiments of this aspect of the present invention, the suspension further comprises a catalyst.

According to some of any of the embodiments of this aspect of the present invention, the process further comprises dehydrating the composition.

According to some of any of the embodiments of this aspect of the present invention, the process further comprises, subsequent to the dehydrating, rehydrating the composition.

According to some of any of the embodiments of this aspect of the present invention, the crosslinking agent is selected from the group consisting of poly(ethylene glycol)$_n$ dimethacrylate (EGDMA), polyethyleneoxide dimethacrylate (PEOdMA), N,N'-methylenebisacrylamide (MBA or MBAm), N,N'-methylenebis(2-methylacrylamide), methylene diacrylate, methylene bis(2-methylacrylate), diethylene glycol diacrylate, hexamethylene diacrylate, oxybis(methylene) bis(2-methylacrylate) and oxybis(ethane-2,1-diyl) bis (2-methylacrylate).

According to an aspect of some embodiments of the present invention, there is provided a composition prepared by the process described herein, in any one of the embodiments thereof, and any combination thereof.

According to some of any of the embodiments of the present invention, the composition presented herein is characterized by a dynamic friction coefficient in aqueous medium that ranges from 0.001 to 0.08 under a pressure of at least 1 atmosphere.

According to some of any of the embodiments of the present invention, the composite material comprises a material selected from the group consisting of a woven mesh of fibers, non-woven fibers, a plurality of rods and a net.

According to some of any of the embodiments of the present invention, the composition is characterized by a dynamic friction coefficient in aqueous medium that ranges from 0.001 to 0.08 under a pressure of at least 1 atmosphere.

According to another aspect of embodiments of the present invention, there is provided a method of lowering a friction coefficient of a hydrogel or of a composite material containing a hydrogel, the method comprising forming the hydrogel in the presence of a plurality of liposomes.

According to some of any of the embodiments of the present invention, forming the hydrogel is such that the liposomes are dispersed throughout the bulk of the hydrogel.

According to some of any of the embodiments of the present invention, the hydrogel or composite material containing a hydrogel features a dynamic shear storage modulus (G') of at least 1000 Pa.

According to some of any of the embodiments of the present invention, the method is effected such that the dynamic friction coefficient in aqueous medium of the hydrogel or composite material containing a hydrogel having the liposomes dispersed therein ranges from 0.001 to 0.08 under a pressure of at least 1 atmosphere.

According to some of any of the embodiments of the present invention, the method is effected such that the dynamic friction coefficient in aqueous medium of the hydrogel or composite material containing a hydrogel having the liposomes dispersed therein is reduced by a factor of at least 52 relative to the friction coefficient of the hydrogel not having the liposomes dispersed therein.

According to some of any of the embodiments of the present invention, the method further comprises dehydrating the hydrogel or the composite material containing a hydrogel and rehydrating the hydrogel.

According to some of any of the embodiments of the present invention, the method, composite or composition presented herein comprises liposomes which are selected from the group consisting of small unilamellar vesicles (SUV), large unilamellar vesicles (LUV) and multilamellar vesicles (MLV).

According to some of any of the embodiments of the present invention, the liposomes comprise at least one phosphatidylcholine phospholipid.

According to some of any of the embodiments of the present invention, the liposomes comprise at least 50 molar percent of the phosphatidylcholine phospholipid.

According to some of any of the embodiments of the present invention, the water content of the hydrogel when fully hydrated ranges from 30% to 99% by weight of the total weight of the composition.

According to some of any of the embodiments of the present invention, the friction coefficient is substantially maintained at room temperature.

According to some of any of the embodiments of the present invention, the friction coefficient is substantially maintained at 37° C.

According to some of any of the embodiments of the present invention, the friction coefficient is substantially maintained over a period of at least 60 minutes under essentially constant load and temperature.

According to some of any of the embodiments of the present invention, the friction coefficient is substantially maintained after at least one dehydration-rehydration cycle.

According to an aspect of some embodiments of the present invention, there is provided an article-of-manufacturing which comprises the composition or composite material as described herein, in any one of the respective embodiments, and any combination thereof.

According to some embodiments, the article-of-manufacturing is selected from the group consisting of an implantable medical device, a drug-delivery system, a solid body, a disc, a fiber, a fabric, a tube, a film, a rod, a ring, a tubular mesh and any combination thereof.

According to an aspect of some embodiments of the present invention, there is provided a use of the article-of-manufacturing as described herein, in any of the respective embodiments, and any combination thereof, for an application selected from the group consisting of surface coating, friction-reduction, and a cutting tool coating.

According to an aspect of some embodiments of the present invention, there is provided a method of treating a living organism suffering from a medical condition associated with loss of, or damaged, cartilage, the method comprising replacing at least a portion of the cartilage with the composition or composite material as described herein, in any of the respective embodiments, and any combination thereof.

According to some embodiments, the composition described herein, in any of the respective embodiments, and any combination thereof is for use in replacing missing or damaged cartilage in a living organism suffering from a medical condition associated with loss of or damaged cartilage.

According to some embodiments, the composition as described herein, in any of the respective embodiments, and any combination thereof is for use in a skeletal joint replacement or reconstruction, vertebrate replacement or reconstruction, tendon replacement, tissue regeneration and reduction of tissue irritation by an implantable device.

According to an aspect of some embodiments of the present invention, there is provided a use of the composition as described herein, in any of the respective embodiments, and any combination thereof, for coating an article-of-manufacturing.

According to another aspect of embodiments of the present invention, there is provided a use of the composition as described herein, in any of the respective embodiments, and any combination thereof for lowering the friction coefficient of a surface under aqueous conditions.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Figure 11A:
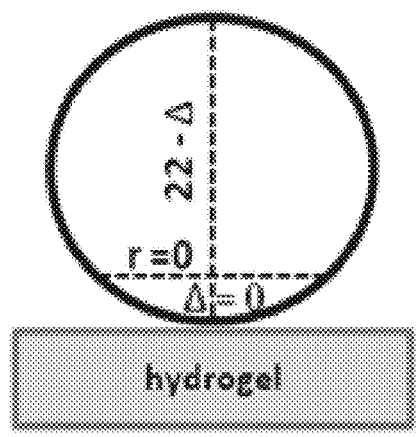
Figure 11B:
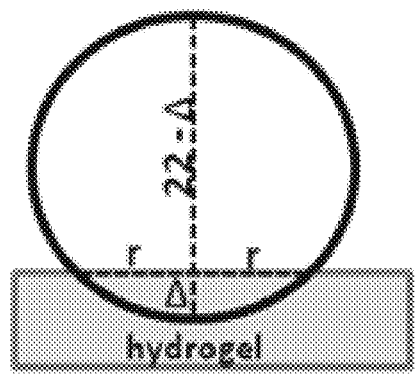
Figure 13A:
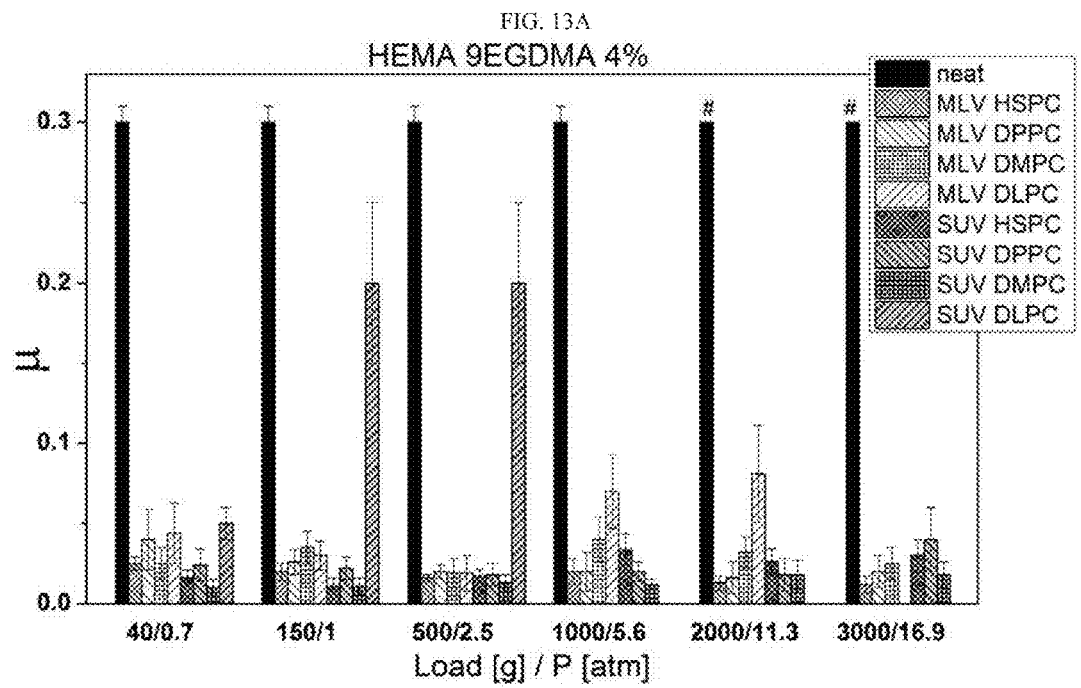
Figure 13B:
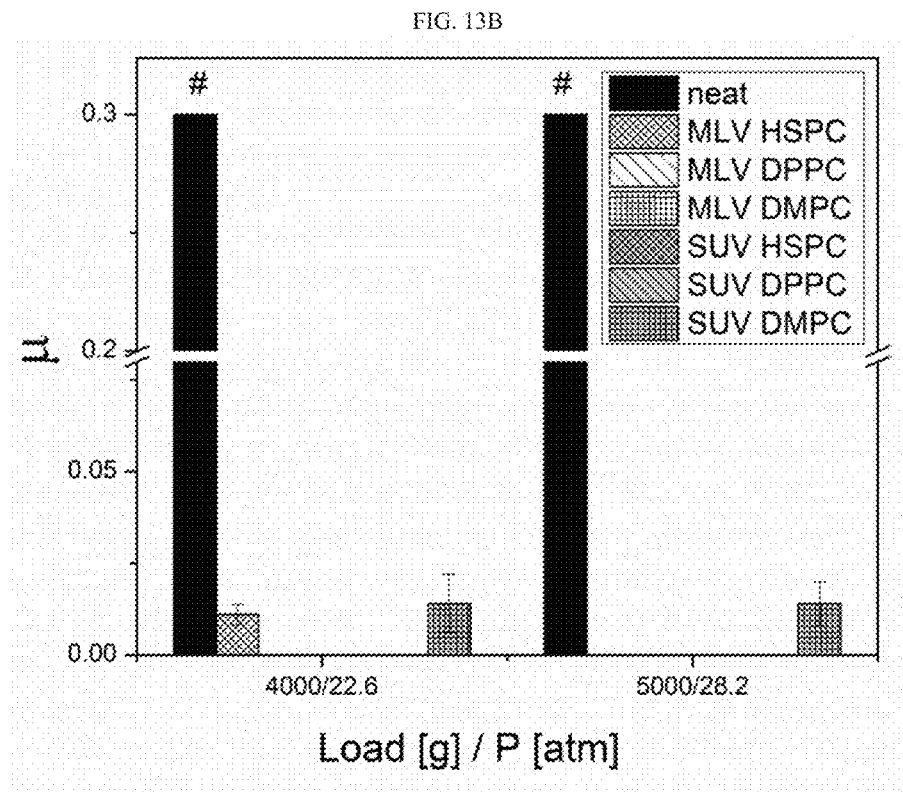
Figure 14A:
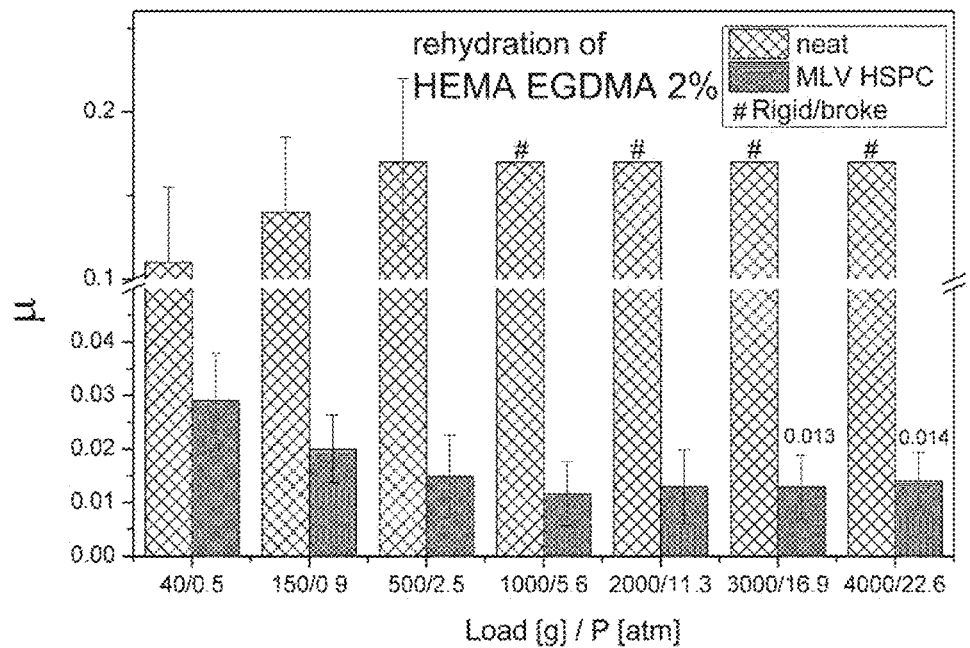
Figure 14B:
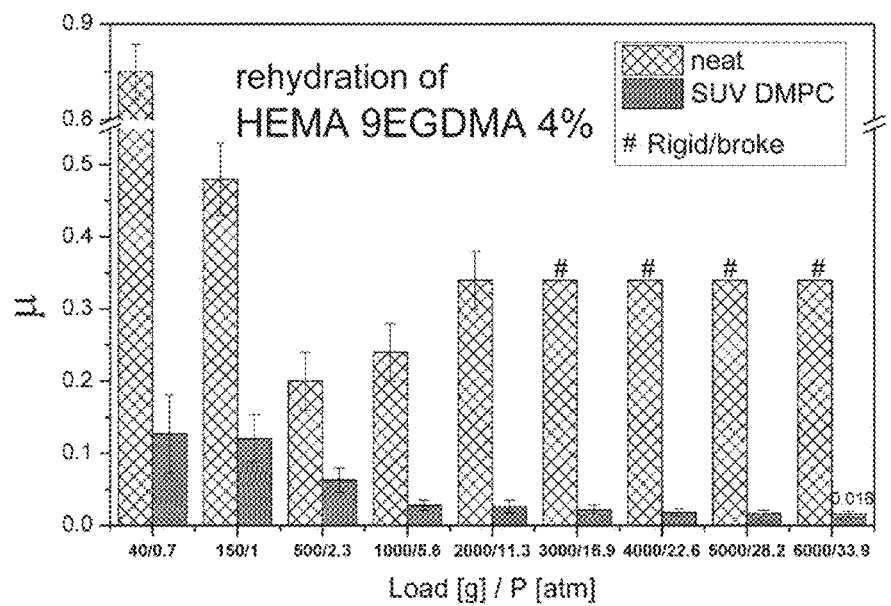
Figure 15:
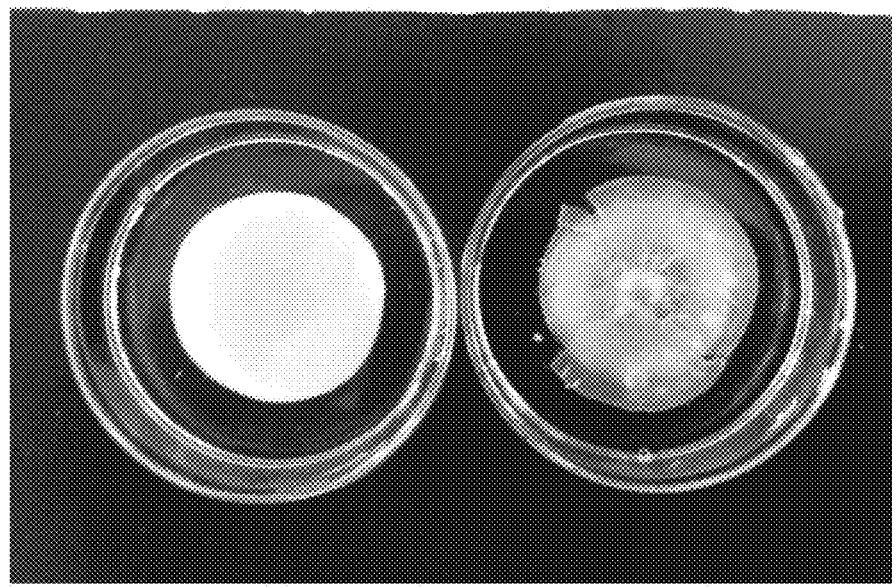
Figure 16:
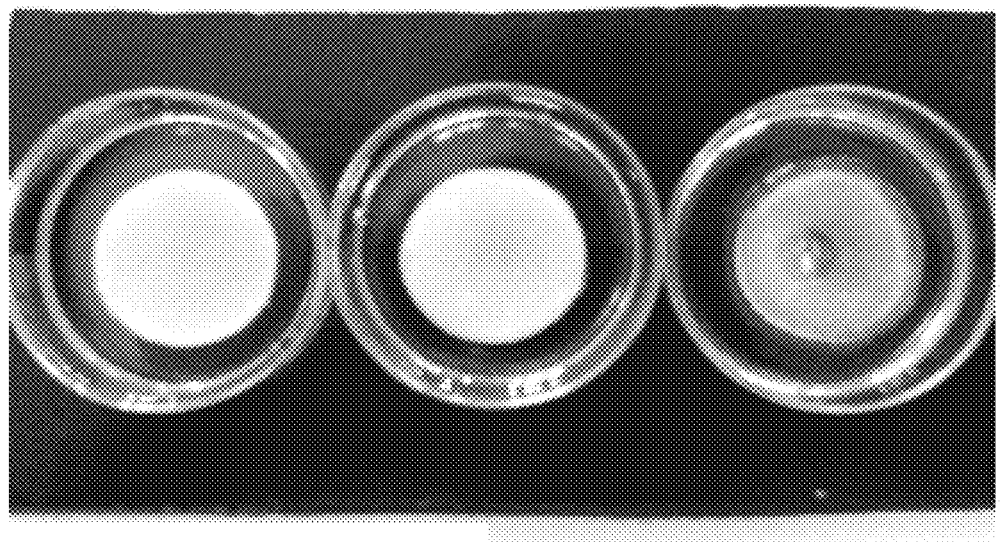
Figure 17:
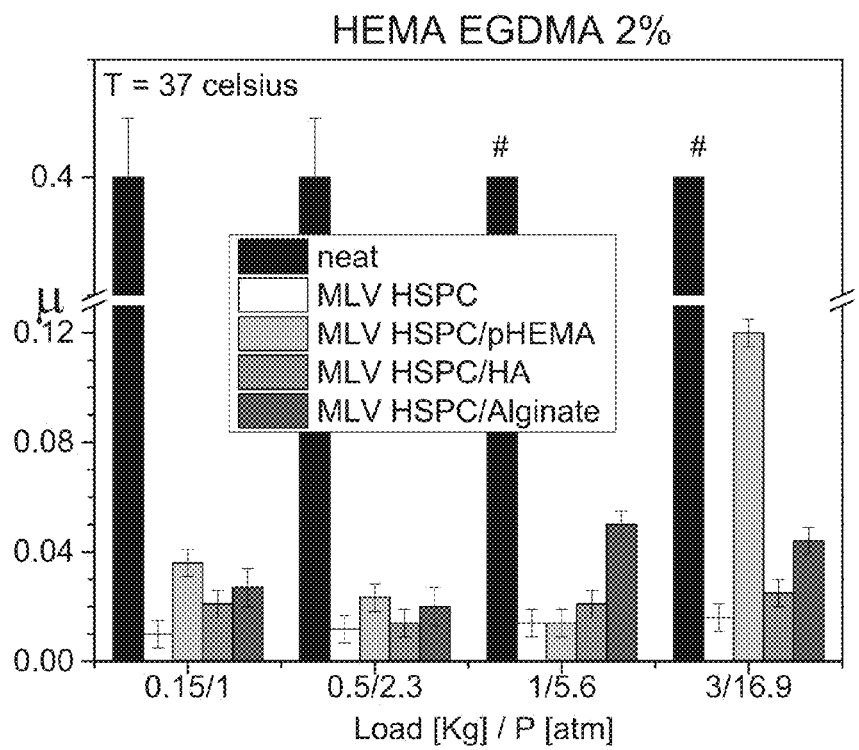
Figure 18:
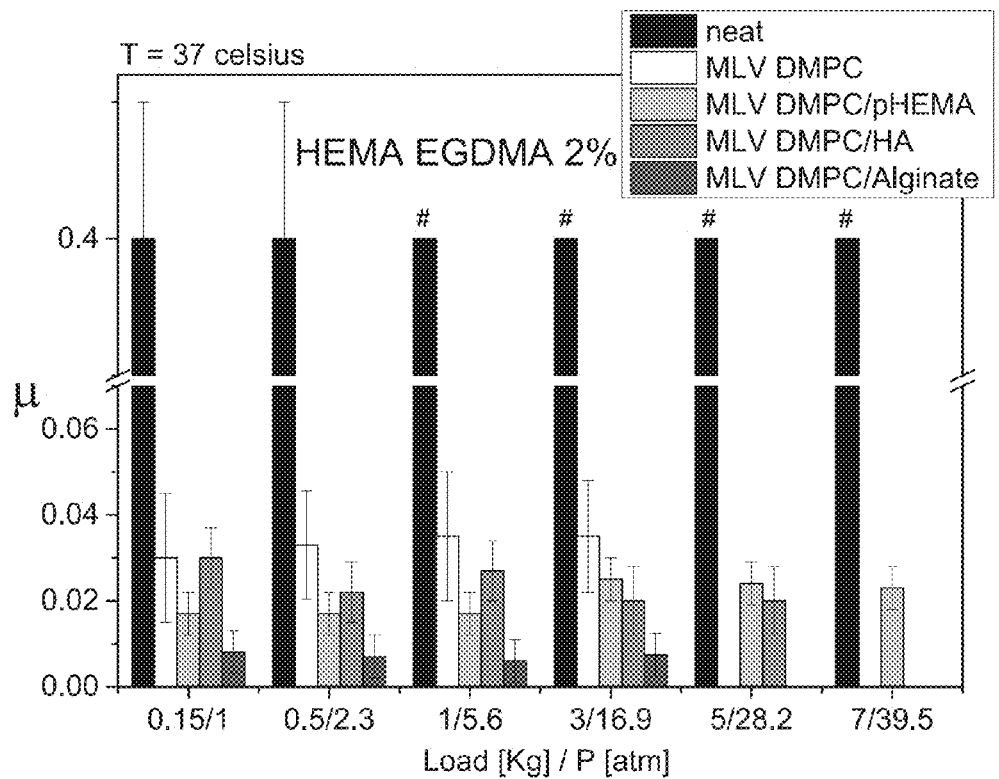
Figure 19:
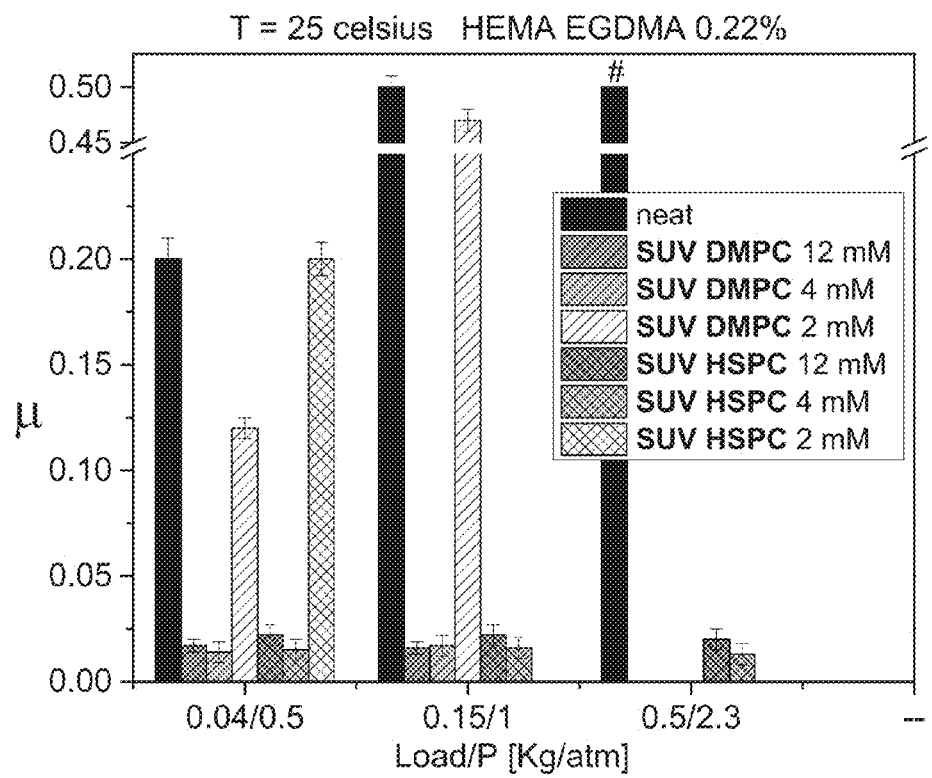
Figure 20:
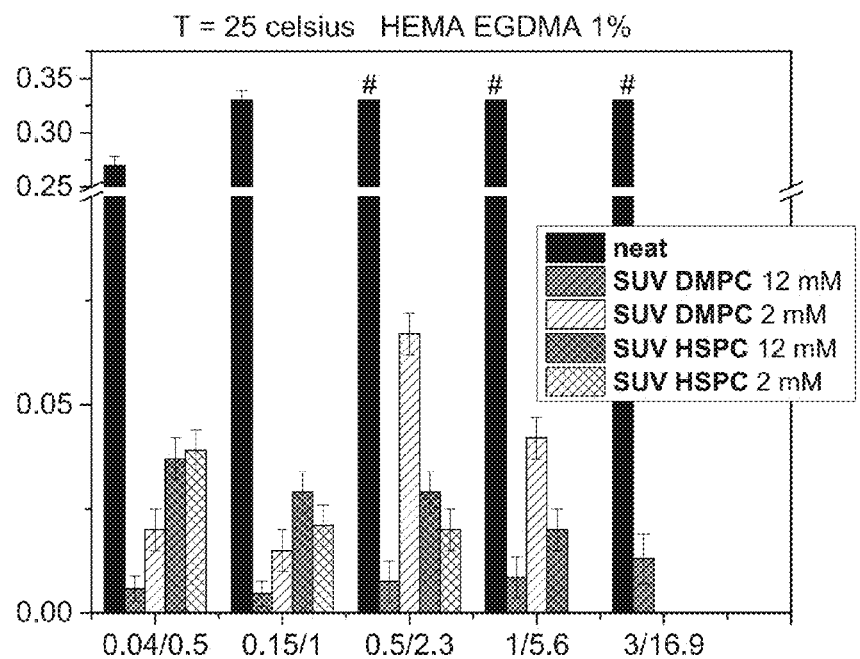
Figure 21:
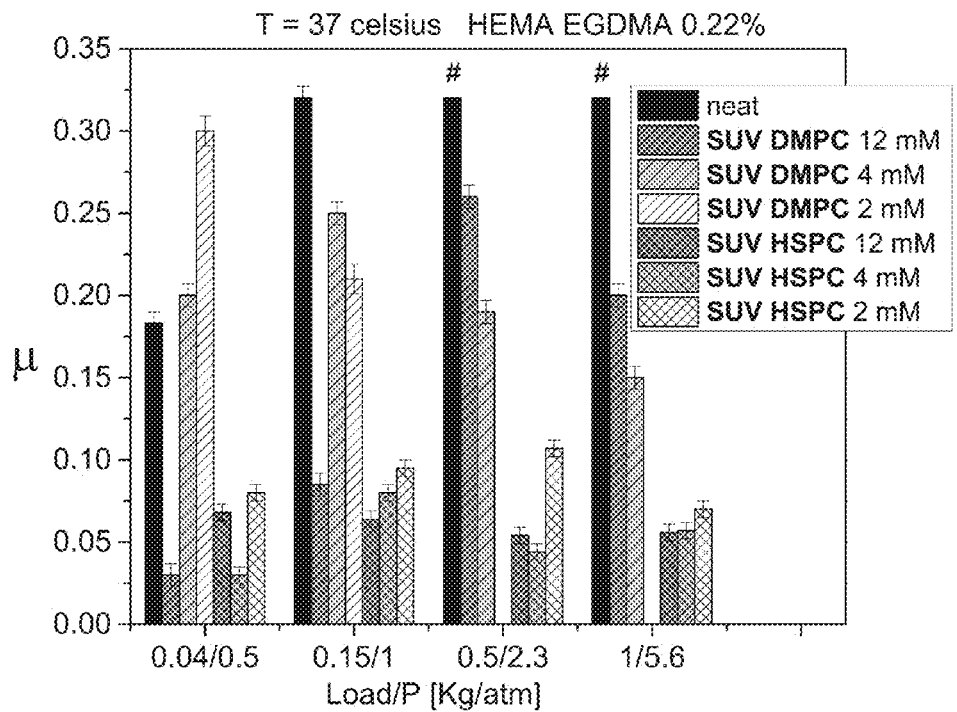
Figure 22:
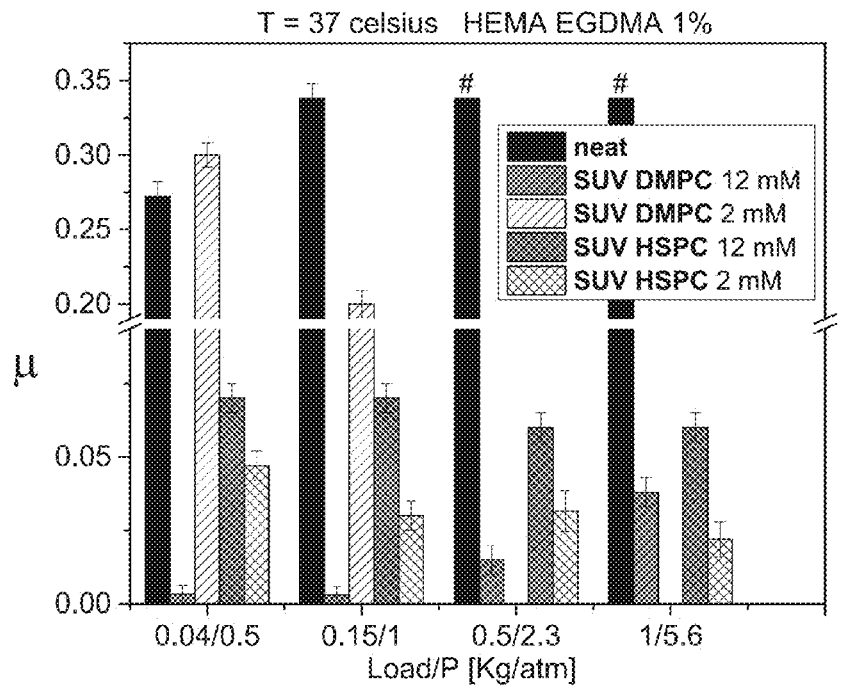
Figure 23:
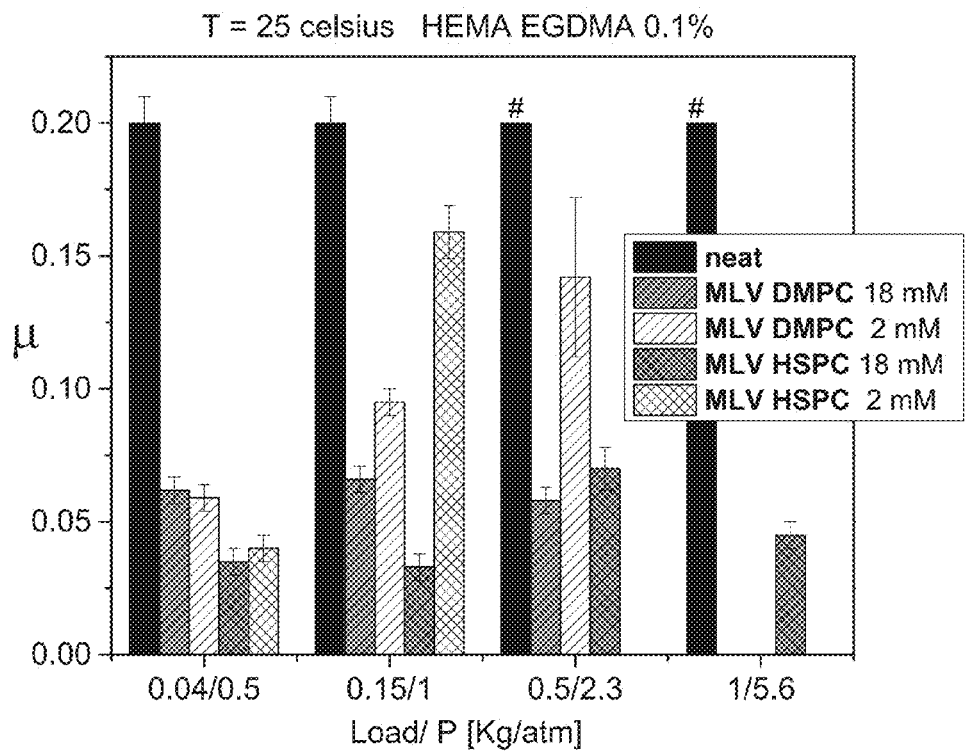
Figure 24:
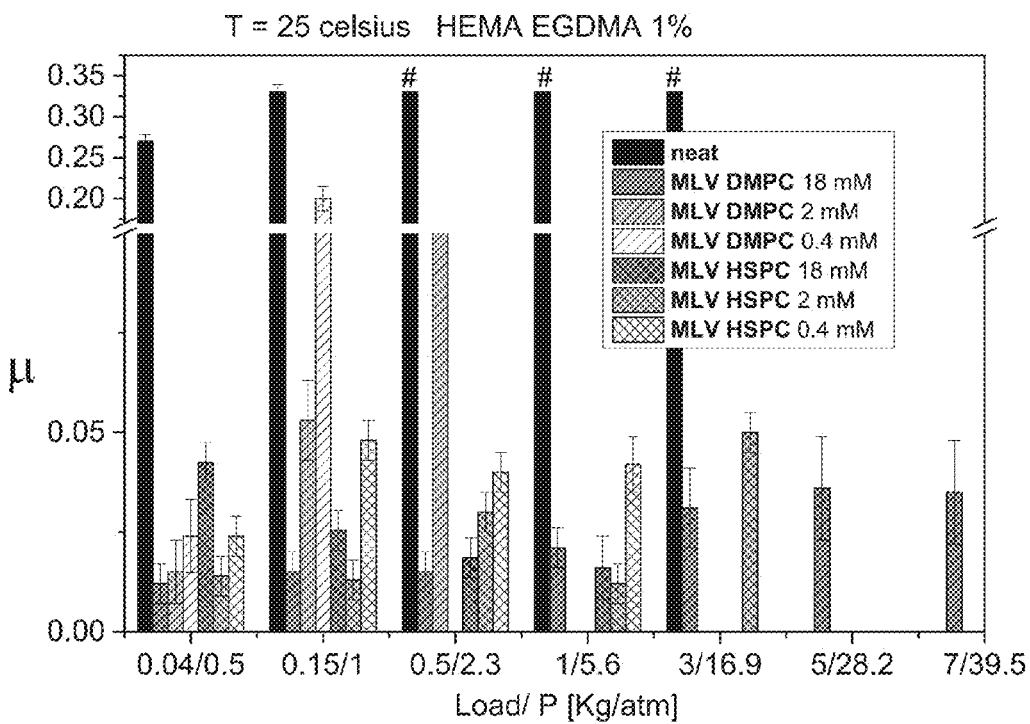
Figure 25:
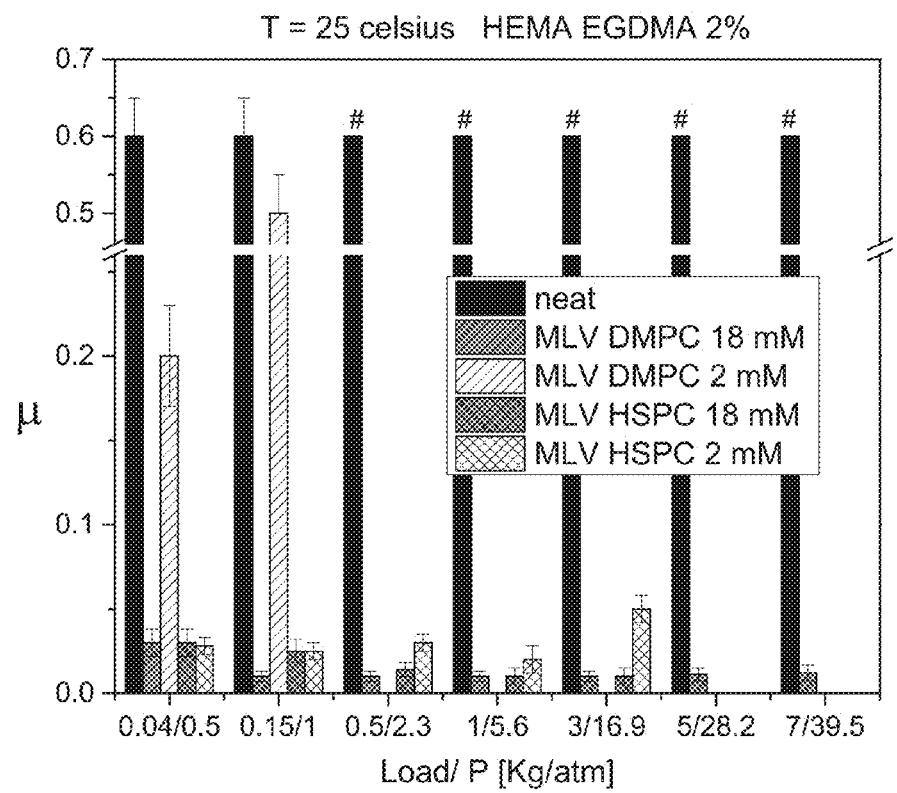
Figure 26:
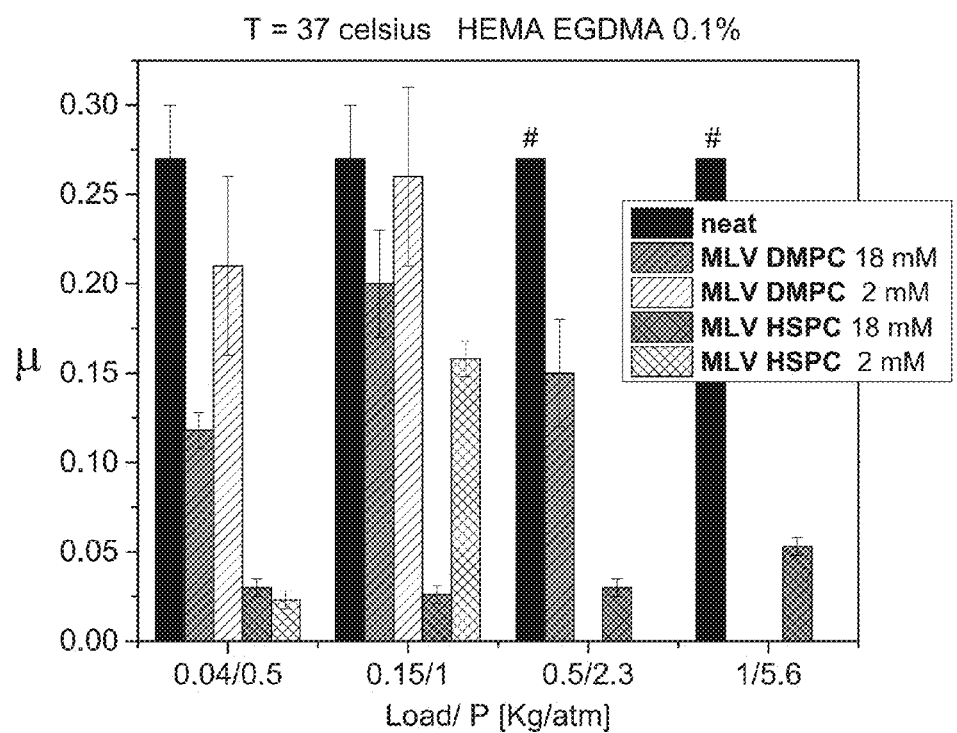
Figure 27:
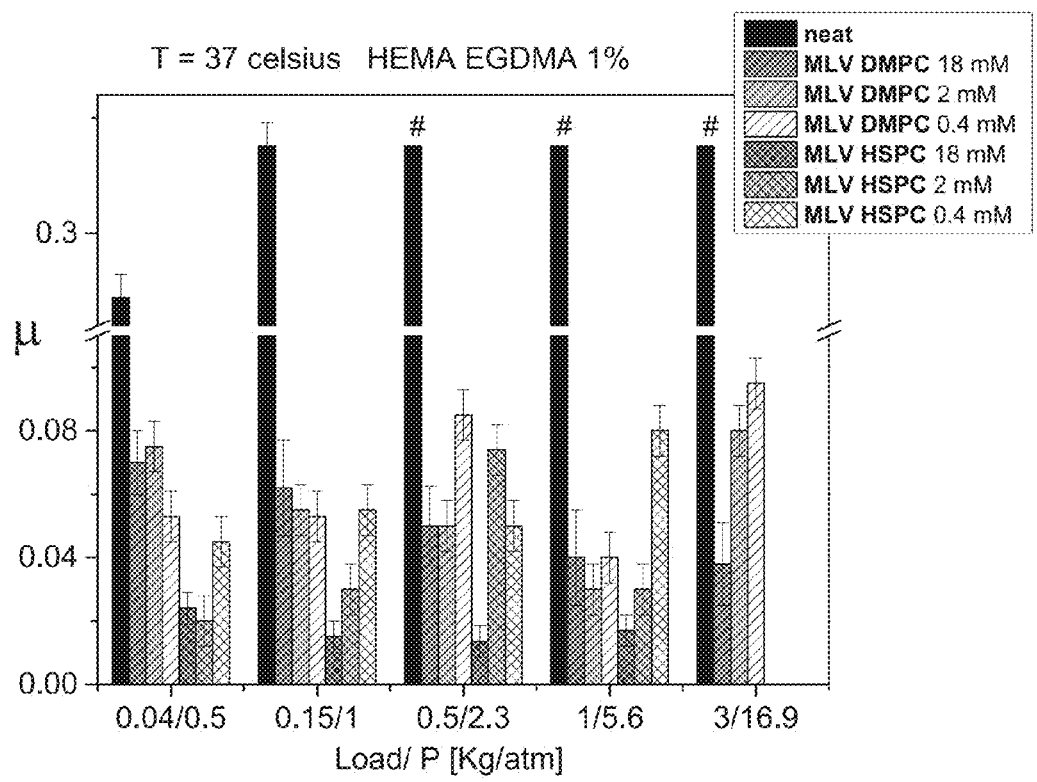
Figure 28:
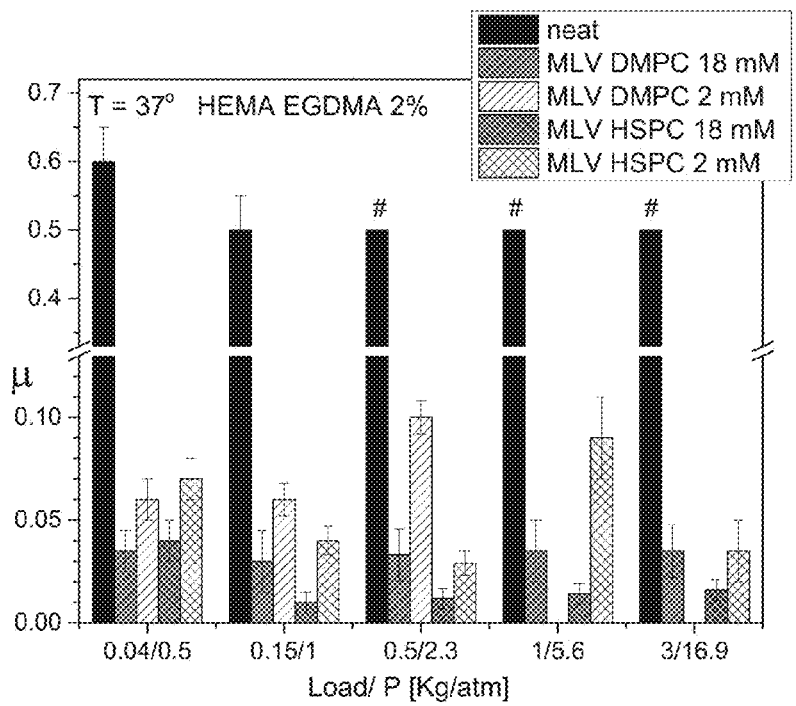
Figure 29:
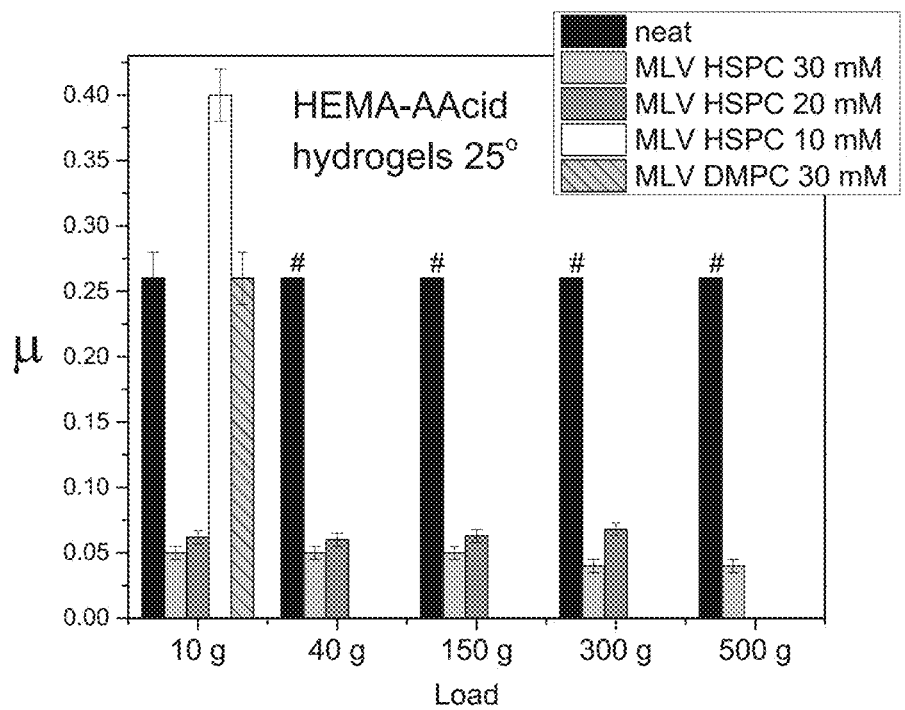
Figure 30:
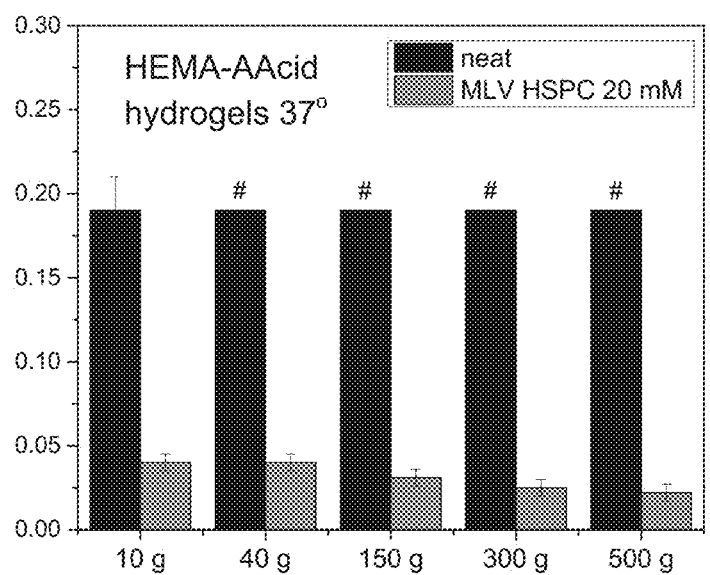
Figure 31:
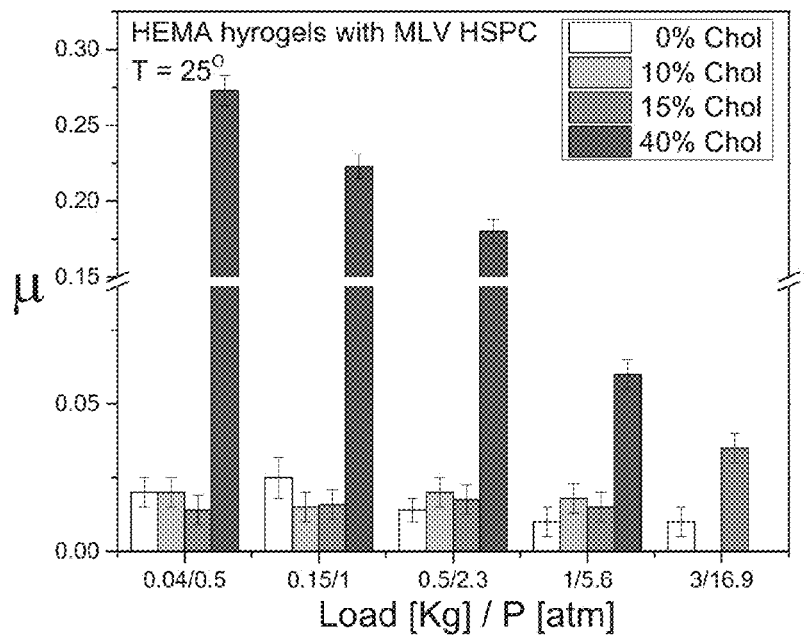
Figure 32:
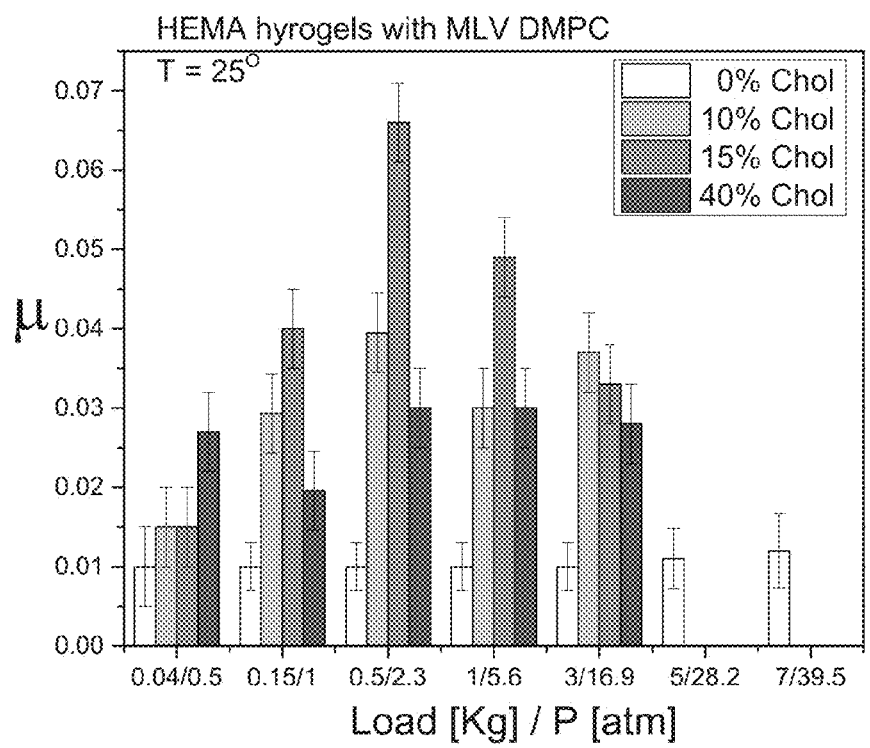
Figure 33:
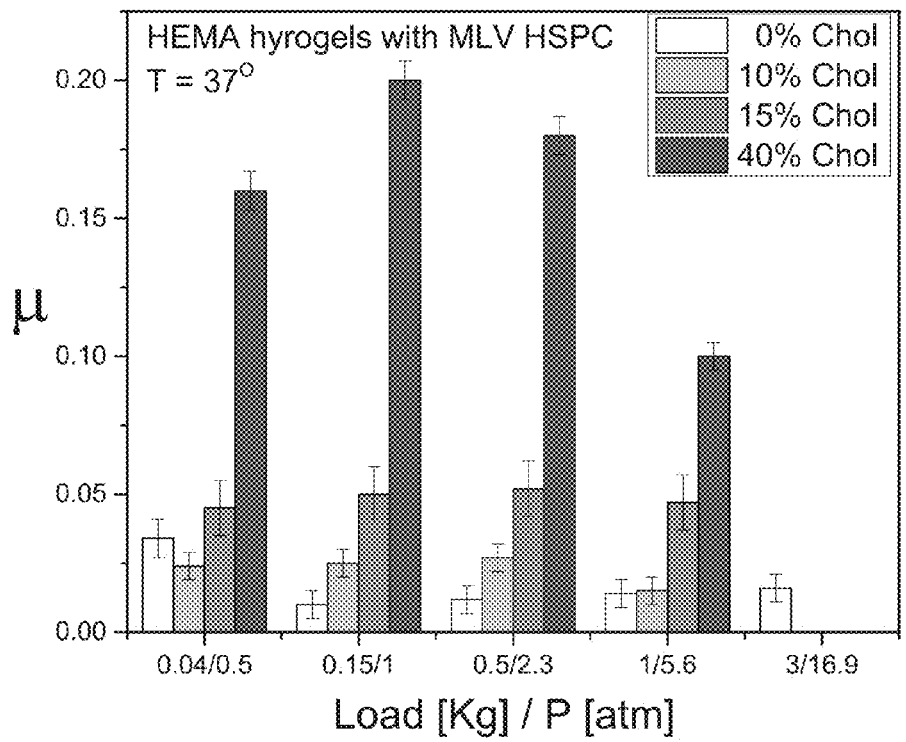
Figure 34:
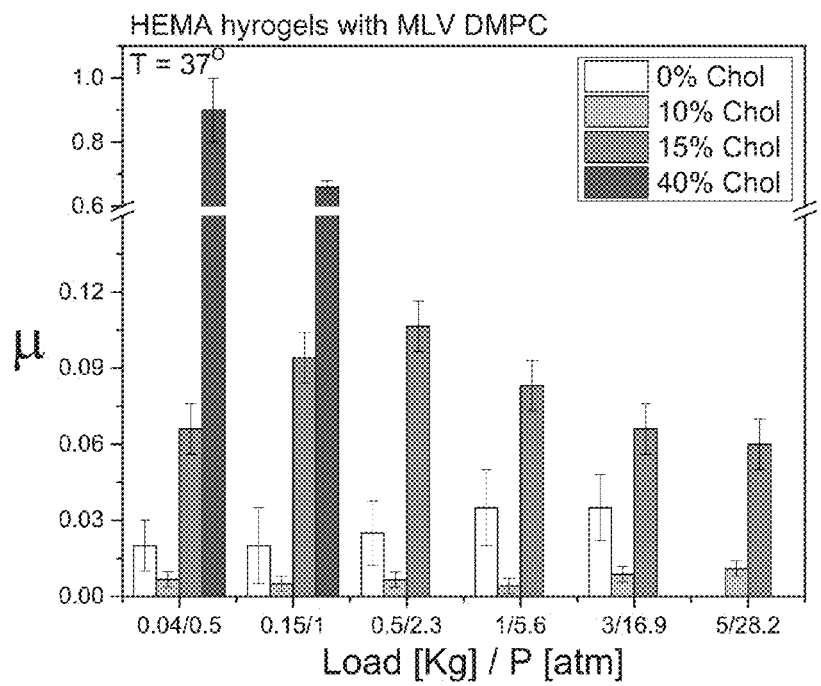
Figure 35:
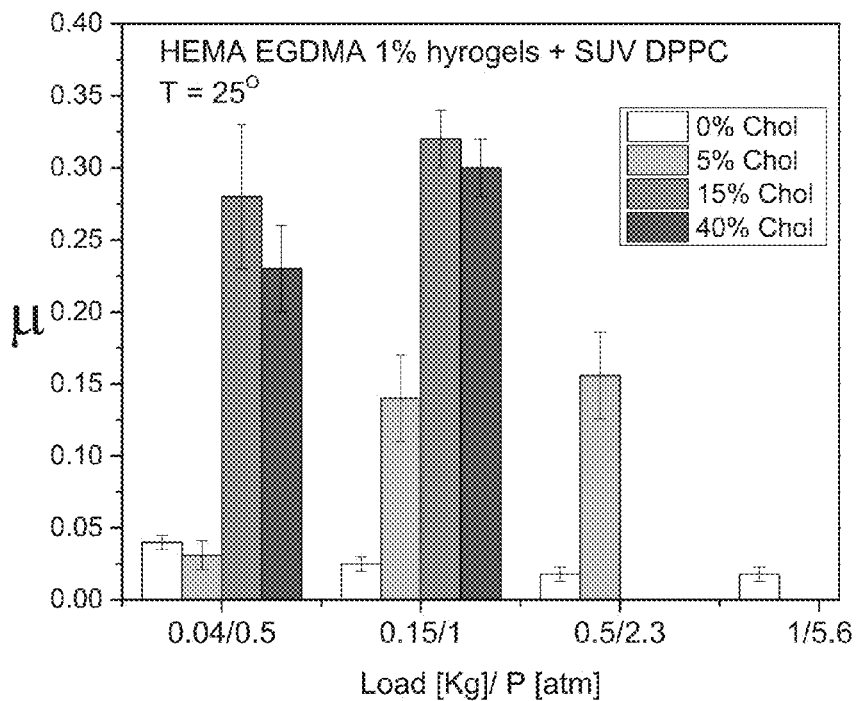
Figure 36:
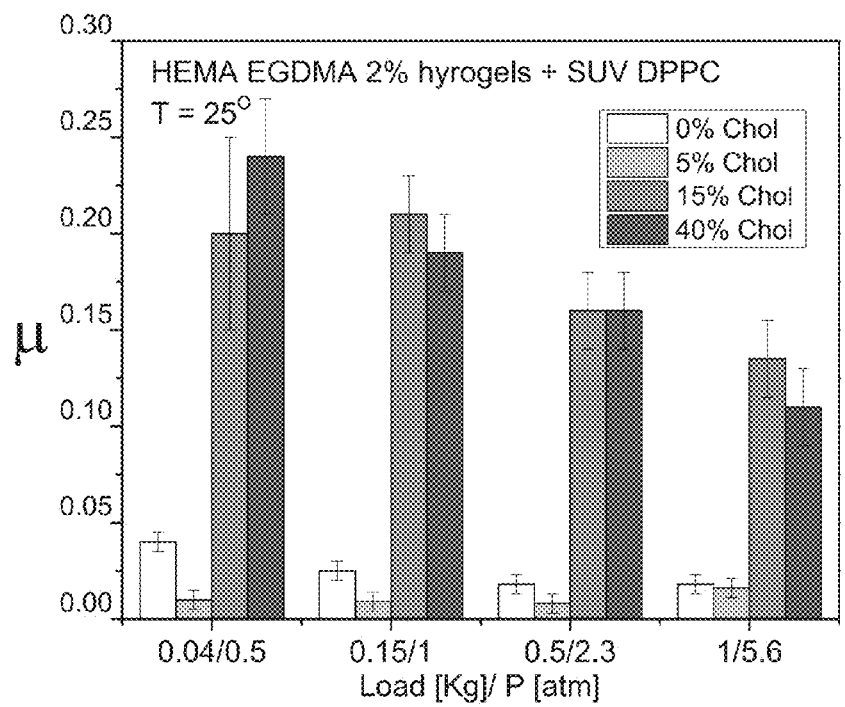
Figure 37:
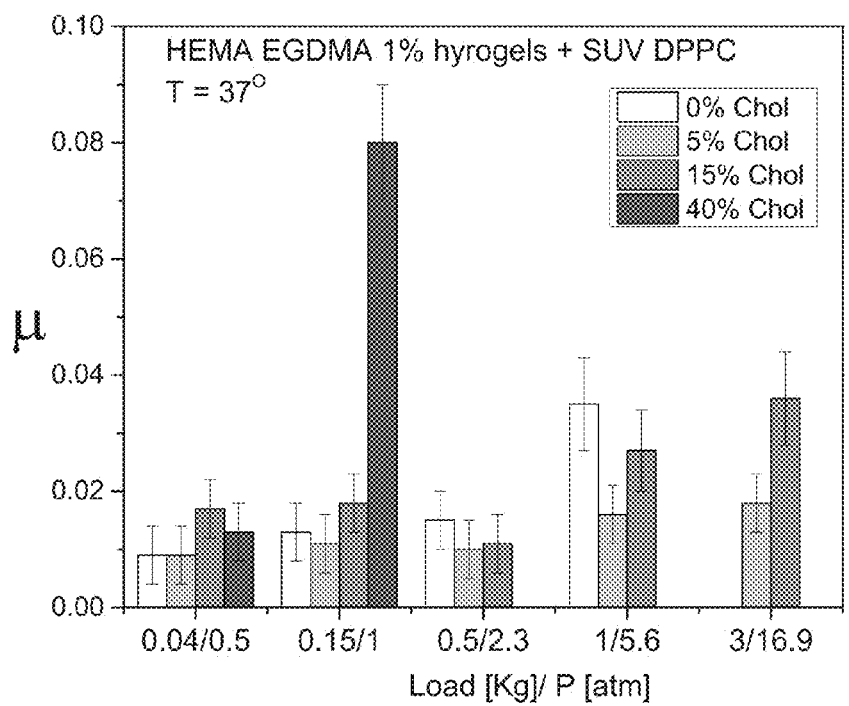
Figure 38:
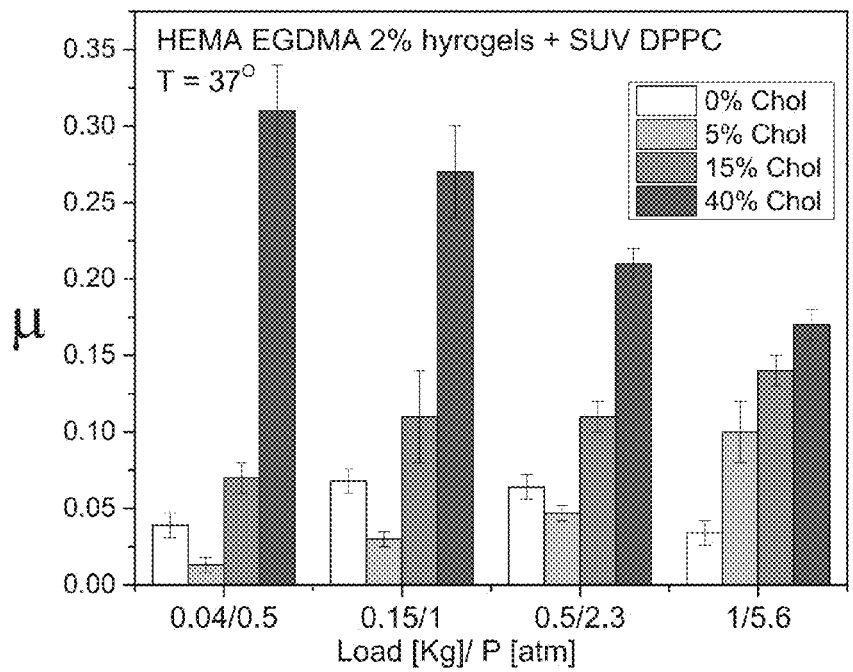

MLV DSPC under pressure of about 7 atmospheres, while the shear amplitude was 1 mm;

FIGS. 11A-B present a schematic illustration of the gel-to-metal friction measurement geometry, wherein "r" is defined as the radius of the contact area, also from geometry $r^2=\Delta(22-\Delta)$, where $\Delta$ is the difference in the height of the indented hydrogel (FIG. 11A) comparing to the zero position prior to applying the normal force (FIG. 11B), and 22 (mm) is the metal sphere diameter, whereas $\Delta$ was measured for each of the applied normal loads, and the pressure P was calculated accordingly;

FIGS. 12A-E present the friction coefficient reduction results as measured in the gel-to-metal configuration achieved by incorporation of MLV HSPC liposomes into HEMA EGDMA 0.1% (FIG. 12A), HEMA EGDMA 0.5% (FIG. 12B), HEMA EGDMA 1% (FIG. 12C) and HEMA EGDMA 2% (FIGS. 12D-E) hydrogels, whereas the "#" symbol indicates a rigid coupling scenario or case of a hydrogel tearing during the experiment;

FIGS. 13A-B present the friction coefficient reduction results as measured in the gel-to-metal configuration achieved by incorporation of liposomes to the HEMA 9EGDMA 4% hydrogel, measured at 25° C. under loads of 40-3000 grams (FIG. 13A) and loads of 4000-5000 grams (FIG. 13B);

FIGS. 14A-B present a comparative bar-graph, showing friction coefficient reduction measured in the gel-to-metal configuration measured for a HEMA EGDMA 2% neat hydrogel (crisscross pattern bars) and for HEMA EGDMA 2% hydrogel+MLV HSPC liposomes incorporated therein (solid grey bars) (FIG. 14A) and the results obtain for HEMA EGDMA 4% neat (crisscross pattern bars) and HEMA EGDMA 4% hydrogel+MLV HSPC liposomes (solid grey bars) (FIG. 14B), after dehydrating and rehydrating the hydrogels as described herein, wherein the "#" symbol indicates rigid coupling and/or mechanical failure of the sample;

FIG. 15 presents a photograph of a sample of neat HEMA EGDMA 2% hydrogel (right-hand side) and an exemplary HEMA EGDMA 2% hydrogel containing DMPC MLV liposomes (left-hand side), according to some embodiments of the present invention, which have been subjected to a load of 5 Kg against a metal head in pure water at a temperature of 25° C.;

FIG. 16 presents a photograph of a sample of neat HEMA EGDMA 2% hydrogel (right-hand side), an exemplary HEMA EGDMA 2% hydrogel containing MLV HSPC liposomes (center), and an exemplary HEMA EGDMA 2% hydrogel containing MLV DMPC liposomes (left-hand side), according to some embodiments of the present invention, which have been subjected to a load of 1 Kg against a metal head in pure water at a temperature of 25° C.;

FIG. 17 presents a comparative bar plot of the effective friction coefficients measured for neat HEMA hydrogel, and for various exemplary HSPC liposome-encapsulating HEMA hydrogels, according to some embodiments of the present invention, comparing the effect of adding MLV HSPC liposomes prepared with and without the presence of a polymer on the friction coefficient ($\mu$);

FIG. 18 presents a comparative bar plot of the effective friction coefficients measured for neat HEMA hydrogel, and for various exemplary DMPC liposome-encapsulating HEMA hydrogels, according to some embodiments of the present invention, comparing the effect of adding MLV DMPC liposomes prepared with and without the presence of a polymer on the friction coefficient ($\mu$);

FIG. 19 presents a comparative bar-plot, showing the results of the friction coefficient measurements conducted at 25° C. for neat HEMA EGDMA 0.22% and HEMA EGDMA 0.22%+SUV DMPC or HSPC at a liposome concentrations of 2 mM, 4 mM and 12 mM;

FIG. 20 presents a comparative bar-plot, showing the results of the friction coefficient measurements conducted at 25° C. for neat HEMA EGDMA 1% and HEMA EGDMA 1%+SUV DMPC or HSPC at a liposome concentrations of 2 mM and 12 mM;

FIG. 21 presents a comparative bar-plot, showing the results of the friction coefficient measurements conducted at 37° C. for neat HEMA EGDMA 0.22% and HEMA EGDMA 0.22%+SUV DMPC or HSPC at a liposome concentrations of 2 mM, 4 mM and 12 mM;

FIG. 22 presents a comparative bar-plot, showing the results of the friction coefficient measurements conducted at 37° C. for neat HEMA EGDMA 1% and HEMA EGDMA 1%+SUV DMPC or HSPC at a liposome concentrations of 2 mM and 12 mM;

FIG. 23 presents a comparative bar-plot, showing the results of the friction coefficient measurements conducted at 25° C. for neat HEMA EGDMA 0.1% and HEMA EGDMA 0.1%+MLV DMPC or HSPC at a liposome concentrations of 2 mM and 18 mM;

FIG. 24 presents a comparative bar-plot, showing the results of the friction coefficient measurements conducted at 25° C. for neat HEMA EGDMA 1% and HEMA EGDMA 1%+MLV DMPC or HSPC at a liposome concentrations of 0.4 mM, 2 mM and 18 mM;

FIG. 25 presents a comparative bar-plot, showing the results of the friction coefficient measurements conducted at 25° C. for neat HEMA EGDMA 2% and HEMA EGDMA 2%+MLV DMPC or HSPC at a liposome concentrations of 2 mM and 18 mM;

FIG. 26 presents a comparative bar-plot, showing the results of the friction coefficient measurements conducted at 37° C. for neat HEMA EGDMA 0.1% and HEMA EGDMA 0.1%+MLV DMPC or HSPC at a liposome concentrations of 2 mM and 18 mM;

FIG. 27 presents a comparative bar-plot, showing the results of the friction coefficient measurements conducted at 37° C. for neat HEMA EGDMA 1% and HEMA EGDMA 1%+MLV DMPC or HSPC at a liposome concentrations of 0.4 mM, 2 mM and 18 mM;

FIG. 28 presents a comparative bar-plot, showing the results of the friction coefficient measurements conducted at 37° C. for neat HEMA EGDMA 2% and HEMA EGDMA 2%+MLV DMPC or HSPC at a liposome concentrations of 2 mM and 18 mM;

FIG. 29 presents a comparative bar-plot, showing the results of the friction coefficient measurements conducted at 25° C. for neat HEMA-MA EGDMA 0.75% and HEMA EGDMA 0.75%+MLV DMPC or HSPC at a liposome concentrations of 10-30 mM;

FIG. 30 presents a comparative bar-plot, showing the results of the friction coefficient measurements conducted at 37° C. for neat HEMA EGDMA 0.75% and HEMA-MA EGDMA 0.75%+MLV HSPC at a liposome concentration of 20 mM;

FIG. 31 presents a comparative bar-plot, showing the results of the friction coefficient measurements conducted at 25° C. for HEMA EGDMA 2%+MLV HSPC/Cholesterol, comparing the effect of various cholesterol concentrations of 0%, 10%, 15% and 40%;

FIG. 32 presents a comparative bar-plot, showing the results of the friction coefficient measurements conducted at 25° C. for HEMA EGDMA 2%+MLV DMPC/Cholesterol, comparing the effect of various cholesterol concentrations of 0%, 10%, 15% and 40%;

FIG. 33 presents a comparative bar-plot, showing the results of the friction coefficient measurements conducted at 37° C. for HEMA EGDMA 2%+MLV HSPC/Cholesterol, comparing the effect of various cholesterol concentrations 0%, 10%, 15% and 40%;

FIG. 34 presents a comparative bar-plot, showing the results of the friction coefficient measurements conducted at 37° C. for HEMA EGDMA 2%+MLV DMPC/Cholesterol, comparing the effect of various cholesterol concentrations of 0%, 10%, 15% and 40%;

FIG. 35 presents a comparative bar-plot, showing the results of the friction coefficient measurements conducted at 25° C. for HEMA EGDMA 1%+SUV DPPC containing cholesterol at concentrations of 0%, 5%, 15% and 40%;

FIG. 36 presents a comparative bar-plot, showing the results of the friction coefficient measurements conducted at 25° C. for HEMA EGDMA 2%+SUV DPPC containing cholesterol at concentrations of 0%, 5%, 15% and 40%;

FIG. 37 presents a comparative bar-plot, showing the results of the friction coefficient measurements conducted at 37° C. for HEMA EGDMA 1%+SUV DPPC containing cholesterol at concentrations of 0%, 5%, 15% and 40%; and FIG. 38 presents a comparative bar-plot, showing the results of the friction coefficient measurements conducted at 37° C. for HEMA EGDMA 2%+SUV DPPC containing cholesterol at concentrations of 0%, 5%, 15% and 40%.

DESCRIPTION OF SPECIFIC EMBODIMENTS OF THE INVENTION

The present invention, in some embodiments thereof, relates to material science, and more particularly, but not exclusively, to compositions and method for reducing the friction coefficient of hydrogels or of composite materials comprising a hydrogel, and to uses of such low friction hydrogels or composite materials containing same.

The principles and operation of some embodiments of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have surprisingly uncovered that the incorporation of liposomes in the process of forming hydrogels, results in reduction of the friction coefficient of the hydrogel, compared to the friction coefficient of the equivalent hydrogel not having liposomes dispersed therein.

The present inventors have further identified some parameters of the hydrogel and/or the incorporated liposomes, which lead to enhanced reduction of the friction coefficient of the hydrogel.

As discussed hereinabove, while hydrogels may possess many qualities that render these materials suitable for various applications, such as cartilage replacement, or scaffolds for tissue engineering, their inherent friction coefficient is typically too high and degradation, delamination or other undesirable effects arising from high friction at the hydrogel surface, occur at a high rate and limit their efficiency. Thus, a hydrogel with reduced friction coefficient is of high interest.

As indicated hereinabove, incorporation of liposomes in hydrogels has been generally used heretofore in the context of a matrix, in the form of a hydrogel, for dispensing drug-delivery vehicles, in the form of liposomes, for various medical proposes. These hydrogels, dispensing liposomes for drug-delivery, are typically soft (Young's modulus or shear storage modulus (G') of less than 1000 Pa) and lose their microscopic structure under mild loads.

While conceiving the present invention, the inventors have contemplated using hydrogels, or composite materials containing same, under high loads/pressures conditions, such as apply in skeletal joints. Hydrogels used in such applications should typically exhibit Young's modulus or shear storage modulus (G') of no less than 1000 Pa, and, as discussed hereinabove, are limited by their high friction coefficient. To this end, the present inventors have recognized that reduction of the friction coefficient of the hydrogels is required for effective performance under such conditions and have designed and successfully practiced a methodology for reducing the hydrogel (or composite containing same) friction coefficient by incorporating liposomes within the hydrogel.

While reducing the present invention to practice, hydrogels which exhibit shear storage modulus (G') of 1000 Pa of higher, such as HEMA hydrogels, were prepared while adding liposomes to the hydrogels prior to their curing stage, and were found to exhibit a notable shear reduction, or a notable reduction in their friction coefficient ($\mu$). As demonstrated in the Examples section that follows, the effective friction coefficient measured under high load of 3000 grams for an exemplary poly(2-hydroxyethylmethacrylate) hydrogel crosslinked with 1% ethylene glycol dimethacrylate (referred to hereinbelow as HEMA EG 1%) was reduced by a factor of 30 from 0.2-0.25 to 0.01 when MLV HSPC liposomes at a stock concentration of 45 mM were added prior to the gelation process, both in experiments measuring friction of hydrogel versus hydrogel and in experiments measuring friction of the hydrogel against a round metal object. As further demonstrated in the Examples section that follows, this 30-fold reduction of the friction coefficient may be regarded as a lower bound value, as the neat HEMA hydrogel (not containing liposomes) could not withstand high pressures, and was crushed under high loads (in other words, the reduction in friction coefficient is even greater than the 30-fold indicated).

As further demonstrated in the Examples section that follows, the effective friction coefficient of the hydrogel measured under high loads of maximum of 8000 grams for an exemplary poly(2-hydroxyethylmethacrylate) crosslinked with 4% 9EGDMA (a polyethylene glycol dimethacrylate crosslinking agent having an average molecular weight of 550) (such hydrogel is referred to herein as HEMA 9EGDMA 4%) was reduced by a factor of at least 30 from 0.3 to 0.01 in the hydrogel against metal friction measurements, while the neat hydrogel crushed under such high loads.

While further contemplating various uses and applications of the compositions of the present embodiments, drying and rehydrating the hydrogels was attempted, and the results presented in the Examples section that follows show that the rehydrated liposome-incorporating hydrogels reduced the friction coefficient as efficiently as the liposome-incorporating hydrogels that had not been dehydrated.

The studies of various exemplary hydrogel/liposomes compositions as presented herein led to the identification of several factors which govern the capacity to reduce the friction coefficient of a hydrogel by incorporating liposomes therein. These factors include, without limitation:

The composition of the hydrogel, namely the formulation of the hydrogel-forming agent(s);

The "hardness" of the hydrogel, which may be expressed, for example, by shear storage modulus (G');

The degree of crosslinking of the hydrogel, expressed in molar percent of a crosslinking agent relative to a molar content of the hydrogel-forming agent(s);

The hydration level (water content) of the composition, expressed by the water content of the hydrogel when fully hydrated;

The chemical make-up of the liposomes, expressed inter alia by the molar percent of phosphatidylcholines in the total phospholipids comprising the liposomes, and various additive used in the process of making the liposomes, such as polymers, cholesterol and the likes at various concentrations relative to the total amount of liposome lipids;

The size of the liposomes, expressed in average diameter as measured by, e.g., dynamic light scattering techniques;

The amount/concentration of liposomes in the final fully hydrated composition; and The working temperature at which the composition is subjected to loads and shear forces.

In some of the present embodiments, maximal reduction of the friction coefficient of any given hydrogel can be afforded by selecting optimal values for one or more of the above factors. It is noted herein that for practical considerations, the hydrogel component of the hydrogel/liposomes composition presented herein, should exhibit some capacity to withstand at least some load or force, namely be characterized by a certain degree of "hardness", which can be expressed by a shear storage modulus (G') of at least 1000 Pa.

According to an aspect of embodiments of the present invention, there is provided a composition which includes a hydrogel and a plurality of liposomes incorporated in the hydrogel, wherein the composition is characterized by a shear storage modulus (G') of at least 1000 Pa.

In some embodiments, the liposomes are dispersed throughout the bulk of the hydrogel. In some embodiments, forming the hydrogel in the presence of liposomes results in dispersion of the liposomes within the bulk of the hydrogel.

Hydrogels:

As used herein, the term "hydrogel" refers to a three-dimensional fibrous network containing from about 50%, or from about 80%, and up to 99.9% (by mass) water. A hydrogel can be regarded as a material which is mostly water, yet behaves like a solid or semi-solid due to a three-dimensional crosslinked network within the liquid, made of natural and/or synthetic polymeric chains. According to some embodiments of the present invention, a hydrogel may contain polymeric chains of various lengths and chemical compositions which may stem from monomers, oligomers, block-polymeric units, which are inter-connected (crosslinked) by chemical bonds (covalent, hydrogen and ionic/complex/metallic bonds).

A hydrogel, according to some embodiments of the present invention, may contain macromolecular polymeric and/or fibrous elements which are not chemically connected to the main crosslinked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes. According to some of any of the embodiment of the present invention, the amount of such non-crosslinked additives is small and typically does not exceed 100 mg in 1 ml of the hydrogel-forming precursor solution.

In the context of embodiments of the present invention, when a hydrogel is used in combination with such macromolecular structures, it is referred to interchangeably as "a composite material comprising a hydrogel", "a composite structure comprising a hydrogel", "hydrogel-containing composite material or structure", "hydrogel-containing composite" or simply as "a hydrogel" or as a "composite". Thus, the term "hydrogel" is meant to encompass hydrogel/fiber-network composites wherein a network of intertwined and/or woven fibers is engulfed in a mass of a hydrogel. In general, a composite material comprising a hydrogel may further comprise a woven mesh of fibers, non-woven fibers, a plurality of rods, a net etc. Exemplary hydrogel/fiber-network composites are described, for example, in Moutos et al. Nat. Mater., 2007, 6(2), p. 162-7.

According to some embodiments of the present invention, the hydrogel may contain additional elements which render it useful for specific applications, such as therapeutic and labeling agents, as these are discussed below, scaffold and other structural elements, live cells, cellular components and the like.

Hydrogels may take a physical form that ranges from soft, brittle and weak to hard, elastic and tough material. Soft hydrogels may be characterized by rheological parameters including elastic and viscoelastic parameters, while hard hydrogels are more suitably characterized by tensile strength parameters, elastic, storage and loss moduli, as these terms are known in the art.

The softness/hardness of a hydrogel is governed inter alia by the chemical composition of the polymer chains, the "degree of crosslinking" (number of interconnected links between the chains), the aqueous media content and composition, and temperature. In some embodiments, the hydrogel is reinforced with other fibrous material to form a composite structure, which exhibits high tensile strength compared to a neat hydrogel, as discussed hereinabove for a composite material containing a hydrogel. In some embodiments of the present invention, the hardness of the neat hydrogel is similar to the hardness of the hydrogel/liposomes compositions, meaning that the inclusion of liposomes in the bulk of the hydrogel does not affect the hardness values significantly, or lower/augment it mildly. It is noted herein that since the inclusion of liposomes reduces the friction coefficient of the hydrogel, the hydrogel is able to sustain the loads and forces applied thereon during the measurements of tensile moduli, hence in some cases the tensile strength expressed in storage modulus G' appears to change from neat to liposome incorporation.

In some cases, the ability to form crosslinks between the polymeric chains during the curing of a hydrogel, is an intrinsic property of the hydrogel-forming agent, namely the hydrogel-forming agent exhibits "crosslinkable functional groups" that can form bonds therebetween under certain conditions (initiation or activation), thereby form crosslinking bonds between the polymers making the hydrogel. Crosslinkable functional groups can be introduced into a polymeric chain by including a certain amount of certain crosslinkable monomers in the total amount of monomers that form the polymeric chain, wherein those crosslinkable monomers are characterized by having at least three functionalities, at least one of these is a crosslinkable functional group which can form bonds with other crosslinkable functional groups on other polymeric chains during or after the polymerization process. In such an example, a growing polymeric chain will exhibit a crosslinkable functional group along its chain at a certain frequency that corresponds to the relative concentration of the crosslinkable monomer in the pre-polymerization formulation (percentage).

Exemplary crosslinkable monomers include, without limitation, the family of di- and triacrylates monomers, which have three polymerizable functionalities, one of which can be regarded as a crosslinkable functional group. Diacrylates monomers include, without limitation, methylene diacrylate, and the family of poly(ethylene glycol)$_n$ dimethacrylate (nEGDMA), Triacrylates monomers include, without limitation, trimethylolpropane triacrylate, pentaerythritol triacrylate, tris (2-hydroxy ethyl) isocyanurate triacrylate, isocyanuric acid tris(2-acryloyloxyethyl) ester, ethoxylated trimethylolpropane triacrylate, pentaerythrityl triacrylate and glycerol triacrylate, phosphinylidynetris(oxyethylene) triacrylate.

In another example, certain functional groups present at a certain frequency in a pre-formed polymer, can be converted into crosslinkable functional groups by a variety of chemical modifications. For example, an amino group of a side-chain in a polymer, such as a polypeptide, can be converted into a crosslinkable functional group by coupling the amino group with an acrylate to thereby form an acrylate functional group along the polymeric chain that can form crosslinks with similar acrylate functionalities on other polymeric chains.

In the context of some embodiments of the present invention, since a crosslinking agent per-se is not used in the crosslinking (curing) process of hydrogel-forming agents having crosslinkable functional groups incorporated therein, the number of such crosslinkable functional groups, relative to the total number of monomers in the hydrogel-forming agent, can be correlated to the degree of crosslinking in such hydrogels.

For example, in the case of gelatin methacrylate, the degree of methacrylation can be correlated to the degree of crosslinking, considering that 3.5% of the polymeric units (monomers) of gelatin can potentially undergo methacrylation (the frequency of the crosslinkable monomers within the polymer), that only a certain percent of these units (crosslinkable monomers) actually undergo methacrylation, and that each two methacrylated units form a single crosslinking bridge. In one example, if 75% of these units undergo methacrylation, and every two methacrylic moieties form one crosslinking bond, the molar percent of a crosslinking agent to hydrogel-forming agent in the case of gelatin methacrylate-based hydrogels is about 3.5%*0.75/2=1.3%. A similar calculation applies to other hydrogel-forming agents having crosslinkable functional groups as part of their chemical structure.

As the hardness of the hydrogel is correlated to the degree of crosslinking, one way to signify the hydrogel hardness is by denoting the amount of the crosslinking agent used in its preparation. Ultimately, hydrogels' hardness is measured by standard elastic, storage and loss moduli.

According to some of any of the embodiments of the present invention, the hydrogel/liposomes compositions presented herein are based on a hydrogel which is characterized by a storage modulus is 1000 Pa or higher in its neat form (without liposomes and/or additional components which form a composite as described herein). In some embodiments, the storage modulus of the hydrogel without liposomes is greater than 2000 Pa, greater than 3000 Pa, greater than 4000 Pa, greater than 5000 Pa, greater than 7 KPa, greater than 10 KPa or greater than 20 KPa.

According to some of any of the embodiments of the present invention, the hydrogel/liposomes compositions presented herein are based on a hydrogel-containing composite which is characterized by a storage modulus higher than 1000 Pa (without liposomes). In some embodiments, the storage modulus of the hydrogel-containing composite without liposomes is greater than 2000 Pa, greater than 3000 Pa, greater than 4000 Pa, greater than 5000 Pa, greater than 7 KPa, greater than 10 KPa or greater than 20 KPa.

As can be appreciated, these hydrogels or composite materials containing same are capable of preserving their structural integrity under considerable loads, while softer hydrogels tear and squeeze out under similar loads.

Hydrogels are formed from hydrogel-forming agents in the presence of a crosslinking agent and other optional components. Hence, according to embodiments of the present invention, a hydrogel may be defined by its chemical composition, namely the type of the hydrogel-forming agent and the type (and amount) of the crosslinking agent.

Hydrogel-forming agents include, for example, polymerizable monomers, a mixture of different polymerizable monomers, a mixture of monomers, oligomers, block polymers, short and long polymeric chains (polymers) and any combination thereof.

Non-limiting examples of hydrogel-forming agents, which can be used in some of any the embodiment of the present invention, include hydroxyethyl methacrylate (HEMA), hydroxyethyl acrylate (HEA), acrylamide (AAm), methacrylamide (MAAm), acrylic acid (AAc), methacrylic acid (MAAc), hydroxyethyl acrylate (HEA), hexyl methacrylate, N-isopropylacrylamide (NiPAAm)), N-isopropylmethacrylamide, polylactic acid, polyamide, polyethyleneterephthalate (PET), polyvinyl alcohol, polyurethane, polycaprolactone, polyethylene glycol (also known as polyethylene oxide, PEG or PEO), N,N-dimethacrylamide (nnDMAA), hyaluronic acid (HA), HA methacrylate, polycaprolactone, peptides, saccharides, gelatin, gelatin methacrylate, chitosan, chitosan methacrylate, glycol chitosan, glycol chitosan methacrylate, alginate, alginate methacrylate, cellulose, siloxanes, polysiloxanes, and any oligomer and polymer thereof, in any combination thereof.

According to some embodiments of the present invention, the water content of a fully hydrated hydrogel ranges from 50% to 99.9%, or from 70% to 99.9%, or from 80% to 99.9%, or from 90 to 99.9%, or from 90 to 99%, including any range or value therebetween, by weight of the total weight of the hydrogel/liposomes composition presented herein.

Crosslinking:

When the term "crosslinking" is used in the context of hydrogels, it usually refers to the use of crosslinking agents, as defined herein, to promote a difference in the polymer composition's physical properties. The "degree of crosslinking" can be correlated to mechanical parameters which can be measured by several experimental methods, including modulus and swelling measurements. These measurements can correlate the "molar percent of a crosslinking agent to hydrogel-forming agent" to various chemical and mechanical parameters that characterize a hydrogel. These parameters include, for example, the degree of swelling, the polymer volume fraction in the hydrogel, the crosslink density (mol/cm$^3$), the network chain density (mol/cm$^3$) and the network chain molecular weight (gram/mol).

As used herein, the phrase "crosslinking agent" refers to a substance that promotes or regulates intermolecular covalent, ionic, hydrogen or other form of bonding between polymeric chains, linking them together to create a network of polymeric chains which result in increasing the rigidity of the structure. Crosslinking agents typically exhibit one or more, preferably two or more, bonding functionalities, for example, two double (vinyl) bonds (a functionality of four, or tetrafunctionality), three amines (a functionality of three, or trifunctionality), creating chemical bonds between two or more polymer chains.

Comonomers constitute a type of crosslinking agents which are contemplated in some embodiments of the present invention. A comonomer is a monomer having at least three bonding functionalities (trifunctionality), which is incorporated into the backbone of a growing polymer in the course of the polymerization/gelation process. While two of its functionalities are used to form the polymeric backbone, the third (and more) functionality is free to form crosslinks with counterparts in other polymeric chains. In general, comonomers are used to generate crosslinking homogeneously along the polymeric chain. It is noted herein that the term "comonomer" is meant to encompass oligomers and short polymers, having at least three bonding functionalities, which can be incorporated into a growing polymer during the polymerization process.

In general, the crosslinking agent is selected according to the chemistry and polymerizing conditions used to form the polymeric backbone of the hydrogel. Non-limiting examples of crosslinking agents, according to some embodiments of the present invention, include ethylene glycol dimethylacrylate (EGDMA), poly(ethylene glycol) dimethacrylate (also known as polyethyleneoxide dimethacrylate, poly-EGDMA, nEGDMA or PEOdMA), N,N'-methylenebisacrylamide (MBA or MBAm), N,N'-methylenebis(2-methylacrylamide), methylene diacrylate, methylene bis(2-methylacrylate), diethylene glycol diacrylate, hexamethylene diacrylate, oxybis(methylene) bis(2-methylacrylate), oxybis(ethane-2,1-diyl) bis(2-methylacrylate), and glutaraldehyde.

As discussed hereinabove, the degree of crosslinking of a hydrogel can be expressed in terms of the amount of crosslinking agent used in the making thereof. This value is typically given in molar percent of a crosslinking agent to hydrogel-forming agent(s). This value corresponds roughly with the number of crosslinks per polymer chain length, as each crosslinking agent residue forms one crosslink in the network. Determining this value is based on the percentage of the molar content of the crosslinking agent(s) to the molar content of all hydrogel-forming agents which form chemical bonds that are part of the polymeric chains that make the hydrogel network.

In some embodiments wherein the hydrogel-forming agent exhibits crosslinkable functional groups which form the crosslinking bonds directly therebetween without a crosslinking agent per-se, the number of these crosslinkable functional groups is related to the amount of crosslinking agent such that two crosslinkable functional groups are counted as one crosslinking agent molecule. In terms of molar content and relative percentage, the value given for the degree of crosslinking is therefore half of the frequency of the monomers exhibiting crosslinkable functional groups out of the total number of monomers in the hydrogel-forming agent.

Other molecules that may form other type of non-chemical interactions, such as entanglement, are not taken into account. For example EGDMA 1% means 0.01 mol of EGDMA to every 1 mol of HEMA monomers.

Thus, the hydrogel component of the hydrogel/liposomes composition, according to some embodiments of the present invention, can be characterized by the molar percent of the crosslinking agent used in its preparation, a measure that typically correlates with the degree of crosslinking. In the context of some embodiment of the present invention, the degree of crosslinking is defined as the molar ratio in percents, or molar percentage, of the crosslinking agent relative to the hydrogel-forming agent(s). In other words, in cases where the molar amount of hydrogel-forming agent is 100 and the molar amount of the crosslinking agent is 2, the degree of crosslinking is 2%. According to some of any of the embodiments of the present invention, the molar percentage of the crosslinking agent ranges from 0.00001% to 50% per hydrogel-forming agent's total molar content. In some embodiments, the range of molar percentage of the crosslinking agent ranges from 0.01% to 25%, from 0.2% to 25%, from 1% to 20% or from 1% to 15%, including any subranges and intermediate values therebetween.

According to some of any of the embodiments described herein, various ranges and subranges of the molar percentage of the crosslinking agent are used in combination with various hydrogels, various liposome sizes, various liposome concentrations, and various other parameters, as these are defined herein, and embodiments of the present invention encompass all of such combination. In some embodiments, the degree of crosslinking is selected according to a the hydrogel type, liposome size, liposome concentration and/or other parameters, in various combinations, to maximize the capacity to reduce the friction coefficient of any given hydrogel by incorporating liposomes therein.

As demonstrated in the Examples section that follows, the molar percent of the crosslinking agent correlates to the size and concentration of the liposomes, namely there are specific combinations of these parameters (hydrogel crosslinking, liposome size and liposome concentration) that confer a greater reduction in friction coefficient than other combinations. For example, one sub-range of crosslinking of 0.00001% to 0.2% may correspond to liposomes having an average diameter (D) of more than 100 nm, while another sub-range of crosslinking of 0.21% to 25% may correspond to liposomes having D larger than 80 nm and a concentration 5 mM or higher.

In some of embodiments of the present invention, as described hereinbelow, the degree of crosslinking of the hydrogel is 0.2 molar percent or higher.

In some embodiments of the present invention, as described hereinbelow, the degree of crosslinking of the hydrogel is 0.2 molar percent or lower.

Liposomes:

Pristine hydrogels not having liposomes incorporated therein, also referred to herein as "neat" hydrogels, typically have a friction coefficient ($\mu$) in aqueous conditions in the range of 0.5-1 (e.g., for HEMA-based hydrogels). These values indicate that neat hydrogels, used under some load in an aqueous environment, are not suitable for applications requiring much lower friction under load. When liposomes are incorporated therein, according to the present embodiments, these values of the friction coefficient drop down by a factor of up to 60 and even more.

In the context of some embodiments of the present invention, liposomes are artificial vesicles composed of a substantially spherical lipid bilayer which typically comprises phospholipids, cholesterol and other lipids. Main liposome types include small unilamellar vesicles (SUV)

which typically exhibit an average diameter under 100 nm, large unilamellar vesicle (LUV) which typically exhibit an average diameter larger than 100 nm, and multilamellar vesicle (MLV) which typically exhibit an average diameter that may range from about 80 or about 100 nm to 1 μm and larger. In the context of some embodiments of the present invention, SUV liposomes have an average diameter of 80 nm or lower, and MLV liposomes have an average diameter higher than 80 nm.

It is noted that the use of liposome aqueous suspensions as lubricants is not equivalent to lowering the friction coefficient of a hydrogel by incorporating liposomes therein, since a hydrogel having a low friction coefficient may not need lubrication; namely a lubricant is not equivalent to a material having a low friction coefficient. Without being bound by any particular theory, it is noted herein that the use of liposomes dispersed in a hydrogel rather than the use of liposome in liquid suspension applied to the surface of a hydrogel, is advantageous, as it provides a reservoir of liposomes within the hydrogel that result in a self-healing action when wear occurs at the hydrogel surface. Thus, for example, a low friction coefficient of the hydrogel is maintained for extended periods while the liposomes applied from dispersion on a hydrogel's surface may lose their friction reduction property as soon as the dispersion is removed.

Without being bound to any particular theory, it is suggested that the micro-structural effect of incorporation of liposomes in a hydrogel can result in the distribution of the liposomes throughout the bulk of the hydrogel, or in other words, results in dispersion of liposomes in the hydrogel.

Figure 2A:
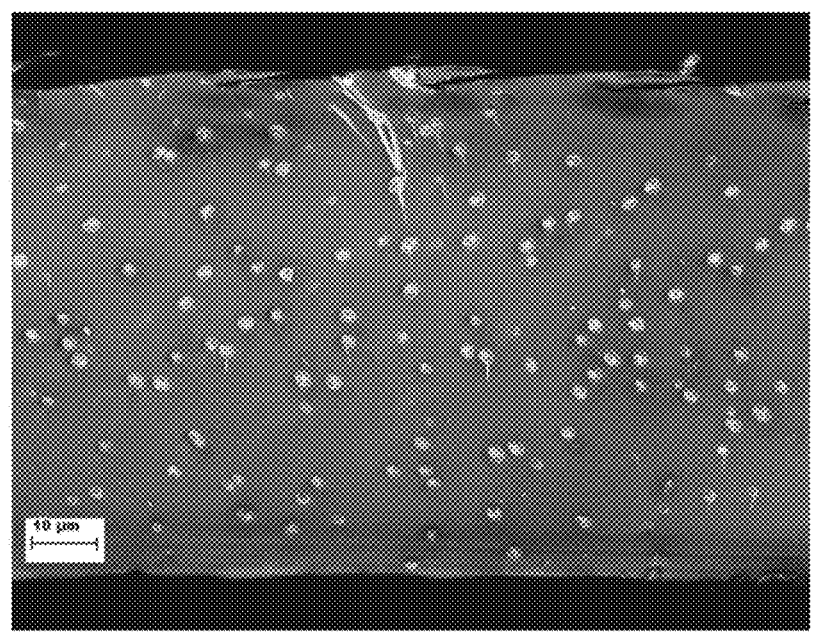
FIGS. 2A-C present electro-micrographs of a fractured sample of HEMA 9EGDMA 4% SUV DMPC hydrogel containing liposomes, taken at a magnification of 2000 (FIG. 2A), a magnification of 24,000 (FIG. 2B) and a magnification of 60,000 (FIG. 2C)
Figure 2B:
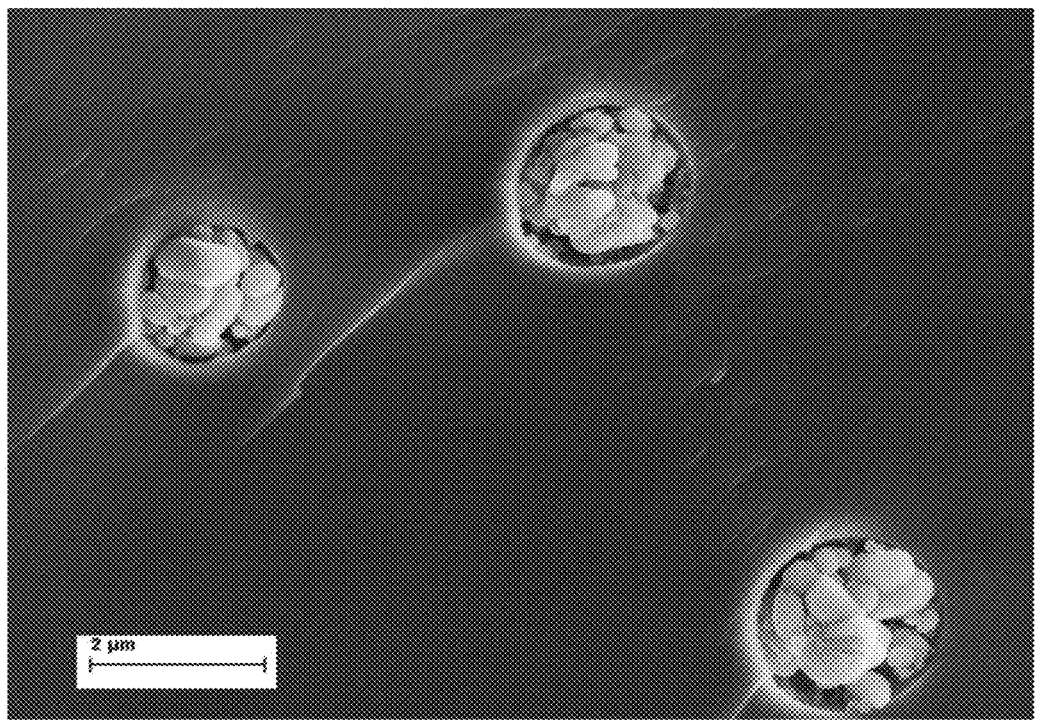
Figure 2C:
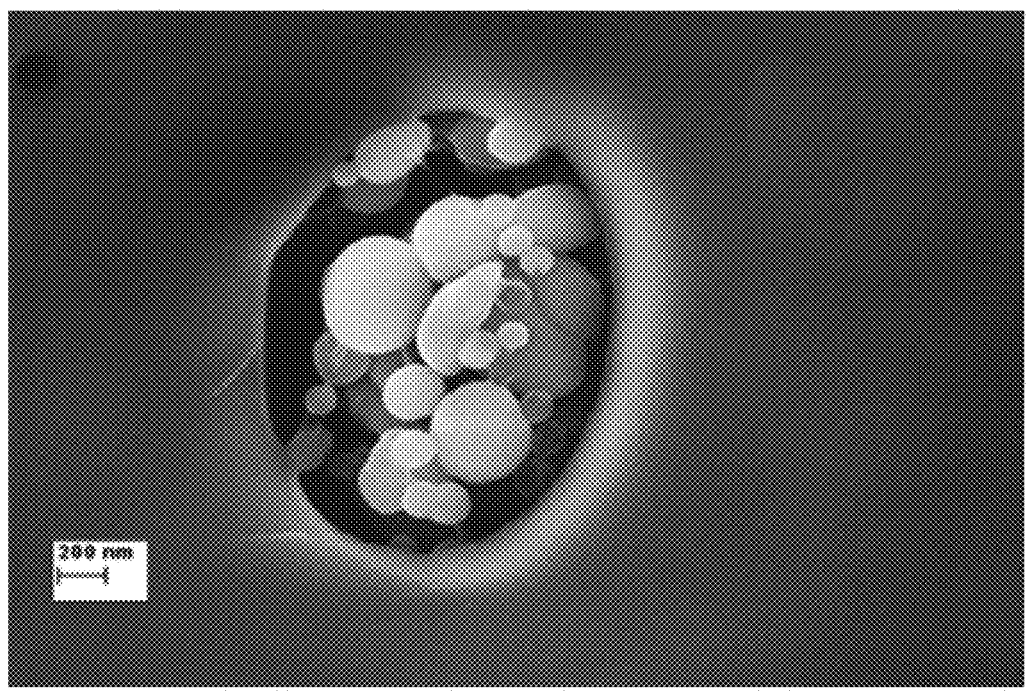

In some embodiments of the present invention, the liposomes are distributed in the hydrogel substantially uniformly in a single liposome form or in the form of clusters of liposomes, as seen in exemplary hydrogel/liposomes compositions and presented in the Examples section that follows (see, FIGS. 2A-C). Depending on the size and concentration of the liposomes, such clusters may range from about 0.5 μm to 5 μm in diameter. Another way to consider the formation of clusters of liposomes in the bulk of the hydrogel, without being bound to any particular theory, is to regard this phenomenon as the formation of pores, voids or pockets full of liposomes, being 0.5 μm to 5 μm in diameter, which are distributed throughout the bulk of the hydrogel/liposome composition (see, FIGS. 2A-C).

It is noted that in general, liposomes having a small diameter have a high radius of curvature that confers an asymmetric distribution of the bilayer constituents. Furthermore, small liposomes are limited in terms of the encapsulation of aqueous space per mole of lipid. Hence, liposomes having a small diameter may exhibit a less stable spherical structure. Relatively unstable liposomes May be disadvantageous, especially while applying high loads and shearing the hydrogel with its liposome composition, or may be advantageous, in embodiments where liposome breakdown is desirable.

According to some of any of the embodiments of the present invention, the liposomes dispersed throughout the bulk of the hydrogel are greater than 80 nm in diameter. Alternatively, the liposomes dispersed throughout the bulk of the hydrogel, according to some embodiments of the present invention, are greater than 20 nm, greater than 30 nm, greater than 40 nm, greater than 50 nm, greater than 60 nm, greater than 70 nm, greater than 80 nm, greater than 90 nm, greater than 100 nm, greater than 150 nm, greater than 200 nm, greater than 250 nm, greater than 300 nm, greater than 400 nm, greater than 500 nm, greater than 600 nm, greater than 700 nm or greater than 900 nm in diameter.

It is noted herein that liposomes are prone to swelling and growth, and also tend to form aggregates, change from SUV to MLV and form cochleates and other super-structures such as bicontinuous structures. This instability, mostly observed in SUV of diameters smaller than 80 nm, should be considered when designing a hydrogel encapsulating the same. Liposomes of 80 nm in diameter or less may require stabilization which may be achieved with the use of various agents, as described hereinafter. Liposomes of 80 nm in diameter or less may be practical for use in some embodiments of the present invention, under certain stabilizing conditions and s hydrogel parameters, to lower the friction coefficient of hydrogels.

The size of the liposomes stated herein and throughout refers to the size which has been measured shortly before gelation and incorporation of the liposomes in the hydrogel's network. It is also noted that comparing the light scattering size of the liposomes prior to incorporation in the hydrogels with electron-microscopy measurements using fracture techniques indicates that the liposomes do not change their size once entrapped in the hydrogel's network.

Phosphatidylcholines constitute a class of phospholipids that incorporate phosphocholine as a head-group. Without being bound by any particular theory, it is assumed that the phosphocholine moiety confers the high hydration state of liposomes which directly or indirectly affect the capacity to lubricate surfaces and lower the friction coefficient of the hydrogels/liposomes compositions presented herein.

According to some of any of the embodiment of the preset invention, the liposomes that are incorporated into hydrogels are comprised of at least one phosphatidylcholine phospholipid. According to some embodiment of the preset invention, the liposomes are composed of at least 50 molar percent phosphatidylcholine phospholipids out of the total lipid composition of the liposome. In some embodiments, the phosphatidylcholine phospholipid content in the liposomes is 20 molar percent, at least, at least 30 molar percent, at least 40 molar percent, at least 60 molar percent, at least 70 molar percent, at least 80 molar percent, at least 90 molar percent, or 100 molar percent of the total lipid composition of the liposome. In some embodiments, the phospholipid consists essentially of at least one phosphatidylcholine.

In some embodiments of any one of the embodiments described herein, the amphiphilic lipid described herein (e.g., in liposomes described herein) is characterized by a molar percentage of phosphatidylcholine (the at least one phosphatidylcholine described herein) in the total amount of lipids making the liposome, which is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the amphiphilic lipid consists essentially of at least one phosphatidylcholine.

The fatty acyl groups in a lipid described herein may comprise saturated fatty acyl groups, monounsaturated fatty acyl groups (having a single unsaturated bond) and/or polyunsaturated fatty acyl groups (having two or more unsaturated bonds). In some embodiments, the unsaturated bonds are cis double bonds.

Examples of suitable saturated fatty acyl groups include, without limitation, lauroyl, myristoyl, palmitoyl and stearoyl.

Examples of suitable monounsaturated fatty acyl groups include, without limitation, oleoyl, palmitoleyl, eicosenoyl, erucoyl, nervonoyl and vaccenoyl.

Examples of suitable polyunsaturated fatty acyl groups include, without limitation, linoleoyl, α-linolenoyl, γ-linolenoyl, dihomo-γ-linolenoyl, stearidonoyl, eicosatraenoyl, eicosapentaenoyl, docosapentaenyl, docosahexaenoyl, arachidonoyl and adrenoyl.

In some embodiments of any one of the embodiments described herein, the fatty acyl groups are selected from the group consisting of saturated and monounsaturated fatty acyl groups. In some embodiments, the fatty acyl groups are saturated fatty acyl groups.

Without being bound by any particular theory, it is believed that saturated and monounsaturated fatty acyl groups, particularly saturated fatty acyl groups, are relatively resistant to chemical reaction such as oxidation, and therefore provide a more resilient system.

In some embodiments of any one of the embodiments described herein, at least 50% of the fatty acyl groups are the same species of fatty acyl group (e.g., myristoyl, palmitoyl). In some embodiments, at least 75% of the fatty acyl groups are the same species of fatty acyl group. In some embodiments, at least 90% of the fatty acyl groups are the same species of fatty acyl group.

Exemplary phospholipids comprising a single species of fatty acyl group include 1,2-dimyristoyl-sn-glycero-3-phosphocholine and 1,2-dipalmitoyl-sn-glycero-3-phosphocholine.

According to some of any embodiment of the present invention, the phosphatidylcholine is selected from the group consisting of 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), hydrogenated soybean phosphocholine (HSPC) and 1,2-distearoyl-sn-glycero-3-phosphocholine (DSPC), and any combination thereof.

According to embodiments of the present invention, the concentration of the liposomes in the hydrogel-forming composition is at least 1 mM, at least 2 mM, at least 4 mM, at least 6 mM, at least 10 mM, at least 12 mM, at least 16 mM, at least 20 mM, at least 24 mM, at least 30 mM, at least 35 mM, at least 40 mM, at least 60 mM, at least 100 mM or at least 200 mM, including any intermediate values and including any subranges within 1 mM to 200 mM. Higher concentrations are also contemplated.

According to some embodiments of the present invention, the concentration of the liposomes in the hydrogel-forming composition is higher than 4 mM, or is 4 mM or lower, depending on other various parameters of the hydrogel, as described in further detail hereinunder.

According to some of any of the embodiments of the present invention, the liposomes encapsulate or incorporate into their lipid bilayer, or, are used in combination with, an additional active agent. The additional agent can be used in the preparation of the liposomes, and such additional agents, in some embodiments, can be a polymer, cholesterol, a liposome-stabilizing agent and/or an active agent, while an active agent can be a labeling agent, a bioactive agent or a therapeutically active agent. In some cases, the additional agent can serve one, two or all three of the above functions.

Liposomes can be prepared such that the lipid bilayer comprises stabilizing components, surface-altering components and structure-altering components. Furthermore, liposomes can encapsulate various factors, solutes, compounds, macromolecules, viral components, viruses, genetic-coding materials, drugs and many other chemical entities. Such chemical entities, whether incorporated into the lipid bilayer or encapsulated within the liposome, may affect the structure of the liposome in terms of its size and stability, may affect the reactivity of the liposome towards other chemical entries, and affect its capacity to lower the friction coefficient of a hydrogel in-which it is dispersed.

As observed by the present inventors, adding liposome-stabilizing agents, such as cholesterol, glucosamine, polycaprolactone, dextrose and other sugars, or polymers such as hyaluronan (hyaluronic acid or hyaluronate or HA), chitosan, chitosan methacrylate, glycol chitosan, glycol chitosan methacrylate, or alginate to the preparation of the liposomes, allows the hydrogel/liposomes compositions presented herein to sustain the low friction coefficient under larger loads compared to similar compositions wherein the liposomes did not contain the stabilizing component. It is noted that adding polymers which are not part of the crosslinked network of the hydrogel, can be effected at the liposome preparation process or at the hydrogel solution preparation process, prior to initiation of the crosslinking process and the curing step.

According to some of any of the embodiment of the present invention, the liposomes which are incorporated (encapsulated) in the hydrogel, are prepared in the presence of a polymer, a hydrogel-forming polymer and/or liposome-stabilizing agent. In some of these embodiments, the additional agent is a polymer, as described hereinabove. Non-limiting examples of polymers which can be used in this context of the present invention, include polycaprolactone, poly(2-hydroxyethyl methacrylate) (pHEMA), alginate and hyaluronic acid (HA). In some embodiments, the concentration of the liposome-stabilizing polymer in the liposome preparation solution ranges from 0.1 mg polymer per 1 ml of liposome suspension solution to 5 mg/ml.

According to some of any of the embodiment of the present invention, the liposomes which are incorporated (encapsulated) in the hydrogel, are prepared while including cholesterol in the lipid formulation of the liposomes. In some embodiments, the concentration of cholesterol in the liposome preparation solution ranges from 1% (molar percent) to 50%, relative to the total amount of lipids in the liposome preparation solution. In some embodiments, the concentration of cholesterol ranges from 1% to 40%, 1% to 30%, 1% to 20%, 1% to 15%, 1% to 10% or 1% to 5% and all the possible subranges as well as individual numerical values within that range. According to some embodiments of any embodiment of the present invention, the concentration of cholesterol ranges from 1% to 10% (molar percents). In some embodiments, the concentration of cholesterol in the liposome is lower than 50% (molar percents).

The liposomes in the hydrogel/liposomes compositions presented herein may also be used as drug-delivery vehicles, as this concept is known in the art. According to some of any of the embodiments of the present invention, the liposomes as described herein encapsulate at least one additional active agent such as a labeling agent, a therapeutically active agent and/or bioactive agent, as these terms are defined herein.

The encapsulation or the incorporation into the bilayer of an additional active agent in the liposomes dispersed in the compositions of the present embodiments can provide a dual utility for the composition. For example, when the composition is utilized in an implantable device such as a joint replacement device, the additional active agent may be a labeling agent, and the gradual release thereof to the biologic environment where the device is implanted can assist in diagnosing the function of the device. Alternatively, the additional active agent is a therapeutically active agent that can be beneficially released into the environment, thereby enhancing the function of the device as a drug-delivery device. Additional description of some of these embodiments is provided hereinunder.

As used herein, the phrase "a therapeutically active agent" describes a chemical substance, which exhibit a therapeutic activity when administered to a subject.

As used herein, the phrase "biologically active agent", or "bioactive agent", describes a chemical substance, which exhibits a biological or physiological activity in an organism.

As used herein, the phrase "labeling agent" refers to a detectable moiety or a probe and includes, for example, chromophores, fluorescent compounds, phosphorescent compounds, heavy metal clusters, and radioactive labeling compounds, as well as any other known detectable moieties.

Non-limiting examples of therapeutically active agents that can be beneficially used in embodiments of the present invention include, without limitation, one or more of an agonist agent, an amino acid agent, an analgesic agent, an antagonist agent, an antibiotic agent, an antibody agent, an antidepressant agent, an antigen agent, an anti-histamine agent, an anti-hypertensive agent, an anti-inflammatory drug, an anti-metabolic agent, an antimicrobial agent, an antioxidant agent, an anti-proliferative drug, an antisense agent, a chemotherapeutic drug, a co-factor, a cytokine, a drug, an enzyme, a growth factor, a heparin, a hormone, an immunoglobulin, an inhibitor, a ligand, a nucleic acid, an oligonucleotide, a peptide, a phospholipid, a prostaglandin, a protein, a toxin, a vitamin and any combination thereof.

The combined friction reduction and therapeutic effect is particularly advantageous when the hydrogel/liposomes composition is used in an application that also requires a localized enhanced effect of a therapeutically active agent, such as antimicrobial control, cell/tissue growth, regeneration and necrosis, vasodilatation/vasoconstriction, immunosuppression/immune-enhancement and the likes. Additional description of some of these embodiments is provided hereinunder.

In some of any of the embodiments of the present invention, the therapeutic agent also may comprise a vasodilator to counteract vasospasm, for example an antispasmodic agent such as papaverine. The therapeutic agent may be a vasoactive agent, generally such as calcium antagonists, or alpha and beta adrenergic agonists or antagonists. In some of any of the embodiments of the present invention, the therapeutic agent may include a biological adhesive such as medical grade cyanoacrylate adhesive or fibrin glue, the latter being used to, for example, adhere an occluding flap of tissue in a coronary artery to the wall, or for a similar purpose.

In some of any of the embodiments of the present invention, the therapeutic agent may be an antibiotic agent that may be released from the hydrogel, optionally in conjunction with a controlled release carrier for persistence, to an infected organ or tissue or any other source of localized infection within the body. Similarly, the therapeutic agent may comprise steroids for the purpose of suppressing inflammation or for other reasons in a bodily site. Exemplary anti-infective agents include, for example, chlorhexidine which is added for improved biocompatibility of articles-of-manufacturing comprising the hydrogels according to some of any of the embodiments of the present invention.

Friction Coefficient of Hydrogel/Liposomes Compositions:

As demonstrated in the Examples section below, incorporation of liposomes into the bulk of hydrogels affords hydrogels which are characterized by a dynamic friction coefficient in aqueous media that ranges from 0.001 to 0.08 under a pressure of at least 1 atmosphere. These values are not only low in comparison to neat hydrogels, but are notably low in absolute terms even in comparison to lubricated systems in aqueous media.

Unless stated otherwise, the friction coefficient values presented in the Examples section that follows below and referred to hereinthroughout, refer to dynamic friction coefficient, however, the general propensity to lower the friction coefficient of hydrogels is evident in both static and dynamic friction coefficients.

In some embodiments of the present invention, the friction coefficient of a hydrogel/liposomes composition, is at least 2-fold lower or at least 3-fold lower than the friction coefficient of the corresponding neat hydrogel, or at least 5-fold lower, at least 6-fold lower, at least 7-fold lower, at least 8-fold lower, at least 9-fold lower, at least 10-fold lower, at least 12-fold lower, at least 14-fold lower, at least 16-fold lower, at least 18-fold lower, at least 20-fold lower, at least 25-fold lower, at least 30-fold lower, at least 35-fold lower, at least 40-fold lower, at least 50-fold lower, or at least 60-fold or more lower than the friction coefficient of the corresponding neat hydrogel.

As presented in the Examples section below, it has been demonstrated that certain combinations of the size of the liposomes, concentration of the liposomes and the degree of crosslinking of the hydrogel, stand as conferring an highly efficient reduction in the friction coefficient of the composition compared to the neat hydrogel.

Small liposomes, according to embodiments of the present invention, are liposomes of less than 80 nm in diameter. Accordingly, large liposomes have a diameter larger than 80 nm.

According to embodiments of the present invention, a degree of crosslinking lower than 0.2% is regarded as a low degree of crosslinking (low crosslinking), while a degree of crosslinking larger than 0.2% is regarded as a high degree of crosslinking (high crosslinking).

A liposome concentration 4 mM or lower is regarded as a low concentration, according to embodiments of the present invention, while a high concentration of liposomes is higher than 4 mM.

i. The following lists some combinations of parameters, characterizing and defining various hydrogel/liposomes compositions, according to some embodiments of the present invention, per the above definitions:

ii. Small liposomes, low degree of crosslinking and low liposome concentration;

iii. Large liposomes, low degree of crosslinking and low liposome concentration;

iv. Small liposomes, high degree of crosslinking and low liposome concentration;

v. Large liposomes, high degree of crosslinking and low liposome concentration;

vi. Small liposomes, low degree of crosslinking and high liposome concentration;

vii. Large liposomes, low degree of crosslinking and high liposome concentration;

viii. Small liposomes, high degree of crosslinking and high liposome concentration; and ix. Large liposomes, high degree of crosslinking and high liposome concentration;

Each of the combinations i-viii can be represented by specific parameters. Following are a few examples: The composition presented herein may be characterized by an average diameter of liposomes larger than 80 nm and/or a degree of crosslinking higher than 0.2 molar percent, and a concentration of liposomes higher than 4 mM. The composition presented herein may be characterized by an average diameter of liposomes larger than 80 nm, and a degree of crosslinking higher than 0.2 molar percent. The composition presented herein may be characterized by an average diameter of liposomes larger than 80 nm, and a degree of crosslinking 0.2 molar percent or lower. The composition presented herein may be characterized by an average diameter of liposomes larger than 80 nm, a degree of crosslinking higher than 0.2 molar percent, and a concentration of liposomes higher than 4 mM. The composition presented herein may be characterized by an average diameter of liposomes larger than 80 nm, a degree of crosslinking 0.2 molar percent or lower, and a concentration of liposomes higher than 4 mM. The composition presented herein may be characterized by an average diameter of liposomes larger than 80 nm, a degree of crosslinking higher than 0.2 molar percent, and a concentration of liposomes 4 mM or lower. The composition presented herein may be characterized by an average diameter of liposomes larger than 80 nm, a degree of crosslinking of 0.2 molar percent or lower, and a concentration of liposomes of 4 mM or lower.

In some embodiments, the low friction coefficient of the hydrogel/liposomes compositions presented herein is maintained under a wide range of loads and in various surface-to-surface combinations, including a gel-to-gel configuration and a gel-to-metal configuration, as these are described in detail in the Examples section hereinbelow.

For example, in a gel-to-gel configuration, wherein the hydrogel/liposomes compositions sample is a round shape having a diameter of about 6 mm, a load of about 300 grams corresponds to 1 atmosphere pressure pushing the samples towards one-another. In a gel-to-metal configuration, 1 atmosphere corresponds to a load of about 100 grams pushing a round metal head having a radius of 28 mm into the hydrogel surface.

The reduction in friction coefficient and the durability of these compositions under continuous sliding motion under loads is maintained at various temperatures and for extended duration of time. In some embodiments, the friction coefficient of the hydrogel/liposomes compositions presented herein, is substantially maintained at room temperature (e.g., 25° C.). In some embodiments, the friction coefficient of the hydrogel/liposomes compositions presented herein, is substantially maintained at a physiological temperature (e.g., 37° C.). In some embodiments, the friction coefficient of the hydrogel/liposomes compositions presented herein, is substantially maintained at room temperature as well as at 37° C. In some embodiments, the friction coefficient of the hydrogel/liposomes compositions presented herein, is maintained for at least 300 cycles while experiencing an essentially constant motion under load at room temperature and/or at 37° C.

The reduction in friction coefficient is maintained even after the hydrogel/liposomes composition has been dehydrated. This observation, discussed and presented in the Examples section below, is non-trivial for several reasons, including the fact that liposomes are known to lose integrity once dried, and therefore it would have been expected that the capacity to lower the friction coefficient would be lost once dehydrated. Nonetheless, dehydrated hydrogel/liposomes compositions regained their low friction coefficients once rehydrated. Thus, according to some embodiments of the present invention, the low friction coefficient of the hydrogel/liposomes compositions presented herein, is substantially maintained after at least one dehydration-rehydration cycle.

Method of Lowering the Friction Coefficient of a Hydrogel:

According to another aspect of some embodiments of the present invention, there is provided a method of lowering the friction coefficient of any given hydrogel, as this term is defined and exemplified hereinabove, which is effected essentially by forming the hydrogel in the presence of a plurality of liposomes such that the liposomes are dispersed throughout the bulk of the hydrogel, thereby lowering the friction coefficient of the resulting composition compared to the friction coefficient of the neat hydrogel (not having liposomes dispersed therein).

It should be noted that the capacity to lower the friction coefficient of any given hydrogel is based on the premise that the neat hydrogel is such that the notion of having a friction coefficient is relevant thereto, namely that the neat hydrogel is hard enough to allow its friction coefficient to be measured or assessed by conventional means.

According to some embodiments of the present invention, this method is applied to hydrogels or composite materials containing a hydrogel, which are characterized by a shear storage modulus (G') of at least 1000 Pa.

In some embodiments, the method of incorporating liposomes in a hydrogel may be effected such that the tensile strength of the resulting composition is augmented thereby rendering the composition useful in applications in which the neat hydrogel was not.

Since a hydrogel can be characterized by its degree of crosslinking, which also correlated to its tensile strength and its ability to disperses and stabilize liposomes, the method of lowering the friction coefficient of a hydrogel is effected, according to some embodiments of the invention presented herein, for hydrogels which are characterized by having a molar percentage of the crosslinking agent that ranges from 0.00001% to 50% per hydrogel-forming agent total molar content. In some embodiments, the range of molar percentage of the crosslinking agent ranges from 0.01% to 25%, from 0.2% to 25%, from 1% to 20% or from 1% to 15%, as defined herein.

As demonstrated in the Examples section below, the ability to lower the friction coefficient of a hydrogel depends to some extent on the size of the liposomes dispersed therein. According to some embodiments of the present invention, the method is effected by forming the hydrogel in the presence of liposomes having an average diameter of at least 50 nm, at least 60 nm, at least 70 nm, at least 80 nm, at least 90 nm, at least 100 nm, at least 200 nm or at least 500 nm in diameter and larger, as defined herein.

As also demonstrated in the Examples section below, the ability to lower the friction coefficient of a hydrogel depends to some extent on the amount of liposomes dispersed therein.

According to embodiments of the present invention, the method is effected by forming the hydrogel in the presence of liposomes such that the final concentration of liposomes dispersed in the hydrogel is at least 1 mM, at least 2 mM, at least 4 mM, at least 6 mM, at least 10 mM, at least 12 mM, at least 16 mM, at least 20 mM, at least 24 mM, at least 30 mM, at least 35 mM, at least 40 mM, at least 60 mM, at least 100 mM, or at least 200 mM, as defined herein.

The method presented herein can be applied in cases where lowering the friction coefficient of a hydrogel, or a composite material containing a hydrogel, can benefit also from utilizing the capacity of liposomes to encapsulate and/or incorporation in their bilayer additional active agents, as this term is defined and exemplified hereinabove.

According to some embodiments of the present invention, applying the method for lowering the friction coefficient of a hydrogel or a composite material containing a hydrogel, namely incorporating liposomes in a hydrogel, may reduce the friction coefficient of the neat hydrogel by a factor of at least 2, a factor of at least 3, a factor of at least 5, a factor of at least 6, a factor of at least 7, a factor of at least 8, a factor of at least 9, a factor of at least 10, a factor of at least 12, a factor of at least 14, a factor of at least 16, a factor of at least 18, a factor of at least 20, a factor of at least 25, a factor of at least 30, a factor of at least 35, a factor of at least 40, a factor of at least 50 or by a factor of at least 60 or more.

It is noted herein that any type and/or size of the liposomes, their concentration in the hydrogel-forming composition, the chemical composition of the liposomes, the chemical composition of the hydrogel and the degree of crosslinking of the hydrogel, are according to any one of the embodiments described herein, in any combination.

Process of Manufacturing:

The process for manufacturing the hydrogel/liposomes compositions presented herein, or the process by which the method of lowering the friction coefficient of a hydrogel, is based on first manufacturing the liposomes according to the requirements and conditions discussed hereinabove (lipid composition, type and size, inclusion of polymers, inclusion of additional active agents etc.), and subsequently forming the hydrogel in the presence of these liposomes under the conditions discussed hereinabove (liposome concentration, degree of crosslinking, inclusion of fibrous materials and scaffold elements etc.).

According to an aspect of some embodiment of the present invention, there is provided a process for preparing the hydrogel/liposomes composition presented herein, which is carried out by:

Making or otherwise providing a plurality of liposomes as an aqueous suspension; and mixing the suspension with hydrogel-forming agent and a crosslinking agent, thereby obtaining the composition. The process may further makes use of an initiator, or a radical initiator agent, which is typically added to the liposome suspension. The process may further makes use of a catalyst which is typically added to the polymerization mixture.

Once all the ingredients are mixed together into a homogeneous mixture under conditions that maintain the integrity of the liposomes and all other components, the polymerization and the formation of the hydrogel is allowed to go to completion (cure), and the resulting composition can be molded, cut, processed and shaped into any desired shape.

Alternatively, the mixture of the pre-polymerized composition can be poured, cast, sprayed, coat or otherwise applied on or in a preformed substrate, and allowed to cure in situ.

Gelatin Methacrylate Hydrogels Encapsulating Liposomes:

The following is a representative embodiment of some embodiments of the present invention in which a pre-formed polymer is rendered crosslinkable by converting at least some of the units (monomers) therein into crosslinkable monomers having crosslinkable functional groups as described hereinabove.

While the representative embodiment is using gelatin as an exemplary pre-formed polymer, it is to be understood that other pre-formed polymers are also encompassed by embodiments of the present invention, and include, without limitation, polycaprolactone, peptides, polysiloxanes, hyaluronic acid, polysaccharides, chitosan, cellulose, alginate, polyglycols and any copolymer and mixes thereof.

According to an aspect of some embodiments of the present invention, there is provided a composition which includes a gelatin methacrylate-based hydrogel or a composite material containing a gelatin methacrylate-based hydrogel, and a plurality of liposomes dispersed throughout the bulk of the gelatin methacrylate-based hydrogel.

According to some embodiments, the gelatin methacrylate-based hydrogel of the composition or composite is characterized by a degree of methacrylation (DM) of amino groups in the gelatin, which is converted to gelatin methacrylate, which can be correlated to the "degree of crosslinking" as discussed hereinabove. A degree of methacrylation is typically assessed by percent of gelatin amino functional groups that underwent methacrylation out of the total number of the amino groups that can undergo methacrylation. As methacrylation correlated to the degree of crosslinking in the hydrogel, the higher the DM level, the more crosslinking is expected to occur in the hydrogel during curing. According to some of any of the embodiments of the present invention, the degree of methacrylation in the gelatin methacrylate-based hydrogels ranges from 10 percents to 90 percents and all the possible subranges as well as individual numerical values within that range. According to some embodiments, the degree of methacrylation is 5% or higher, 10% or higher, 20% or higher, 30% or higher, 40% or higher, 50% or higher, 60% or higher, 70% or higher, 80% or 90% or higher. According to some embodiments, the DM is about 75%.

The correlation between the "degree of methacrylation" to the "molar percent of a crosslinking agent to hydrogel-forming agent" can be calculated based on the number of lysine and hydroxylysine residues found in gelatin; these residues provide the amino functional groups in gelatin that undergo methacrylation. Since gelatin is known to contain 35 lysine and hydroxylisyne residues per 1000 residues (equivalent to 0.35 mmol amino groups per one gram of gelatin, or 0.35 M), it can be said that 3.5% of the monomers of gelatin can potentially undergo methacrylation. If 75% of these available amino groups undergo methacrylation, and every two methacrylic moieties form one crosslinking bond, the molar percent of a crosslinking agent to hydrogel-forming agent in the case of gelatin methacrylate-based hydrogels is about 3.5%*0.75/2=1.3%. At a DM of 50%, the molar percent of crosslinking is about 0.9%, and for a DM of 90% the crosslinking rate is about 1.6%.

According to some embodiments of the present invention, the degree of crosslinking of the liposome-containing degree of gelatin methacrylate-based hydrogels is about 0.2 molar percent or higher, about 0.3 molar percent or higher, about 0.5 molar percent or higher, about 0.7 molar percent or higher, about 0.9 molar percent or higher or about 1 molar percent or higher, based on the calculation presented hereinabove.

According to an aspect of some embodiments of the present invention, there is provided a method of lowering a friction coefficient of a gelatin methacrylate-based hydrogel or of a composite material containing a gelatin methacrylate-based hydrogel, the method being effected by forming the hydrogel in the presence of a plurality of liposomes.

According to some embodiments of any embodiment of the present invention, forming the gelatin methacrylate-based hydrogel encapsulating liposomes, as described herein, is such that the liposomes are dispersed throughout the bulk of the gelatin methacrylate-based hydrogel.

According to some embodiments, the composition or composite based on gelatin methacrylate-based hydrogel encapsulating liposomes, as described herein, is further characterized by a shear storage modulus (G') of at least 1000 Pa, at least 1500 Pa, 2000 Pa, 2500 Pa, 3000 Pa or at least 4000 Pa.

According to some embodiments, the composition based on gelatin methacrylate-based hydrogel encapsulating liposomes, as described herein, is further characterized by an average diameter of the liposomes is larger than 60 nm, 70 nm, 80 nm, 90 nm, 100 nm, 150 nm or larger than 200 nm.

According to some embodiments, the concentration of liposomes in the gelatin methacrylate-based hydrogel ranges from 1 mM to 500 mM, or alternatively, the concentration of liposomes in the gelatin methacrylate-based hydrogel is higher than 4 mM, 8 mM, 12 mM, 16 mM, 20 mM, 30 mM, 50 mM, 100 mM, 150 mM, 200 mM, 250 mM, 300 mM, 40 mM or higher than 500 mM or higher.

According to some embodiments, the liposomes incorporated into the gelatin methacrylate-based hydrogel are being selected from the group consisting of SUV, LUV or MLV liposomes.

According to some embodiments, the liposomes incorporated into the gelatin methacrylate-based hydrogel include phosphatidylcholines such as DLPC, DMPC, DPPC, HSPC and/or DSPC.

According to some embodiments, the liposomes incorporated into the gelatin methacrylate-based hydrogel further include cholesterol at a concentration, in terms of molar percent relative to the total lipid composition of the liposome, that ranges from 1% to 50%, or from 1% to 40%, or from 1% to 10% and all the possible subranges as well as individual numerical values within that range, or 50% or lower.

According to some embodiments, the liposomes incorporated into the gelatin methacrylate-based hydrogel further include an additional agent selected from the group consisting of a polymer, cholesterol, liposome-stabilizing agent, a labeling agent, a bioactive agent and a therapeutically active agent, as these are defined herein in any one of the respective embodiments thereof.

According to some embodiments, the liposomes incorporated into the gelatin methacrylate-based hydrogel are prepared in the presence of a polymer, a liposome-stabilizing polymer, cholesterol and/or a liposome-stabilizing agent. According to some embodiments, the liposome-stabilizing agent is a polymer. According to some embodiments, the polymer can be poly(2-hydroxyethyl methacrylate) (pHEMA), alginate and hyaluronic acid (HA). In some embodiments, the concentration of the polymer in the liposome preparation solution ranges from 0.1 mg polymer per 1 ml of liposome suspension solution to 5 mg/ml and all the possible subranges as well as individual numerical values within that range.

According to some embodiments, the composite material containing a gelatin methacrylate-based hydrogel includes a material selected from the group consisting of a woven mesh of fibers, non-woven fibers, a plurality of rods and a net.

Applications:

As discussed hereinabove, the hydrogel/liposomes compositions presented herein can be used to make any type of article-of-manufacturing to be used in various applications. Such article-of-manufacturing can be a part of an implantable medical device or a drug-delivery system, and can take the form of any semi-solid or solid body, a disc, a fiber, a fabric, a tube, a film, a rod, a ring, a tubular mesh and any combination thereof.

The hydrogel/liposome compositions and composites, according to some of any of the embodiments of the present invention, can be used for the coating of a variety of substrates. An exemplary field of interest is the coating of medical articles for use in or on a bodily site, particularly catheters, guide wires or parts of such articles. As a coating material, the hydrogel/liposomes compositions can coat a part of an article-of-manufacturing or a device. Hence, the compositions presented herein may be used to completely or partially coat an implantable medical device, a drug-delivery system, any solid body, a disc, a fiber, a fabric, a tube, a film, a rod, a ring and/or a tubular mesh.

The capacity to maintain the mechanical properties, including shape and friction coefficient after a dehydration-rehydration cycle, renders the hydrogel/liposomes compositions presented herein particularly useful for manufacturing and/or coating parts and devices that are stored dry and used when the composition is fully hydrated.

Since hydrogels can be made from biocompatible materials and have many mechanical and chemical properties that mimic biological tissues, the compositions presented herein may be used to support and/or replace failing or degraded tissue in a living organism. For example, the composition may be used to manufacture parts of a joint-replacement implantable device, and replace cartilage that failed or degraded.

For another example, the composition presented herein can be used to coat the inner and outer surface of a tube a catheter, an orthodontic device or a stent, or in general used as a coating for low friction structural scaffolds which are used externally or internally (implantable), thereby allowing the practitioner to more freely manipulate the structural scaffold the path to and/or in the target organ or bodily site, and manipulate structural scaffold elements that are passed through a tube more effectively, as the friction coefficient of the inner and outer surfaces of the tube and/or the structural scaffold element are significantly reduced.

Other than providing a beneficial reduction in the friction coefficient, the incorporation of additional active agents in the hydrogel/liposomes composition, either as part of the liposomes or as part of the hydrogel, can assist beneficial processes and prevent undesired consequences while using the devices or articles-of-manufacturing which are based or using the composition. For example, if tissue regeneration and proliferation agents are added to the composition used in a joint-replacement device, the composition will serve a cartilage-mimicking substance while allowing the growth of host-cells in and around the composition. Alternatively, the additional agent(s) can prevent the formation of a biofilm or plaque on the surface of an implantable device coated by the compositions presented herein. Coating a catheter device or an implantable device with the composition presented herein which includes an antimicrobial agent will prevent an accidental infection that may be carried in by insertion of the device.

A Method of Treatment:

As discussed hereinabove, the hydrogel/liposomes compositions presented herein can be used in medical application to replace degraded tissue such as cartilage. Hence, according to an aspect of some embodiments of the present invention, there is provided a method of treating a living organism suffering from a medical condition associated with loss of or damaged cartilage, which is effected by replacing at least a portion of the damaged or missing cartilage with the hydrogel/liposomes composition presented herein.

It is noted herein that for any particular application and method of treatment, a specific combination of parameters will give an optimal composition. For example, in order to replace damaged cartilage, the composition should be characterized by suitable mechanical properties, particularly tensile strength and long-term durability, while exhibiting and maintaining (under load, temperature and duration) friction coefficient which resembles that of cartilage, and further contain additional active agents that will prevent undesired consequences, such as inflammation and infection, and promote beneficial processes such as self-tissue regeneration.

In the context of drug delivery, the compositions, composites and articles, according to some embodiments of the present invention, can be used to deliver and release a variety of bioactive and therapeutic agents which are useful in the treatment of a variety of medical conditions, including, without limitation, inflammation, infection, tumor suppression, bone tissue formation, tissue proliferation, metabolite and endocrine regulation, pain relief, and the likes.

It is expected that during the life of a patent maturing from this application many relevant hydrogels exhibiting a low friction coefficient will be developed and the scope of the term hydrogels exhibiting a low friction coefficient is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Materials and Methods

Materials:

Water used in the experiments was purified using a Barnsted NanoPure systems to 18.2 MΩ cm resistance with total organic content levels of less than about 1 ppb.

All phosphatidylcholines lipids (PCs) were purchased from Lipoid, GmbH, and are listed in Table 1.

TABLE 1

| Acronym | Full chemical name | MW | Phase transition temperature ($T_m$), °C. |
|---|---|---|---|
| DLPC | 1,2-dilauroyl-sn-glycero-3-phosphocholine | 622 | −1 |
| DMPC | 1,2-dimyristoyl-sn-glycero-3-phosphocholine | 677.9 | 23.2 |
| DPPC | 1,2-dipalmitoyl-sn-glycero-3-phosphocholine | 734.1 | 41.4 |
| HSPC | hydrogenated soybean phosphocholine | 762.1 | 52.5 |
| DSPC | 1,2-distearoyl-sn-glycero-3-phosphocholine | 790.1 | 55 |

2-hydroxyethylmethacrylate (2-hydroxyethyl 2-methylprop-2-enoate, also referred to herein as hydroxyethylmethacrylate or HEMA); ethylene glycol dimethacrylate, also referred to herein as 1,2-ethanediol dimethacrylate, ethylene dimethacrylate, ethane-1,2-diyl bis(2-methylacrylate) or EGDMA); ammonium persulfate (APS); N,N,N',N'-tetramethylethylenediamine (TMEDA); and poly(ethylene glycol)$_n$ dimethacrylate, also referred to herein as poly(ethylene glycol) dimethacrylate, poly-EGDMA (9EGDMA is an exemplary crosslinking agent having an average molecular weight value of 550, which is equivalent to 9 repeating units of the monomer EGDMA, or poly(ethylene glycol)$_9$ dimethacrylate); were purchased from Sigma-Aldrich and used as received.

Liposomes Preparation:

Multilamellar vesicles (MLV) composed of pure phosphatidylcholines, such as DLPC, DMPC, DPPC, HSPC and/or DSPC, were prepared by hydrating the lipids in pure water at a temperature of at least 5° C. above the lipid $T_m$. In order to dissolve HSPC and/or DSPC, 10% by volume of ethanol, heated to at least 5° C. above the $T_m$ of the lipid, was added to the mixture before adding water.

In order to obtain unilamellar liposomes (SUV of less than 100 nm in diameter), MLVs were downsized by stepwise extrusion through polycarbonate membranes starting with a 400 nm and ending with 50 nm pore size membrane, using a Lipex 100 mL extruder system (Northern Lipids, Vancouver, Canada), heated to at least 5° C. above the lipid $T_m$.

SUV liposomes radii were measured using a Dynamic Light Scattering and showed a clear peak at 30±10 nm for all liposomes types immediately after their preparation. However, as discussed below, these small liposomes were not stable in term of their size, which grew over time, therefore the liposomes that were effectively used in the preparation of the low-friction hydrogels, according to embodiments of the present invention, exhibited a minimal average size of more than 80 nm in diameter.

Briefly, a Viscotek 802 (DLS) spectrophotometer was used in order to measure the liposomes radii in solution. Samples were diluted ten-fold and were measured about 12 times in the intensity distribution working mode. DLPC, DMPC and DPPC SUV liposomes showed a clear peak of radius of 30±10 nm when measured immediately after the liposome preparation. The radius tended to increase with time to about 60±10 nm. It has been noted that over time, an additional population of liposomes exhibiting much higher radius size, may appear in the measured samples. SUV HSPC liposomes measured immediately after their preparation showed higher radius values of about 40±10 nm. The SUV HSPC radius also increased with time.

Without being bound by any particular theory, it is noted that the trend of increasing SUV liposome radii over time is a consequence of preparing liposomes that lack stabilizing agents such as introducing PEG groups. Introducing PEGs cause steric repulsions and prevent liposomes from aggregating, without which, the radii values tend to grow with time together with appearance of another population having a higher radius, which did not exist immediately after the liposome preparation. This observation emphasizes the difficulties in working with small liposomes of less than 80 nm in diameter in aqueous solutions.

Hydrogel Preparation:

Neat hydrogels containing 1% crosslinking agent were prepared as follows: a hydrogel-forming monomer HEMA (3.2 grams), a crosslinking agent EGDMA (52.5 µL, 1% percent of the HEMA monomer's molar content), and an aqueous solution of the radical initiator agent APS (2 ml, 53 mM) were stirred vigorously for 30 minutes until fully mixed. Thereafter 50 µL of the catalyst TMEDA was added dropwise to the mixture, and the mixture was stirred for 20 seconds and poured into a 6 cm diameter Petri dish. The resulting hydrogels, having a thickness of about 1.8 mm, were allowed to crosslink (cure) over 4-5 hours, followed by rinsing in distilled water for 3 days to remove any unreacted materials while allowing full hydration of the hydrogel.

The crosslinked, hydrated and washed hydrogel samples were cut into about 1.8 mm thick discs having a diameter of about 5 mm (for the top piece) or 20 mm (for the bottom piece) for tribological tests and other characterization methods.

Preparations of neat hydrogels containing 1% 9EGDMA were prepared by replacing the EGDMA with the equivalent molar percentage of 9EGDMA.

Typical characteristics of the resulting exemplary hydrogels are a Young modulus that ranges from 0.65 MPa to 2 MPa; and a water content of 45%±5% by weight.

Hydrogels Containing Liposomes:

Hydrogels incorporating liposomes therein were prepared similarly, while replacing the APS aqueous solution with a liposome suspension having the same APS content. The MLV liposomes' stock was prepared by adding 2 ml of the liposomes suspension at a concentration of 45 mM to an aqueous solution of the radical initiator agent. SUV liposomes suspension was prepared similarly at a concentration of 30 mM. It is noted herein that liposome suspensions can be prepared and maintained with other aqueous solutions at various concentrations, and added to the hydrogel-preparation mixture.

Table 2 below presents some exemplary compositions based on liposome-loaded hydrogels according to embodiments of the present invention, wherein the percent amount are given as weight percent with respect to the total weight of the composition, and the liposome concentration is denoted by the liposome concentration in the 2 ml suspension containing APS, which was used to prepare the hydrogel as presented hereinabove.

According to the exemplary hydrogel/liposome compositions demonstrated herein, the concentration of liposome in the original solution is diluted by 60% due to the addition of hydrogel-forming monomers. Therefore, in the case of the larger liposomes (MLV), their concentration in the hydrogel/liposome composition was about 18 mM (40% of the original 45 mM), while in the case of the smaller liposomes (SUV), their concentration in the final composition was about 12 mM (40% of 30 mM).

TABLE 2

| | Sample acronym | | | | | |
|---|---|---|---|---|---|---|
| Component | HEMA EGDMA 1% Neat | HEMA EGDMA 2% Neat | HEMA 9EGDMA 4% Neat | HEMA 9EGDMA 4% SUV DMPC | HEMA EGDMA 1% MLV HSPC | HEMA EGDMA 2% MLV HSPC |
| Monomer | HEMA | HEMA | HEMA | HEMA | HEMA | HEMA |
| Crosslinking agent | EGDMA 1% | EGDMA 2% | 9EGDMA 4% | 9EGDMA 4% | EGDMA 1% | EGDMA 2% |

TABLE 2-continued

| | Sample acronym | | | | | |
|---|---|---|---|---|---|---|
| Component | HEMA EGDMA 1% Neat | HEMA EGDMA 2% Neat | HEMA 9EGDMA 4% Neat | HEMA 9EGDMA 4% SUV DMPC | HEMA EGDMA 1% MLV HSPC | HEMA EGDMA 2% MLV HSPC |
| Radical initiator agent | APS 0.42% | APS 0.42% | APS 0.42% | APS 0.42% | APS 0.42% | APS 0.42% |
| Catalyst | TMEDA 0.79% | TMEDA 0.79% | TMEDA 0.79% | TMEDA 0.79% | TMEDA 0.79% | TMEDA 0.79% |
| Liposomes | — | — | — | 6.6 mM | 10 mM | 10 mM |

Example 2

Product Characterization

Cryo-SEM Freeze Fracture Imaging:

Fresh hydrogel disc sample were flash-frozen (cryofixation), then fractured while maintained the sample at cryogenic (liquid nitrogen) temperature. Ice was removed by sublimation when formed on the cold fractured surface by increasing the temperature to about −100° C. for several minutes.

Figure 1:
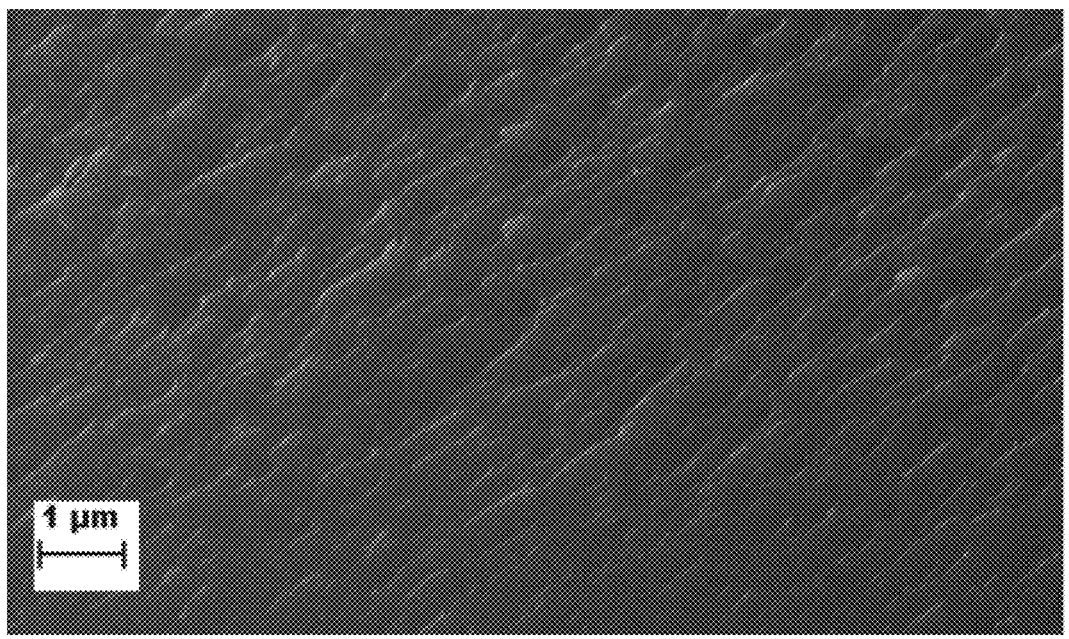
FIG. 1 presents an electron-micrograph of the surface of a freeze-fractured sample of a HEMA 9EGDMA 4% neat hydrogel (without liposomes) (EDGMA and 9EDGMA are cross-linker groups and the % refers to their concentration)

FIG. 1 presents an electro-micrograph of a fractured sample of a HEMA 9EGDMA 4% neat hydrogel (without liposomes).

As can be seen in FIG. 1, the neat hydrogel show a feature-less structure of the hydrogel, with marks of the fracture process.

FIGS. 2A-C present electro-micrographs of a fractured sample of HEMA 9EGDMA 4% SUV DMPC hydrogel containing liposomes, taken at a magnification of 2000 (FIG. 2A), a magnification of 24,000 (FIG. 2B) and a magnification of 60,000 (FIG. 2C).

As can be seen in FIGS. 2A-C, images of the liposome-containing hydrogel samples show a notable organization of the liposomes inside the bulk of the hydrogel, wherein the liposomes are encapsulated as clusters inside pores in the hydrogel having a substantially uniform pore-size of about 2 µm a diameter.

The SUV DMPC liposomes used to obtain the samples presented in FIGS. 2A-C where subjected to particle size measurement in a dynamic light scattering. The DLS measurements showed two distinguished populations of liposomes, having different diameters of D1=120 nm and D2=415 nm. Indeed, the freeze fracture images (FIGS. 2A-C) corroborate that the liposomes seen in the hydrogel pores (also referred to herein as "pockets") are composed of two different small liposome sizes, corresponding well with the DLS results.

Young's Modulus Measurements:

a) Tensile Strength Measurements

Mechanical modulus measurements were performed using a Universal Testing Machine (UTM, Instron Corporation, Canton, Mass.). Cylindrical samples having dimensions of 6 mm diameter and 3 mm thickness were compressed between two flat plates to study their stress-strain relationships. Three different hydrogel samples were measured for each modulus determination.

Figure 3A:
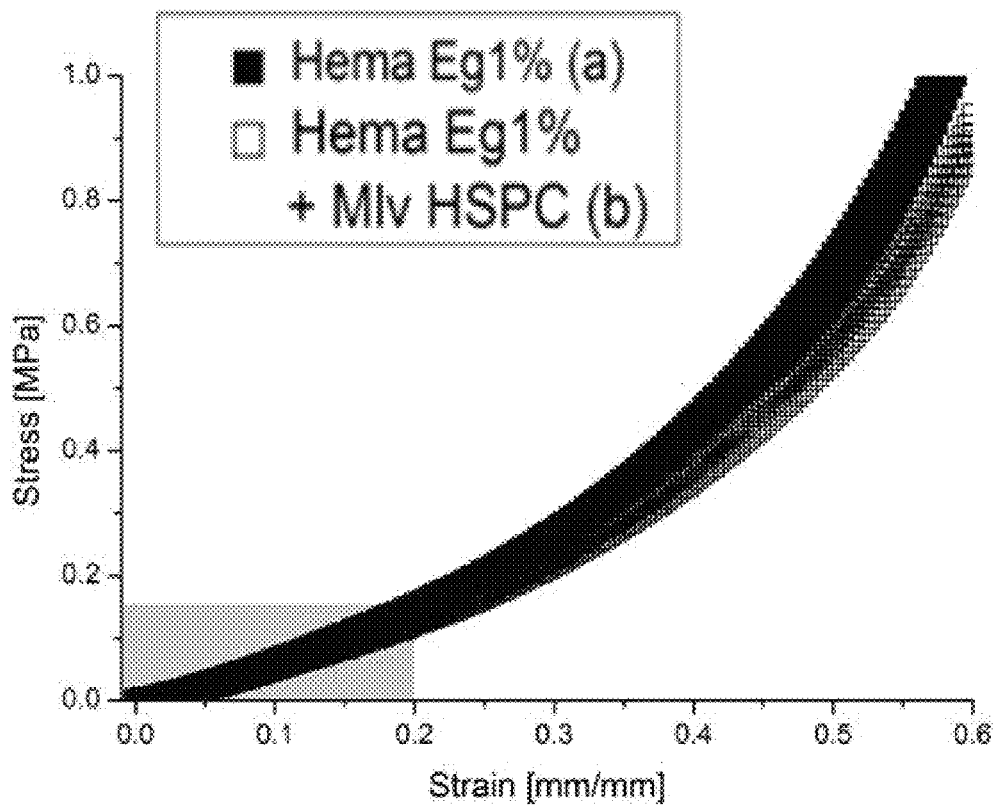
FIGS. 3A-B present a stress-strain curve of an exemplary HEMA EGDMA 1% neat hydrogel sample and an exemplary HEMA EGDMA 1% hydrogel sample containing MLV HSPC liposomes (compression region of 0 to 60% in FIG. 3A and compression region of 0 to 20% in FIG. 3B)
Figure 3B:
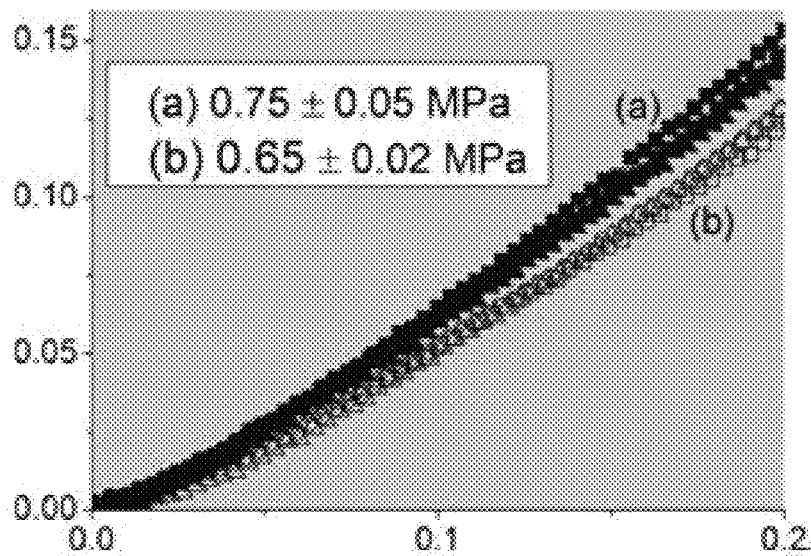

FIGS. 3A-B presents a stress-strain curve of an exemplary HEMA EGDMA 1% neat hydrogel sample and an exemplary HEMA EGDMA 1% hydrogel sample containing MLV HSPC liposomes (compression region of 0 to 60% in FIG. 3A and compression region of 0 to 20% in FIG. 3B).

As can be seen in FIGS. 3A-B, the Young's modulus, calculated from the slope of the stress-strain curve within the region of 0-20% compression was 0.75±0.05 for the neat hydrogel and 0.65±0.05 for the liposome-containing hydrogel.

b) Compression Measurements Using a Rheometer

Compression measurements were performed using HAAKE Mars III Rheometer (Thermo Scientific). Cylindrical hydrogel samples having dimensions of 10 mm radius and 3.5±0.5 mm thickness were compressed by using a cone- and a plate configuration. Measurements were performed at 25° C. at velocity of 0.005 mm/sec.

Table 3 summarized the Young's modulus for exemplary hydrogels at compressions region of 0-10% and 0-20%.

TABLE 3

| Sample name | Strain region | Young's Modulus |
|---|---|---|
| HEMA EGMA 0.1% neat | 0-20% | 0.29 MPa |
| HEMA EGMA 0.1% + MLV HSPC | 0-20% | 0.2 MPa |
| HEMA EGMA 0.5% neat | 0-20% | 0.47 MPa |
| HEMA EGMA 0.5% + MLV HSPC | 0-20% | 0.33 MPa |
| HEMA EGMA 1% neat | 0-20% | 0.74 MPa |
| HEMA EGMA 1% + MLV HSPC | 0-20% | 0.65 MPa |
| HEMA 9EGMA 4% neat | 0-10% | 1.9 MPa |
| HEMA 9EGMA 4% + SUV DMPC | 0-10% | 1.9 MPa |

Figure 4A:
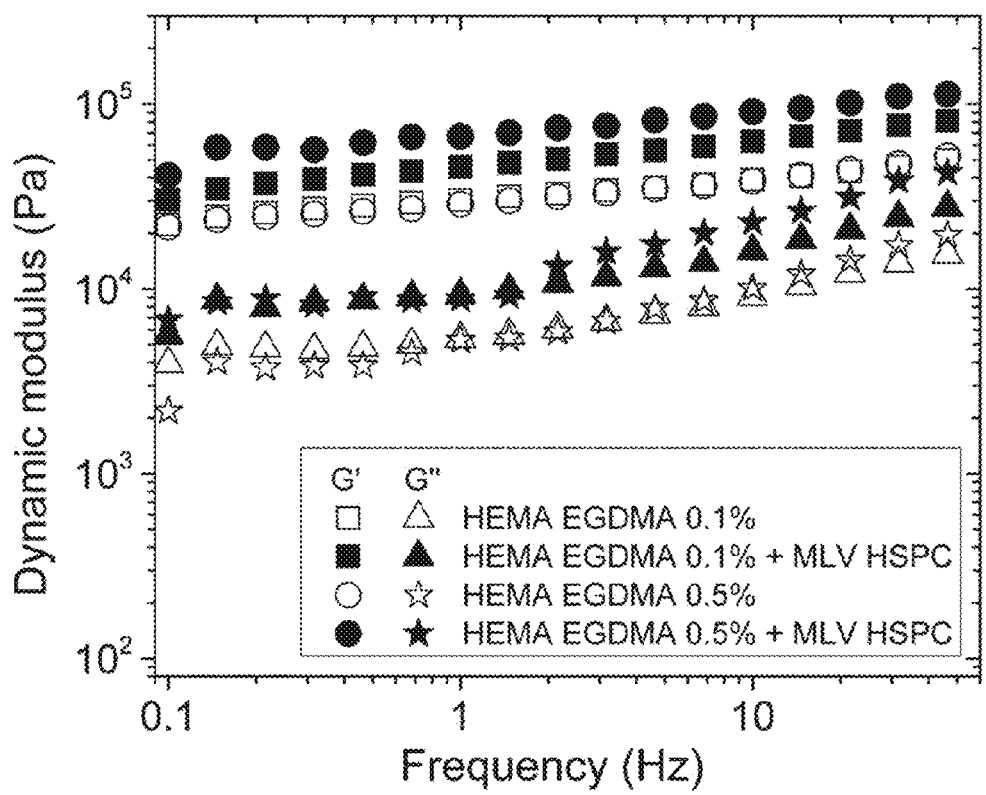
FIGS. 4A-B present frequency sweep test results obtained for exemplary HEMA EGDMA 0.1% and 1% neat marked with white squares for G' and white triangle for G" (FIG. 4A and FIG. 4B respectively), HEMA EGDMA 0.1% and 1%+MLV HSPC marked with black squares for G' and black triangle for G" (FIG. 4A and FIG. 4B respectively), HEMA EGDMA 0.5% and HEMA 9EDGMA 4% neat marked with white circles for G' and white stars for G" (FIG. 4A and FIG. 4B respectively), and HEMA EGDMA 0.5% and 4%+MLV HSPC marked with black circles for G' and black stars for G" (FIG. 4A and FIG. 4B respectively), as measured at 20° C., after running stress dependence of G' and G", and verifying linear behavior of G' under such pressure.
Figure 4B:
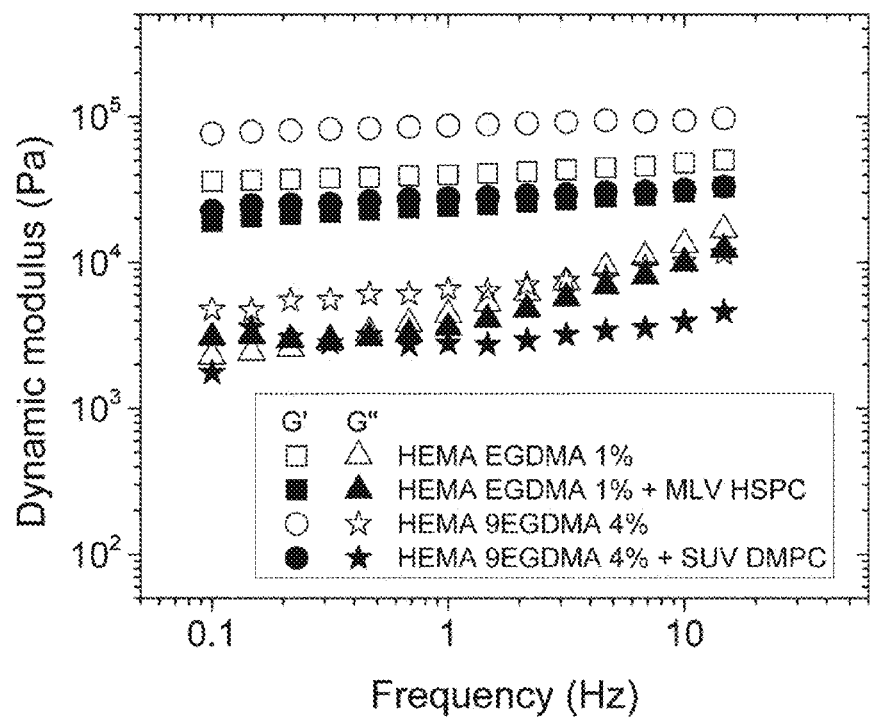

Dynamic Mechanical Characterization of Hydrogels:

FIGS. 4A-B present frequency sweep test results obtained for exemplary HEMA hydrogels (HEMA EGDMA 0.1% and 1% neat marked with white squares for G' and white triangle for G" (FIG. 4A and FIG. 4B respectively), HEMA EGDMA 0.1% and 1%+MLV HSPC marked with black squares for G' and black triangle for G" (FIG. 4A and FIG. 4B respectively), HEMA EGDMA 0.5% and 4% neat marked with white circles for G' and white stars for G", and HEMA EGDMA 0.5% and 4%+MLV HSPC marked with black circles for G' and black stars for G" (FIG. 4A and FIG. 4B respectively), as measured at 20° C. and a load of 5 Pa, after running stress dependence of G' and G", and verifying linear behavior of G' under such pressure.

Stemming from the dynamic mechanical tests, the storage modulus G' and the loss modulus of the following HEMA hydrogels shown in FIGS. 4A-B are presented in Tables 4A-B respectively below.

TABLE 4A

| Sample name | G' (Pa) | G" (Pa) |
|---|---|---|
| HEMA EGMA 0.1% neat | $3 \times 10^4$ | $5.4 \times 10^3$ |
| HEMA EGMA 0.1% + MLV HSPC | $4.6 \times 10^4$ | $5.8 \times 10^3$ |
| HEMA EGMA 0.5% neat | $3 \times 10^4$ | $5.3 \times 10^3$ |
| HEMA EGMA 0.5% + MLV HSPC | $6.7 \times 10^4$ | $8.8 \times 10^3$ |

TABLE 4B

| Sample name | G' (Pa) | G" (Pa) |
|---|---|---|
| HEMA EGMA 1% neat | $4 \times 10^4$ | $4.4 \times 10^3$ |
| HEMA EGMA 1% + MLV HSPC | $2.4 \times 10^4$ | $3.5 \times 10^3$ |
| HEMA 9EGMA 4% neat | $8.7 \times 10^4$ | $6.5 \times 10^3$ |
| HEMA 9EGMA 4% + SUV DMPC | $2.7 \times 10^4$ | $2.8 \times 10^3$ |
| HEMA EGMA 2% neat | $1.6 \times 10^5$ | $3.8 \times 10^3$ |
| HEMA EGMA 2% + MLV DMPC | $6.2 \times 10^4$ | $1.5 \times 10^3$ |

As can be seen in FIGS. 4A-B and Tables 4A-B, the results show that the storage shear modulus, G', is higher than the loss shear modulus, G", over the entire frequency region. These results indicate that the elastic response of the hydrogels, according to embodiments of the present invention, is stronger than the viscous response, therefore these HEMA hydrogels have a solid like behavior.

Typical hydrogels used, for example, to dispense liposomes for drug delivery or hydrogels used as lubricants in aqueous conditions, typically exhibit a Young's moduli lower than 1000 Pa. These values indicate that these hydrogels are drastically distinct from the hydrogels used in embodiments of the present invention, since they are fragile, soft and "fluid like. Typically, soft hydrogels cannot be characterized using compression tests since these hydrogels shatter during the tests. Rheological tests, can be used to compare soft to hard hydrogels, based on their G' and G" values.

Liposomal drug dispersed in hydrogels of carbopol 974, hydroxylethyl-cellulose (HEC) or a mixture of the two [Colloid and Surfaces B: Biointerfaces, 55, 2007, 212-221] typically exhibit G' values in the range of 3-300 Pa, and G" of 10-200 Pa. In temoporfin-loaded liposomal gels made from soybean lecithins for drug delivery onto topical and deeper skin layers [*International Journal of Pharmaceutics*, 373, 2009, 77-84], G' values of 198.5-1046.7 Pa and G" values range 192-330.7 Pa for the higher PC-content lipids. Another hydrogel system, prepared from egg phosphatidylcholine (EPC) liposomes in a poly(N-isopropylacrylamide) hydrogel showed values of G' of about 750 Pa and G" of 50-100 Pa for the hydrogel containing the EPC [Soft Matter, 8, 2012, 4517]. Hydrogel that composed of MLV's containing the ocular drug ofloxacin were examined [AAPS PharmSciTech, 10, 2009, 1336], and the rheological behavior of the hydrogel showed an elastic modulus G' of 45 Pa. Formulation of vasoactive intestinal peptide (VIP) based on the incorporation of VIP-loaded rhodamine-conjugated liposomes within hyaluronic acid gel for the treatment of endotoxin-induced uveitis, showed values of G'=157-379 Pa and G"=127-236 Pa, at 1 Hz frequency [*Journal of Controlled Release*, 139, 2009, 22]. Other studies of hydrogel containing liposomes, such as the liposomal hydrogel based on Carbopol 940 [*Romanian Biotechnological Letters*, 16 (1), 2011, 47] and other liposomal gels for vaginal drug delivery, based on Carbopol 974P NF and Carbopol 980 NF [*International Journal of Pharmaceutics*, 219, 2001, 139], report only the flow properties of the gels indicating a fluid-like gel.

It is therefore noted herein that the hydrogels used in embodiments of the present invention exhibit G' values which are much higher than the values exhibited by hydrogels reported in the literature.

Example 3

Gel-to-Gel Friction Measurements

Gel-to-gel friction tests were carried out using a CETR© tribometer, UMT model with a two sensors, one for loads in the range of 5-1000 g, and another one which enables application of high normal loads, in the range of 1-40 Kg. The set-up configuration was of a hydrogel on a hydrogel, in which both upper and lower samples are immersed in pure water. The pressure between the two samples was calculated according to the smaller surface, which was the upper hydrogel sample having a diameter of 5 mm. The hydrogel samples were subjected to relative sliding over a wide range of loads using two different sensors: sensor 1 applying loads of 10 to 500 grams and sensor 2 applying high loads of 1 to 4 Kg, whereas the high loads sensor simulated physiological joint pressures of 0.73±0.1 MPa to 8.75±1.25 MPa.

The testing parameters were as follows: Sliding velocity of 1 mm/sec, sliding amplitude of 1 mm and dwell time of 5 sec at each normal load before shearing commences. Experiments were conducted at room temperature (about 25±1° C.).

The static friction coefficient was obtained from the maximum value of the shear trace, and the kinetic friction coefficient was calculated as the average value at the sliding region, and the results were calculated as the mean of 2-3 independent experiments using 2-3 fresh pairs of hydrogel samples in each case, and 60 back-and-forth cycles per measurement.

The following figures show typical trace plots, obtained by a tribometer for symmetric (top and bottom) pure hydrogel samples. Different traces represent different load and pressures applied to the hydrogels. The trace plot marked by (a) in the following figures refers to a shear outline where sliding occurs. In such cases, the effective friction coefficient was calculated directly from the trace peak marked by "µ". The peak "µ" is the dynamic friction, which is calculated as $F_L/F_N$, where $F_L$ is the lateral force, taken from the plateau region of the trace, and $F_N$ is the applied normal force. In cases where the static friction in the system is too high, sliding does not occur and the system is said to be in "rigid coupling". In a rigid coupling scenario, the two surfaces move together and the trace plot exhibits a round sawtooth wave form. For example, in the examples presented herein, under relatively low pressures, such as 1-2 atmospheres, the system is in rigid coupling. The pressure in each load was calculated according to $P=F_N/A$, where A is the contact area of the smaller (top) surfaces among the two opposing sample surfaces.

Figure 5:
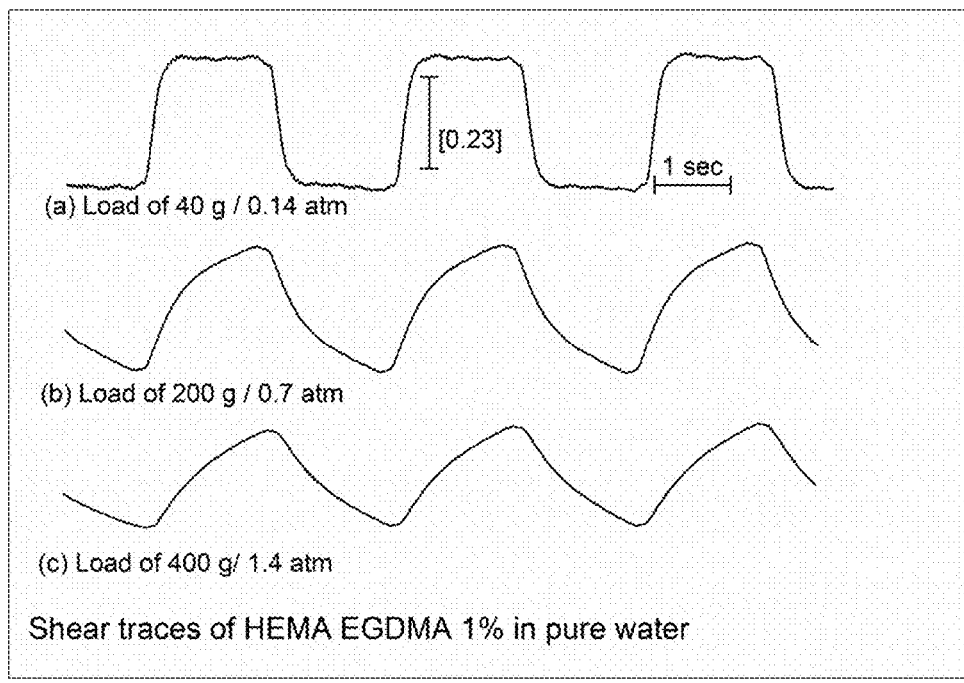
FIG. 5 presents comparative tribometer trace plots obtained for a symmetric pair of HEMA EGDMA 1% neat hydrogels, wherein trace plot (a), indicating a friction coefficient ($\mu$) of 0.23, was obtained while applying a load of 40 grams or 0.14 atmospheres, trace plot (b), exhibiting sawtooth wave form and thus cannot deduce a $\mu$ value, similar to the behavior seen in trace plot (c) at a load of 400 grams or 1.4 atmospheres.

FIG. 5 presents comparative tribometer trace plots obtained for a symmetric pair of HEMA EGDMA 1% neat hydrogels, wherein trace plot (a), indicating a friction coefficient (µ) of 0.23, was obtained while applying a load of 40 grams or 0.14 atmospheres, trace plot (b), exhibiting sawtooth wave form and thus cannot deduce a μ value, similar to the behavior seen in trace plot (c) at a load of 400 grams or 1.4 atmospheres. It is noted that the vertical bars appearing on the traces in FIG. 5 and FIG. 6 below correspond to the values of friction coefficients noted next to them in square brackets.

As can be seen in FIG. 5, the shear trace plot measured between two HEMA EGDMA 1% neat hydrogels under low pressure of 0.14 atmosphere (trace plot (a)), exhibited a square wave form typical of a sliding scenario, while a sawtooth wave form was observed at pressures of 0.7 atmospheres and higher, which exhibited a typical rigid coupling scenario, indicating adherence and high friction forces between the two surfaces (trace plots (b) and (c)). In these rigid coupling scenarios, the hydrogel surfaces are subjected to extended wear which typically results in rupture of the surfaces.

Figure 6:
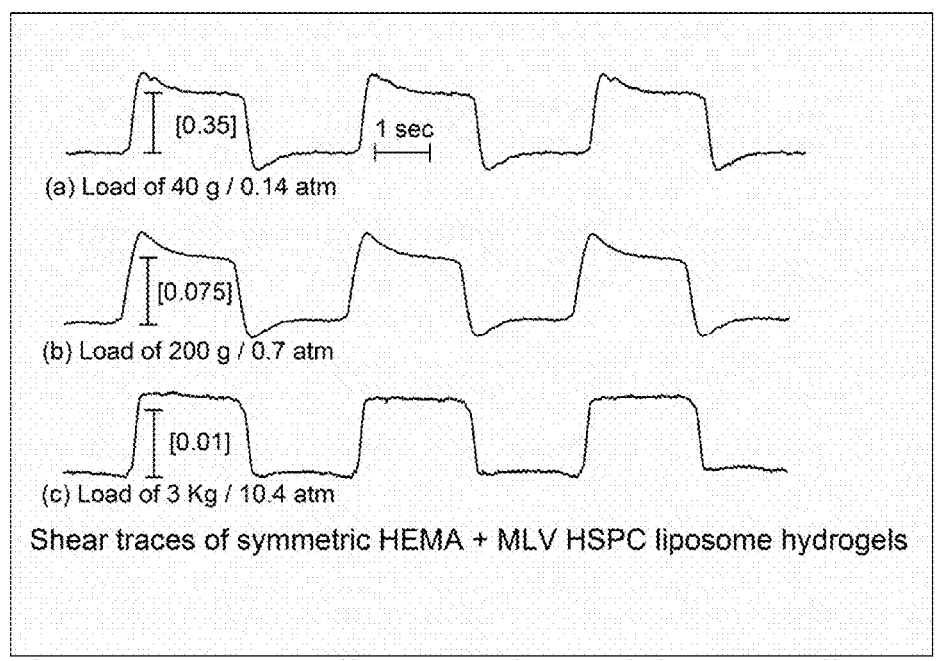
FIG. 6 presents comparative tribometer trace plots obtained for a symmetric pair of HEMA EGDMA 1% hydrogels+MLV HSPC liposomes, wherein trace plot (a), indicating a friction coefficient ($\mu$) of 0.35, was obtained while applying a load of 40 grams or 0.14 atmospheres, trace plot (b), exhibiting $\mu$ of 0.075, was obtained while applying a load of 200 grams or 0.7 atmosphere, and trace plot (c), exhibiting $\mu$ of about 0.01, was obtained while applying a load of 3000 grams or 10.4 atmospheres.

FIG. 6 presents comparative tribometer trace plots obtained for a symmetric pair of HEMA EGDMA 1% hydrogels+MLV HSPC liposomes, wherein trace plot (a), indicating a friction coefficient (μ) of 0.35, was obtained while applying a load of 40 grams or 0.14 atmospheres, trace plot (b), exhibiting μ of 0.075, was obtained while applying a load of 200 grams or 0.7 atmosphere, and trace plot (c), exhibiting μ of about 0.01, was obtained while applying a load of 3000 grams or 10.4 atmospheres.

As can be seen in FIG. 6, the low friction coefficient (μ) values measured in the symmetric HEMA EGDMA 1%+MLV HSPC sample system were reduced by more than a factor of 20 compared to the symmetric HEMA EGDMA 1% neat sample system, as shown in FIG. 5.

Figure 7:
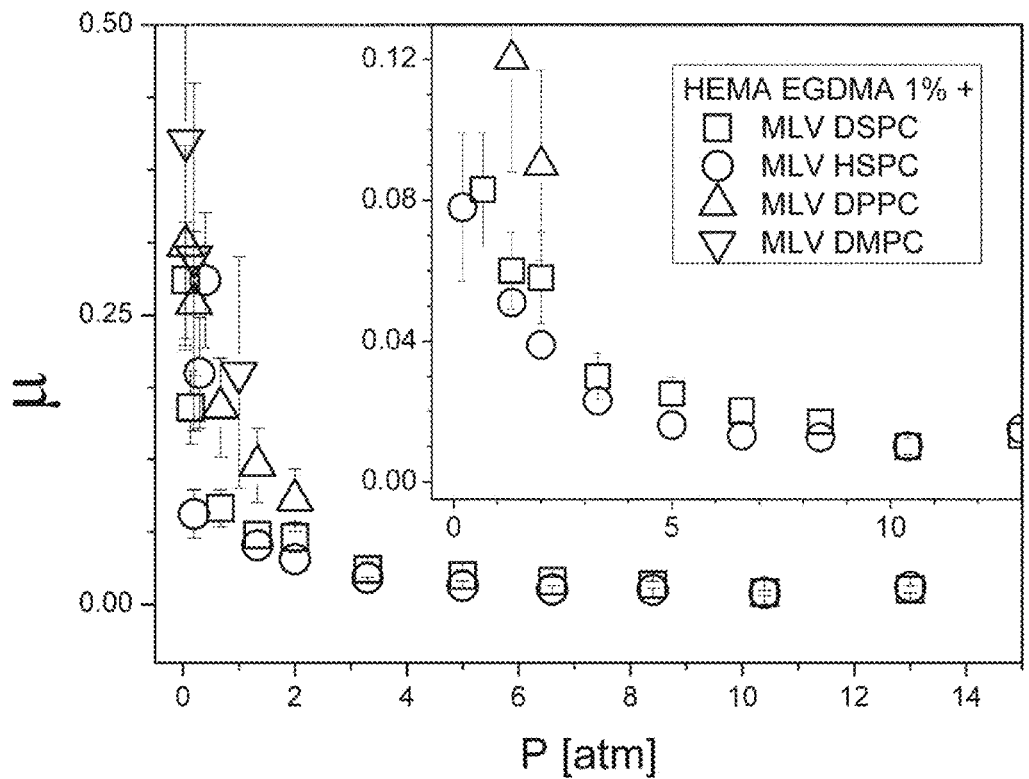
FIG. 7 presents a graph of friction coefficient values as a function of the pressure for different symmetric hydrogel sample systems, wherein the results obtained for the HEMA EGDMA 1%+MLV DSPC sample are marked by squares, the results of the HEMA EGDMA 1%+MLV HSPC sample are marked by circles, the HEMA EGDMA 1%+MLV DPPC sample is marked by top-pointing triangles, and the HEMA EGDMA 1%+MLV DMPC sample is marked by bottom-pointing triangles.

FIG. 7 presents a graph of friction coefficient values as a function of the pressure for different symmetric hydrogel sample systems, wherein the results obtained for the HEMA EGDMA 1%+MLV DSPC sample are marked by squares, the results of the HEMA EGDMA 1%+MLV HSPC sample are marked by circles, the HEMA EGDMA 1%+MLV DPPC sample is marked by top-pointing triangles, and the HEMA EGDMA 1%+MLV DMPC sample is marked by bottom-pointing triangles.

As can be seen in FIG. 7, the general trend in the graph indicates that the lower loads/pressures exhibit a higher friction coefficient. This observation is attributed to the imperfect orientation between the two opposing hydrogel samples. As load is increased, the surfaces are flattened against each other and the alignment therebetween is improved, resulting in a lower μ. As can further be seen in FIG. 7, the hydrogel/liposome compositions, according to embodiments of the present invention, exhibiting a low μ values, are the HEMA EGDMA 1% hydrogels that contains the MLV HSPC and the MLV DSPC liposomes.

Figure 8:
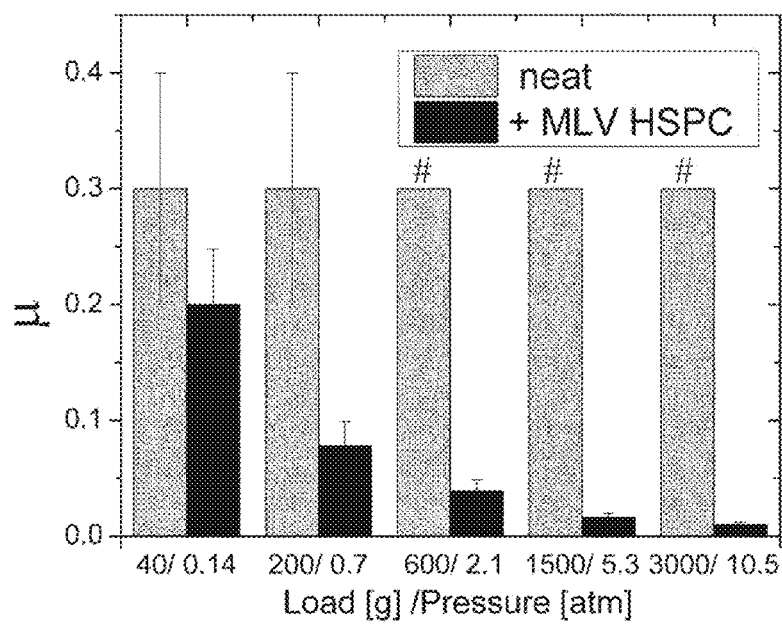
FIG. 8 presents a comparative bar-graph, showing the friction coefficients as measured under various loads between symmetric hydrogel surfaces of neat HEMA EGDMA 1% hydrogel (grey bars), and similar hydrogels containing MLV HSPC liposomes (black bars), whereas the "#" (hash) symbol indicates a rigid coupling scenario or case of a hydrogel shattering during the experiment.

FIG. 8 presents a comparative bar-graph, showing the friction coefficients as measured under various loads between symmetric hydrogel surfaces of neat HEMA EGDMA 1% hydrogel (grey bars), and similar hydrogels containing MLV HSPC liposomes (black bars), whereas the "#" (hash) symbol indicates a rigid coupling scenario or case of a hydrogel shattering during the experiment. In this context "rigid coupling" means that the surfaces do not slide past each other even at the highest shear forces applied, so that the sliding friction coefficient cannot be determined but is higher than indicated by the bar wherever a # sign appears.

As can be seen in FIG. 8, adding liposomes into the hydrogel of the symmetric HEMA EGDMA 1% hydrogel surfaces had a significant improvement in lowering the friction between the samples, as evident in the applied loads of 200 grams to 3 kg, lowering the friction coefficient μ from 0.3 to 0.01 respectively. As can further be seen in FIG. 8, in rigid coupling cases, the effect of adding liposomes to the hydrogel was more pronounced since the neat hydrogel surfaces stuck one to another, allowing no sliding motion therebetween, resulting eventually in surface damage and complete rupture of the hydrogel. In other cases, due to the high loads, the neat hydrogel sample broke down. Therefore, the "#" symbol in FIG. 8 represents high friction scenario either due to rigid coupling or/and mechanical damage/breakdown of the hydrogel sample.

It is noted herein that exposing the exemplary HEMA EGDMA 1% hydrogel containing liposomes to relatively higher loads and/or an increased numbers of cycles may also lead to surface damage and rupture; however, the results presented herein demonstrate clearly the improved friction coefficient of the HEMA hydrogels upon introduction of liposomes therein.

Distribution of Liposomes in the Hydrogel:

In order to verify the shear reduction effect of adding liposomes to a hydrogel sample at various regions of the hydrogel, liposome suspensions were applied on top of the neat hydrogel sample surface, and the friction coefficient exhibited by such samples was compared to that obtained for a corresponding sample wherein the liposomes were incorporated into the bulk of the hydrogel prior and during the polymerization and crosslinking (gelation) process. In the measurements for hydrogel having liposomes on top of their surface, friction was measured between two HEMA EGDMA hydrogel samples while using the a corresponding liposome suspension of MLV HSPC as a medium between the samples, instead of using pure water, as used in the measurements of hydrogel samples having liposomes incorporated therein. Before measurements, the neat hydrogels were incubated with the liposome suspension to ensure the adsorption of the liposomes thereon. The comparative results are presented in FIG. 9.

Figure 9:
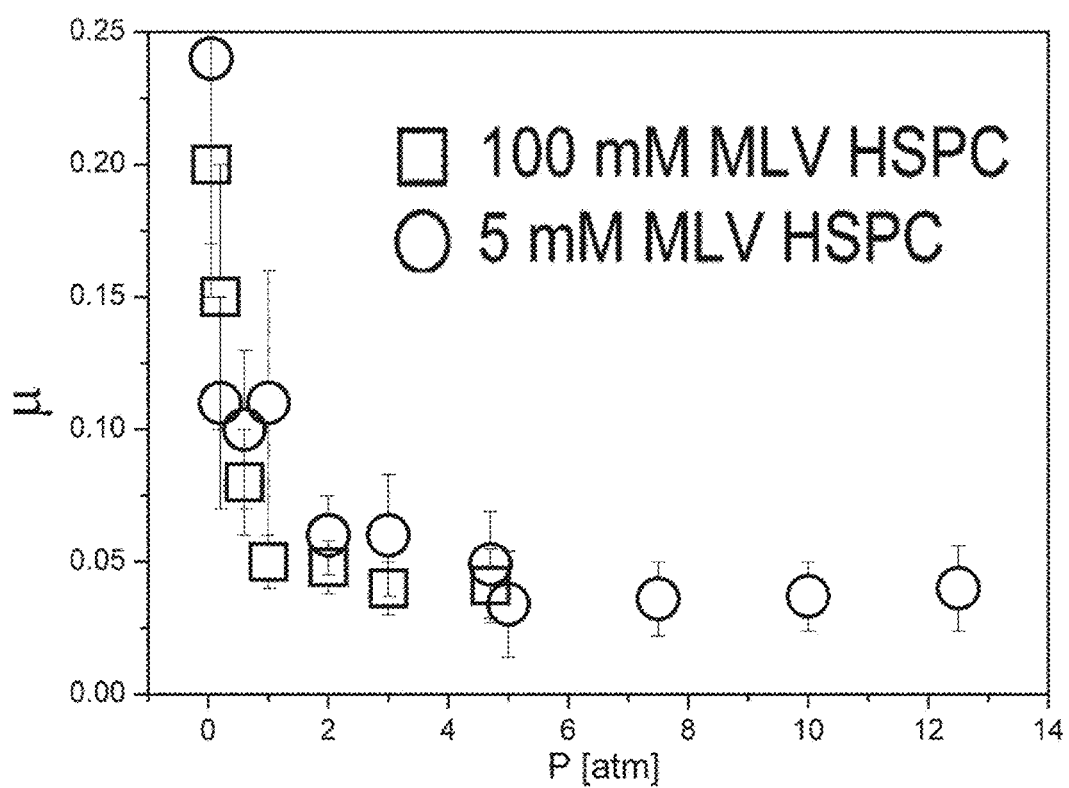
FIG. 9 presents a graph of friction coefficient values as a function of the pressure for different symmetric neat hydrogel sample systems, for the case where liposomes were dispersed not in the hydrogel but in the surrounding solution around the hydrogel, wherein the results obtained for the HEMA EGDMA 1% neat sample measured in 100 mM MLV HSPC liposome suspension are marked by squares and the results of the HEMA EGDMA 1% neat sample measured in 5 mM MLV HSPC liposome suspension are marked by circles.

FIG. 9 presents a graph of friction coefficient values as a function of the pressure for different symmetric hydrogel sample systems, wherein the results obtained for the HEMA EGDMA 1% neat sample measured in 100 mM MLV HSPC liposome suspension are marked by squares and the results of the HEMA EGDMA 1% neat sample measured in 5 mM MLV HSPC liposome suspension are marked by circles. This experiment was designed to show that when the liposome dispersion is replaced by pure water, the friction coefficient increases to the original values observed between neat hydrogels across water as seen in FIG. 8, demonstrating that liposomes in suspension have no lasting effects in reducing the friction of hydrogels once they are removed.

As can be seen in FIG. 9, the HEMA EGDMA 1% MLV HSPC hydrogels show a superior friction reduction when the liposomes are incorporated into and dispersed throughout the hydrogel (see, FIG. 8) rather than coating the top of the sample, wherein the friction reduction between the hydrogel samples measured in the liposome suspension medium instead of the pure water medium was about 4-5 times higher (μ of about 0.045 for the HEMA EGDMA 1% measured in 5 or 100 mM MLV HSPC liposome suspension), compared to the friction coefficient measured for hydrogel samples which liposomes incorporated therein and measured in pure water (μ of about 0.01 for the HEMA EGDMA 1%+MLV HSPC).

It is noted herein that the friction coefficients measured after rinsing the neat hydrogels that adsorbed liposomes on their surface (rinsing was effected by immersing the samples in pure water overnight and applying direct flow of water thereon for several seconds) were raised to the values obtained for similar hydrogel samples measured in water without being in contact with liposomes (data not shown). These observations indicate that the incorporation of the liposomes into the hydrogel, rather than just being present on or between the hydrogel surfaces, plays an important role in the performance of the compositions according to embodiments of the present invention.

Figure 10:
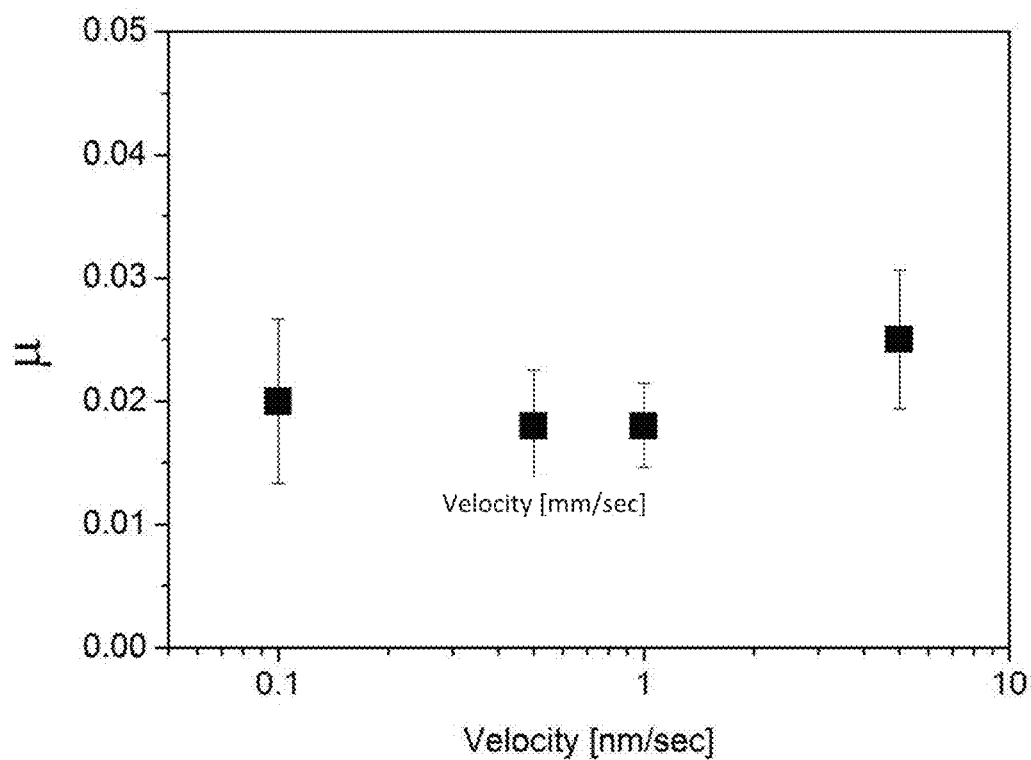
FIG. 10 presents a graph showing the effective friction coefficient as a function of the sliding velocity, as measured in pure water between two HEMA EGDMA 1% hydrogel+

Sliding Velocity Tests:

FIG. 10 presents a graph showing the effective friction coefficient as a function of the sliding velocity, as measured in pure water between two HEMA EGDMA 1% hydrogel+ MLV DSPC under pressure of about 7 atmospheres, while the shear amplitude was 1 mm.

As can be seen in FIG. 10, the friction coefficient is substantially steady (does not change upon changing the shear velocity) over two orders of magnitude of velocities. This result indicates that low friction coefficient values can be expected over a wide range of sliding velocities when a relatively high load is applied between two liposomes/hydrogel compositions, according to embodiments of the present invention.

Table 5 presents the results of the gel-to-gel friction coefficient measurements for HEMA EGDMA 1% neat hydrogel sample pairs and HEMA EGDMA 1% hydrogel sample pair containing different types of MLV liposomes at a concentration of 45 mM: DMPC, DPPC, HSPC and DSPC. Data is based on two independent measurements for each pair of hydrogels. The left column represents the applied external load (in grams and the corresponding calculated pressure at the contact point under the given load. In this flat-to-flat system configuration, the pressure P was calculated by applying $P=F_N/A$ where A is the contact area of the smaller surface among the two discs, having a diameter of about 6 mm.

In order to investigate the effect of adding liposomes to hydrogel on the hydrogel's friction coefficient, all hydrogel samples were measured using varying range of loads, corresponding to varying range of pressures. The different loads that were used were 40 grams, 150 grams, 500 grams, 1000 grams, and higher loads, wherein the highest load was limited by the breaking point of the hydrogel sample.

The pressure at each contact point was calculated according to the following method: when pressing the gel against the metal head formed an imprint on the hydrogel sample surface, typically in the high load tests, the radius r of the imprint was measured and the pressure was calculated as $P=F_N/\pi r^2$, where $F_N$ is the known applied normal load.

For the low load tests wherein no visible imprint was detected, geometrical calculations were applied to estimate the contact area as illustrated in FIGS. 11A-B.

FIGS. 11A-B presents a schematic illustration of the gel-to-metal friction measurement geometry, wherein "r" is defined as the radius of the contact area, also from geometry $r^2=\Delta(22-\Delta)$, where $\Delta$ is the difference in the height of the indented hydrogel (FIG. 11A) comparing to the zero position prior to applying the normal force (FIG. 11B), whereas $\Delta$ was measured for each of the applied normal loads, and the pressure P was calculated accordingly.

Typically, after shearing a hydrogel under high loads, an imprint appeared in the surface of the sample. Since the upper surface is a ball (and not a flat surface), the pressure at the contact point is not uniform, and has a certain distribution. Whenever an imprint has appeared, the size of

TABLE 5

| | Friction Coefficient | | | | |
|---|---|---|---|---|---|
| Hydrogel grams/atmospheres | HEMA EGDMA 1% neat | HEMA EGDMA 1% MLV DMPC | HEMA EGDMA 1% MLV DPPC | HEMA EGDMA 1% MLV HSPC | HEMA EGDMA 1% MLV DSPC |
| 10/0.034 | 0.55 ± 0.25 | 0.6 ± 0.18 | 0.31 ± 0.086 | 0.28 ± 0.06 | 0.28 ± 0.05 |
| 40/0.14 | 0.19 ± 0.05 | 0.25 ± 0.15 | 0.26 ± 0.067 | 0.093 ± 0.023 | 0.1 ± 0.025 |
| 200/0.7 | — | 0.28 ± 0.13 | 0.17 ± 0.043 | 0.078 ± 0.021 | 0.08 ± 0.016 |
| 400/1.4 | — | — | 0.12 ± 0.032 | 0.051 ± 0.014 | 0.06 ± 0.011 |
| 600/2.1 | — | — | 0.09 ± 0.027 | 0.039 ± 0.01 | 0.05 ± 0.013 |
| 1000/3.5 | — | — | — | 0.023 ± 0.005 | 0.024 ± 0.006 |
| 2000/7 | — | — | — | 0.013 ± 0.004 | 0.015 ± 0.003 |
| 3000/10.4 | — | — | — | 0.01 ± 0.002 | 0.01 ± 0.0022 |

As can be seen in Table 5, shear measurements showed a notable reduction of friction in the HEMA hydrogel samples when liposomes were incorporated therein. The dynamic friction coefficient was calculated from the shear traces as $\mu=F_L/F_N$, where $F_N$ and $F_L$ are the measured normal and lateral forces in the system.

Example 4

Gel-to-Metal Friction Measurements

Hydrogel samples were measured using the tribometer in order to calculate the friction coefficient between the hydrogel sample and a metal head used in artificial hip ball-joint replacements.

the imprint was measured and used to calculate the pressure which formed that specific imprint. It is noted herein that when the pressure at the contact point has such a gradient, there may be a certain pressure value threshold that is required to form a visible depression in the hydrogel sample. However, the maximal pressure at the contact point is still higher, as the value from the imprint is still an average value.

Table 6 presents the pressure estimates for hydrogel samples for loads of 1 to 7 kg, comparing the estimates using the aforementioned $\Delta$ calculation to the estimates based on load imprint in the sample. The values in Table 6 are based on three different measurements from two different gels, having Young's moduli of 1.35±0.75 MPa.

TABLE 6

| Load (kg) | Calculated pressure (atmospheres) | |
|---|---|---|
| | From Δ measurements | From imprint |
| 1 | 5.6 | 5.64 |
| 2 | 7 | 11.3 |
| 3 | 9 | 16.9 |
| 4 | 11 | 22.6 |
| 5 | 12.8 | 28.2 |
| 6 | 15.4 | 34 |
| 7 | 18 | 40 |

The effective friction coefficient μ was measured by applying a certain normal load $F_N$. The tribometer measurements afforded the lateral force $F_L$ from the sliding region in the trace. Dividing the lateral force by the normal force afforded the friction coefficient $\mu=F_L/F_N$.

Sliding Velocity:

The following tables present the friction coefficient values measured between a hydrogel samples having a thickness of about 2 mm to a round metal head. The hydrogel composition is presented in the header row, while each column represents one hydrogel composition.

The testing parameters were as follows: sliding velocity of 1 mm/sec, sliding amplitude of 1.5 mm and dwell time of 5 seconds. Experiments were conducted at room temperature of 25±1° C., unless noted otherwise. The static friction coefficient was obtained from the maximum value of the shear trace (not shown), the kinetic friction coefficient was calculated as the average value at the sliding region, and the results were calculated as the mean of 1-3 independent experiments using a fresh hydrogel sample in each case, and 200 back-and-forth cycles per measurement. The "#" symbol represents measurements where the shear trace exhibited a sawtooth wave form, indicating rigid coupling between the two surfaces. In such cases the improvement in friction reduction due to the inclusion of liposomes in the hydrogel was greater than what is seen in the trace plots since the surfaces stick one to the other, and no sliding motion is present between the two surfaces. In other cases, due to the high loads the hydrogel broke down. Therefore, the "#" represents high friction either due to case of no sliding or/and mechanical failure of the hydrogel.

Figure 12A:
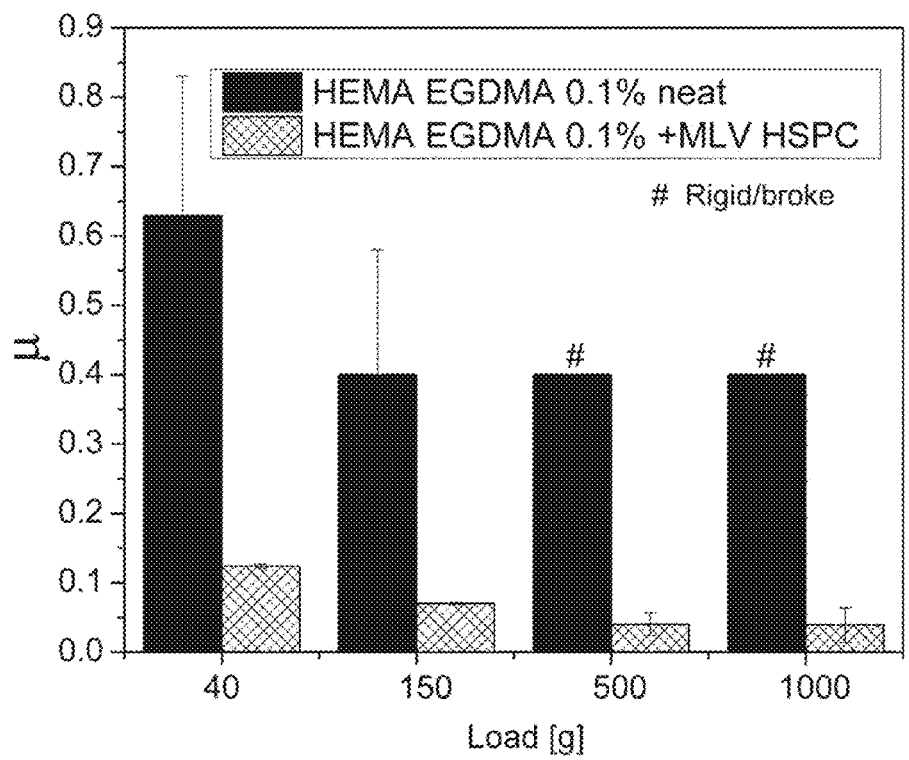
Figure 12B:
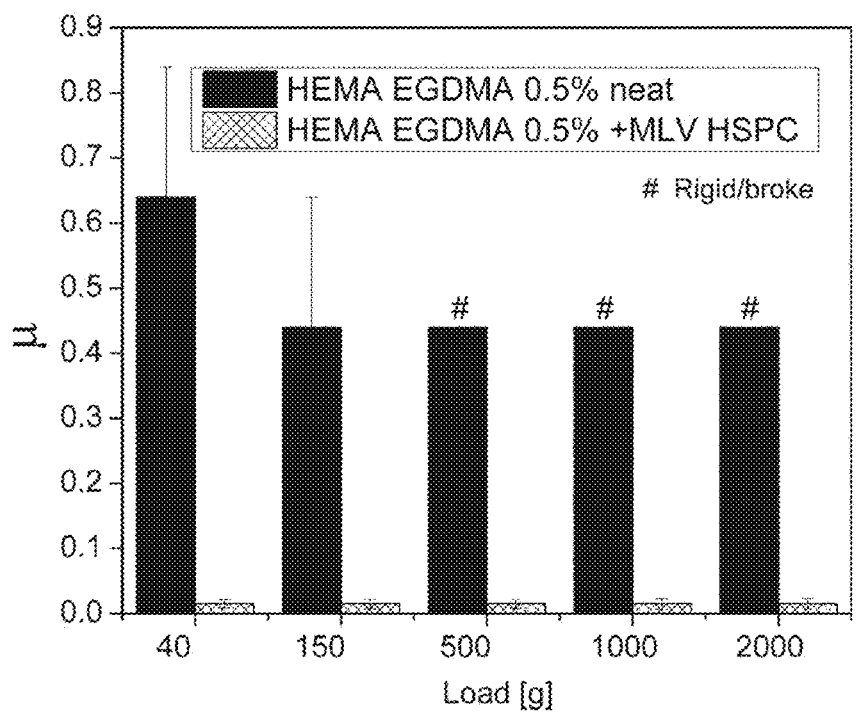

FIGS. 12A-B and Table 7A present the shear reduction results as measured in the gel-to-metal configuration achieved by incorporation of MLV HSPC liposomes into a HEMA EGDMA 0.1% and a HEMA EGDMA 0.5% hydrogels, whereas the "#" symbol indicates a rigid coupling scenario or case of a hydrogel shattering during the experiment.

TABLE 7A

| Load (g) | EGDMA 0.1% Neat | EGDMA 0.1% + MLV HSPC | EGDMA 0.5% Neat | EGDMA 0.5% + MLV HSPC |
|---|---|---|---|---|
| 40 | 0.63 ± 0.23 | 0.12 ± 0.027 | 0.64 ± 0.24 | 0.015 ± 0.006 |
| 150 | 0.4 ± 0.18 | 0.007 ± 0.02 | 0.44 ± 0.21 | 0.015 ± 0.007 |
| 500 | # | 0.004 ± 0.0164 | # | 0.015 ± 0.007 |
| 1000 | | 0.039 ± 0.027 | | 0.015 ± 0.008 |
| 2000 | | # | | 0.015 ± 0.008 |

Figure 12C:
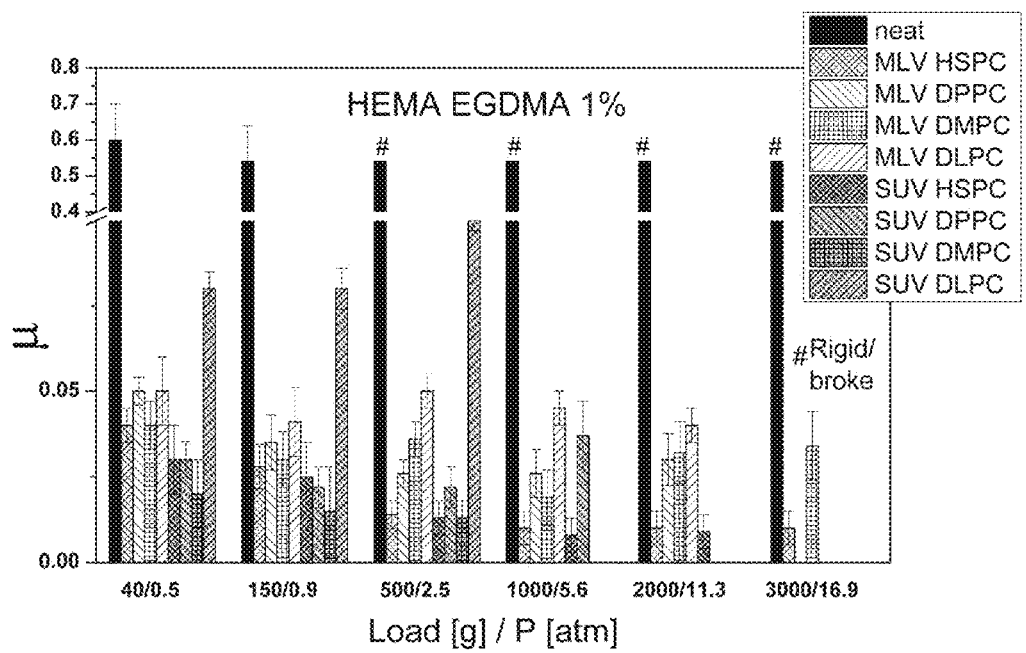

FIG. 12C and Table 7B present the shear reduction results as measured in the gel-to-metal configuration achieved by incorporation of liposomes into a HEMA EGDMA 1%.

TABLE 7B

| Load g/atmospheres | EGDMA 1% Neat | EGDMA 1% + MLV HSPC | EGDMA 1% + MLV DPPC | EGDMA 1% + MLV DMPC | EGDMA 1% + MLV DLPC |
|---|---|---|---|---|---|
| 40/0.6 | 0.65 ± 0.15 | 0.04 ± 0.002 | 0.05 ± 0.002 | 0.04 ± 0.007 | 0.005 ± 0.008 |
| 150/1 | 0.55 ± 0.1 | 0.028 ± 0.0068 | 0.034 ± 0.008 | 0.03 ± 0.008 | 0.041 ± 0.008 |
| 500/2.5 | 0.55 ± 0.1 | 0.014 ± 0.0028 | 0.025 ± 0.0043 | 0.036 ± 0.005 | 0.005 ± 0.008 |
| 1000/5.7 | 0.55 ± 0.1# | 0.011 ± 0.0048 | 0.026 ± 0.008 | 0.019 ± 0.008 | 0.045 ± 0.008 |
| 2000/11.3 | | 0.011 ± 0.005 | | 0.032 ± 0.009 | 0.04 ± 0.005 |
| 3000/16.9 | | 0.011 ± 0.005 | # | 0.034 ± 0.01 | # |

As can be seen in Table 7B, the friction coefficient was reduced by a factor of about 50 under high pressures up to about 17 atmospheres.

Figure 12D:
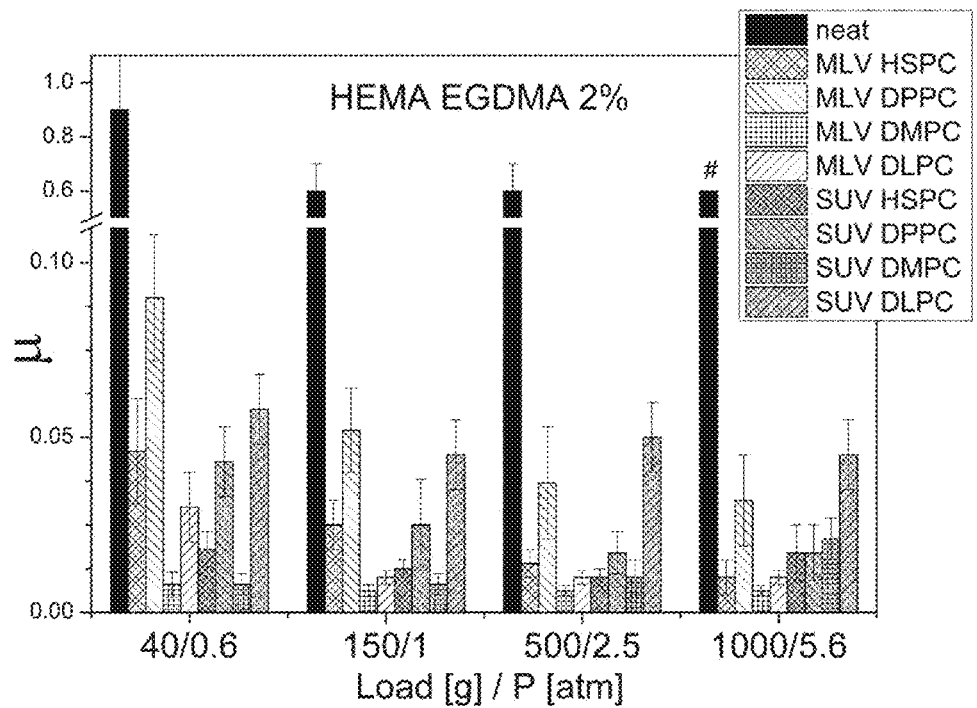
Figure 12E:
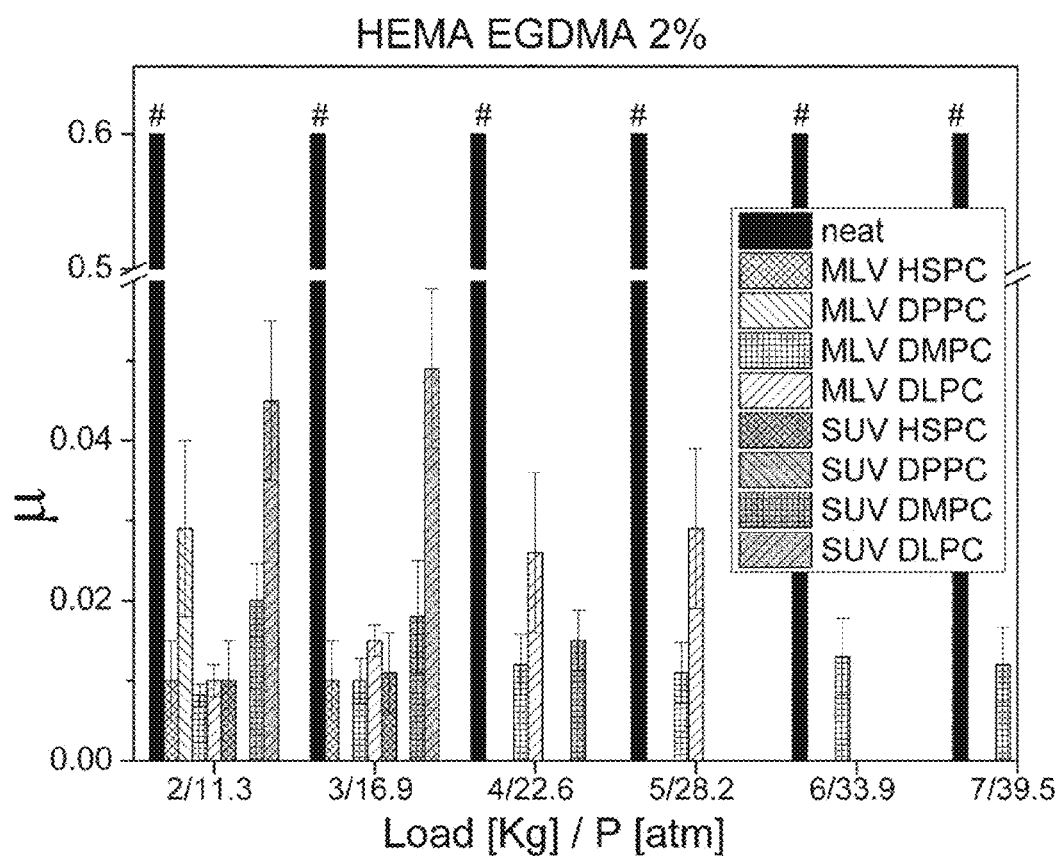

FIGS. 12D-E and Tables 7C-D present the shear reduction results as measured in the gel-to-metal configuration achieved by incorporation of liposomes into a HEMA EGDMA 2%.

TABLE 7C

| Load g/atm | EGDMA 2% Neat | EGDMA 2% + MLV HSPC | EGDMA 2% + MLV DPPC | EGDMA 2% + MLV DMPC | EGDMA 2% + MLV DLPC |
|---|---|---|---|---|---|
| 40/0.6 | 1 ± 0.3 | 0.046 ± 0.015 | 0.09 ± 0.018 | 0.008 ± 0.0036 | 0.03 ± 0.01 |
| 150/1 | 0.66 ± 0.05 | 0.0245 ± 0.007 | 0.052 ± 0.012 | 0.006 ± 0.001 | 0.01 ± 0.002 |
| 500/2.5 | 0.66 ± 0.05 | 0.014 ± 0.004 | 0.037 ± 0.016 | 0.006 ± 0.001 | 0.01 ± 0.002 |
| 1000/5.7 | 0.66 ± 0.05# | 0.01 ± 0.005 | 0.032 ± 0.013 | 0.006 ± 0.001 | 0.01 ± 0.002 |
| 2000/11.3 | # | 0.01 ± 0.005 | 0.029 ± 0.011 | 0.008 ± 0.001 | 0.01 ± 0.002 |
| 3000/16.9 | # | 0.011 ± 0.005 | # | 0.01 ± 0.0028 | 0.015 ± 0.002 |
| 4000/22.6 | | | | 0.012 ± 0.0038 | 0.026 ± 0.01 |
| 5000/28.2 | | | | 0.011 ± 0.0038 | 0.029 ± 0.01 |
| 6000/34 | | | | 0.013 ± 0.0048 | # |
| 7000/39.5 | | | | 0.012 ± 0.0047 | |

TABLE 7D

| Load g/atm | EGDMA 2% Neat | EGDMA 2% + SUV HSPC | EGDMA 2% + SUV DPPC | EGDMA 2% + SUV DMPC | EGDMA 2% + SUV DLPC |
|---|---|---|---|---|---|
| 40/0.6 | 1 ± 0.3 | 0.018 ± 0.005 | 0.043 ± 0.01 | 0.008 ± 0.003 | 0.058 ± 0.01 |
| 150/1 | 0.66 ± 0.05 | 0.0125 ± 0.0026 | 0.025 ± 0.013 | 0.008 ± 0.003 | 0.045 ± 0.01 |
| 500/2.5 | 0.66 ± 0.05 | 0.01 ± 0.0025 | 0.017 ± 0.006 | 0.01 ± 0.005 | 0.05 ± 0.01 |
| 1000/5.7 | 0.66 ± 0.05# | 0.017 ± 0.008 | 0.017 ± 0.008 | 0.021 ± 0.006 | 0.045 ± 0.01 |
| 2000/11.3 | # | 0.01 ± 0.005 | # | 0.02 ± 0.0046 | 0.045 ± 0.01 |
| 3000/16.9 | # | 0.011 ± 0.005 | | 0.018 ± 0.007 | 0.049 ± 0.01 |
| 4000/22.6 | | # | | 0.015 ± 0.0038 | # |
| 5000/28.2 | | | | 0.0135 ± 0.0034 | |

FIGS. 13A-B and Tables 8A-B present respectively the shear reduction results as measured in the gel-to-metal configuration achieved by incorporation of liposomes to the HEMA 9EGDMA 4% hydrogel, measured at 25° C.

TABLE 8A

| Load kg/atms | 9EGDMA 4% neat | 9EGDMA 4% + MLV HSPC | 9EGDMA 4% + MLV DPPC | 9EGDMA 4% + MLV DMPC | 9EGDMA 4% + MLV DLPC |
|---|---|---|---|---|---|
| 1/5.7 | 0.3 ± 0.015 | 0.02 ± 0.008 | 0.03 ± 0.01 | 0.019 ± 0.009 | 0.019 ± 0.01 |
| 2/11.3 | # | 0.013 ± 0.0045 | 0.025 ± 0.01 | 0.015 ± 0.008 | 0.07 ± 0.02 |
| 3/16.9 | | 0.012 ± 0.005 | 0.03 ± 0.01 | 0.03 ± 0.01 | 0.081 ± 0.03 |
| 4/22.6 | | 0.011 ± 0.003 | # | 0.039 ± 0.01 | # |

TABLE 8B

| Load kg/atms | 9EGDMA 4% neat | 9EGDMA 4% + SUV HSPC | 9EGDMA 4% + SUV DPPC | 9EGDMA 4% + SUV DMPC | 9EGDMA 4% + SUV DLPC |
|---|---|---|---|---|---|
| 1/5.7 | # | 0.033 ± 0.01 | 0.02 ± 0.006 | 0.012 ± 0.003 | # |
| 2/11.3 | | 0.026 ± 0.008 | 0.018 ± 0.01 | 0.018 ± 0.009 | |
| 3/16.9 | | 0.03 ± 0.01 | 0.04 ± 0.01 | 0.018 ± 0.008 | |
| 4/22.6 | | # | # | 0.014 ± 0.008 | |
| 5/28.2 | | | | 0.014 ± 0.006 | |

As can be seen in FIGS. 13A-B and Tables 8A-B, the friction coefficient was reduced by a factor of about 20 under high pressures up to about 30 atmospheres.

Liposomes in Hydrogel Versus Lipids in Hydrogel:

In order to demonstrate the effect of liposomes incorporation into hydrogels, according to embodiments of the present invention, compared to the effect of adding the lipids comprising these liposomes (i.e., not in liposome configuration) to a comparable hydrogel, friction measurements were conducted with hydrogels prepared with the corresponding lipids without attempting to form liposomes therewith.

HEMA EGDMA 1% hydrogels were prepared with HSPC lipids rather than HSPC liposomes. The HSPC lipid solution was prepared by dissolving 375 mg HSPC lipid in 10 ml of pure water (the same amount of lipids that was used to prepare MLV HSPC liposomes). Heating, sonication or vortex mixing were not applied.

When subjecting the samples described above to gel-to-metal friction coefficient measurements, the HEMA EGDMA 1% hydrogels prepared with HSPC lipids exhibited an increase of the friction coefficient by a factor of about 5 compared to the results obtained for the corresponding samples prepared with MLV HSPC liposomes (data not shown). For example, the friction coefficient exhibited by the lipid-containing hydrogels was 0.055-0.05, under loads of 1000-2000 grams respectively, compared with values of 0.011/0.011 which were measured for the equivalent HEMA EGDMA 1% containing MLV HSPC liposomes incorporated therein. Moreover, the HEMA EGDMA 1% hydrogel prepared with HSPC lipid suffered a mechanical failure (broke) under a load of 3000 grams after less than 60 seconds, while the equivalent hydrogel sample containing MLV HSPC liposomes sustained the same load for 300 seconds and was whole after the measurement.

Example 5

Friction after Dehydration and Rehydration

Hydrogels were dried by heating to 60° C. in an oven for several days until hydrogels were completely dry, as determined by achieving a constant sample weight for several hours. Thereafter, the fully dehydrated hydrogel samples were rehydrated in pure water by immersion. After the hydrogel samples were fully swollen (hydrated), the samples were subjected to friction measurements in a tribometer, similar to the friction measurements presented hereinabove.

FIGS. 14A-B present a comparative bar-graph, showing shear reduction measured in the gel-to-metal configuration measured for a HEMA EGDMA 2% neat hydrogel (crisscross pattern bars) and for HEMA EGDMA 2% hydrogel+ MLV HSPC liposomes incorporated therein (solid grey bars) (FIG. 14A) and the results obtain for HEMA EGDMA 4% neat (crisscross pattern bars) and HEMA EGDMA 4% hydrogel+MLV HSPC liposomes (solid grey bars) (FIG. 14B), after dehydrating and rehydrating the hydrogels as described herein, wherein the "#" symbol indicates rigid coupling and/or mechanical failure of the sample.

As can be seen in FIG. 14A, the friction coefficient was reduced by a factor of about 30 under high pressures up to about 22 atmospheres between the two types of samples, demonstrating the ability of the compositions, according to embodiments of the present invention, to retain their low friction coefficient after a dehydration/rehydration cycle.

As can be seen in FIG. 14B, the friction coefficient was reduced by a factor of about 50 under high pressures up to about 34 atmospheres between the two types of samples, demonstrating the ability of the compositions, according to embodiments of the present invention, to retain their low friction coefficient after a dehydration/rehydration cycle.

Example 6

Friction Reduction in Medical Applications

Duration of the Effect of Adding Liposomes to Hydrogels:
The hydrogel/liposomes compositions, according to embodiments of the present invention, were tested for their capability to effectively maintain their low friction coefficient over extended periods of time.

Exemplary hydrogel/liposomes compositions, presented in Table 9 below, were measured in the tribometer for time period exceeding 300 seconds to evaluate the capacity of the compositions to reduce friction for extended periods of time.

TABLE 9

| Sample | Load | Result |
| --- | --- | --- |
| Neat HEMA EGDMA 2% hydrogel | 3 kg | Mechanical failure after 5 minutes |
| Neat HEMA 9EGDMA 2% hydrogel | 3 kg | Mechanical failure after 45 minutes |
| HEMA EGDMA2% + MLV HSPC | 3 kg | Sample intact after 1 hour $\mu = 0.015 \pm 0.005$ |
| HEMA 9EGDMA 2% + MLV HSPC | 3 kg | Sample intact after 1 hour $\mu = 0.015 \pm 0.005$ |

As can be seen in Table 9, the incorporation of liposomes into a hydrogel sample not only confers a notable reduction in their friction coefficient, but also confers a notable increase in the length of service (longevity) of the hydrogel, according to embodiments of the present invention.

Reduction of Friction at Human Body Temperature:
To verify that the hydrogel/liposomes compositions according to embodiments of the present invention are useful for biomedical applications, friction coefficients of samples of the exemplary HEMA EGDMA 1%+MLV HSPC hydrogels, were measured in a tribometer under loads ranging from 40 grams to 3 kg, while setting the tribometer thermostat to 37° C. in a gel-to-metal setting as described hereinabove.

Table 10 presents the long-term friction measurements conducted at human body temperatures using the exemplary HEMA EGDMA 1%+MLV HSPC hydrogel samples.

TABLE 10

| Sample | Load | Result |
| --- | --- | --- |
| Neat HEMA EGDMA 1% hydrogel | 2 kg | Mechanical failure after 2400 seconds |
| HEMA EGDMA 1% + MLV HSPC | 2 kg | Sample intact after 1 hour $\mu = 0.009 \pm 0.005$ |

As can be seen in Table 10, until the hydrogel samples experienced mechanical failure due to the high pressure in the system, the friction coefficients exhibited by these hydrogels were similar to those measured for identical samples at 25° C.±1° C.

Example 7

Methacrylamide Hydrogels

Preparation Method:
Neat hydrogels containing 4% crosslinking agent were prepared as follows: a hydrogel-forming monomer, Methacrylamide (2.1 grams), a crosslinking agent 9EGDMA (560 µL, 4% percent to the monomer molar content), and an aqueous solution of the radical initiator agent APS (24 mg, 10 ml) were stirred vigorously for 30 minutes until fully mixed. Thereafter, 50 µL of the catalyst TMEDA was added dropwise to the mixture and the mixture was stirred for 20 seconds and poured into a 6 cm diameter Petri dish. The rinsing procedure followed similar steps as described hereinabove.

The sample based on methacrylamide are referred to herein as MAAm 9EGDMA 4% neat and MAAm 9EGDMA 4%+liposomes, e.g., MAAm 9EGDMA 4%+SUV DMPC.

Friction Reduction Measurements:
The reduction in friction coefficient upon inclusion of SUV DMPC liposome solution within the hydrogel is shown in Table 11 below.

TABLE 11

| Load [g] | MAAm 9EGMA 4% neat | MAAm 9EGMA 4% + SUV DMPC |
| --- | --- | --- |
| 40 | 0.25 ± 0.1 | 0.0155 ± 0.005 |
| 150 | 0.077 ± 0.03 | 0.017 ± 0.005 |
| 300 | 0.075 ± 0.03 | 0.022 ± 0.005 |
| 500 | 0.085 ± 0.03 | 0.014 ± 0.0045 |

Rheological characteristic of a sample of MAAm 9EGDMA 4%+SUV DMPC hydrogel, namely storage and loss moduli, are shown in Table 12.

TABLE 12

| Sample name | G' (Pa) | G" (Pa) |
| --- | --- | --- |
| MAAm 9EGMA 4% neat | $1.2 \times 10^4$ | 864 |
| MAAm 9EGMA 4% + SUV DMPC | $1.64 \times 10^4$ | 808 |

As can be reckoned from the results presented above, the concept of incorporating liposomes into hydrogels is valid for hydrogels of various types. In the case presented above, the MAAm-based hydrogels incorporating liposomes therein exhibited reduction in the friction coefficient of 3-6 fold, compared to the corresponding HEMA-based hydrogel.

Example 8

HEMA Hydrogels with Caprolactone

Preparation Method:
HEMA monomer was mixed with polycaprolactone (PCL, Sigma, Mw=45,000), by heating to 60° C. while stirring until the mixture solution is clear. Thereafter, 9 ml of HEMA mixed with 27 mg of PCL gave a 3% HEMA/PCL mixture, which was diluted by adding more HEMA to achieve a 1% HEMA/PCL mixture.

After cooling the mixture to room temperature, 3 ml from the mixed HEMA/PCL solution was mixed with 24 mg APS, 50 µL EGDMA, 50 µL TMEDA and 2 ml of water or liposome suspension to afford HEMA/PCL hydrogel samples.

Friction Reduction Measurements:

These hydrogels were measured with the tribometer in the gel-to-metal configuration, and the friction reduction results are shown in Table 13.

TABLE 13

| Load [g] | HEMA/PCL 1% EGDMA 1% neat | HEMA/PCL 1% EGDMA 1% + MLV HSPC | HEMA/PCL 3% EGDMA 1% neat | HEMA/PCL 3% EGDMA 1% + MLV HSPC |
|---|---|---|---|---|
| 1000 | 0.27 | 0.012 ± 0.005 | 0.26 | 0.009 ± 0.005 |
| 2000 | # | 0.01 ± 0.003 | # | 0.0108 ± 0.005 |

Table 14 summarizes rheometer measurements of the hydrogels describing the dynamic modulus properties.

TABLE 14

| Sample name | G' (Pa) | G" (Pa) |
|---|---|---|
| HEMA/PCL 1% EGDMA 1% neat | $1.1 \times 10^5$ | $1.9 \times 10^4$ |
| HEMA/PCL 1% EGDMA 1% + MLV HSPC | $1.38 \times 10^5$ | $2.4 \times 10^4$ |
| HEMA/PCL 3% EGDMA 1% neat | $5 \times 10^4$ | $1 \times 10^4$ |
| HEMA/PCL 3% EGDMA 1% + MLV HSPC | $7 \times 10^4$ | $1.34 \times 10^4$ |

As can be reckoned from the results presented above, the concept of incorporating liposomes into hydrogels is valid for hydrogels which include polymers which do not participate in the network but are rather entangled therein. In the case presented above, the incorporating liposomes in HEMA-based hydrogels, containing polycaprolactone which is entangled rather than chemically bound to the hydrogel's network, reduced the friction coefficient by a factor of 20 and more.

Example 9

Hydrogels Containing Liposomes Prepared in Polymer Solution

The results presented below were obtained for HEMA EGDMA 2% hydrogels, which incorporate liposomes which were prepared in a solution of 0.1 mg/ml of hyaluronic acid (HA) (Sigma, Mw of 8,000-15,000 g/mol) rather than in pure water, as described hereinabove.

Table 15 presents the friction coefficient measured between exemplary hydrogel/liposome compositions to a metal head under different loads and pressures at 25° C.

TABLE 15

| Load g/atm | HEMA EGDMA 2% Neat | HEMA EGDMA 2% + MLV | HEMA EGDMA 2% + MLV |
|---|---|---|---|
| 150/1 | 0.66 ± 0.05 | 0.048 ± 0.027 | 0.007 ± 0.002 |
| 500/2.5 | 0.66 ± 0.05 | 0.036 ± 0.02 | 0.006 ± 0.0025 |
| 1000/5.7 | 0.66 ± 0.05# | 0.026 ± 0.013 | 0.0067 ± 0.003 |
| 3000/16.9 | # | 0.022 ± 0.01 | 0.0073 ± 0.003 |
| 5000/28.2 | | 0.028 ± 0.012 | |
| 7000/39.5 | | 0.032 ± 0.013 | |

Table 16 presents the friction coefficient measured between exemplary hydrogel/liposome compositions to a metal head under different loads and pressures at 37° C.

TABLE 16

| Load g/atm | EGDMA 2% Neat | EGDMA 2% + MLV | EGDMA 2% + MLV |
|---|---|---|---|
| 150/1 | 0.66 ± 0.05 | 0.026 ± 0.012 | 0.0076 ± 0.005 |
| 500/2.5 | 0.66 ± 0.05 | 0.036 ± 0.016 | 0.0076 ± 0.005 |
| 1000/5.7 | 0.66 ± 0.05# | 0.03 ± 0.012 | 0.008 ± 0.004 |
| 3000/16.9 | # | 0.046 ± 0.018 | 0.01 ± 0.0046 |

As can be seen in Tables 15 and 16, liposomes prepared in the presence of a polymer, such as HA, were used successfully in reducing the friction coefficient of hydrogels.

Example 10

The Effect of Liposomes Concentration on Friction

The results presented below demonstrate the effect of liposome concentration of the capacity of the liposomes to reduce the friction coefficient of hydrogels, according to embodiments of the present invention. For this purpose, HEMA 9EGDMA 4% hydrogels were prepared as described hereinabove, using stock liposome solutions having various concentrations of SUV DMPC liposomes.

Table 17 presents the results of friction coefficients measurements obtained for hydrogel/liposome composition samples against a metal head under different loads and pressures at 25° C.

TABLE 17

| Load Kg/atm | HEMA 9EGDMA 4% Neat | HEMA 9EGDMA 4% + SUV | HEMA 9EGDMA 4% + SUV | HEMA 9EGDMA 4% + SUV | HEMA 9EGDMA 4% + SUV |
|---|---|---|---|---|---|
| 1/5.6 | 0.3 ± 0.05 | 0.04 ± 0.019 | 0.045 ± 0.017 | 0.03 ± 0.012 | 0.013 ± 0.005 |
| 3/16.9 | | 0.125 ± 0.07 | 0.1 ± 0.07 | 0.039 ± 0.013 | 0.015 ± 0.003 |
| 5/28.2 | | | | 0.045 ± 0.019 | 0.014 ± 0.008 |

As can be seen in Table 17, augmenting the concentration of liposomes in the hydrogel/liposomes compositions, according to embodiments of the present invention, had a notable impact on their capacity to reduce the friction coefficients of the tested compositions. In the low concentration range of 1.6 to 6 mM, a reduction in the friction coefficient by a factor ranging from 7.5 to 10, respectively, was observed. A far more notable reduction by a factor of 60 was observed for the sample prepared with 12 nM liposomes, indicating a non-linear and possibly cumulative effect of several combined factors which change along with the liposome concentration, such as the water inclusion/exclusion, density and the likes.

Example 11

The Effect of Hydrogels' Crosslinking on Friction

The experiment described below was designed to study the effect of the degree of crosslinking on the capacity of liposomes to reduce the friction coefficient of hydrogels. Thus, HEMA hydrogels having a 60:40 HEMA:water ratio were prepared with 0.2% EGDMA and SUV DMPC liposomes having an average diameter of 80±20 nm at a concentration of about 2 mM. An corresponding neat hydrogel was prepared as control, and the samples were subjected to shear measurements under loads of 500 grams to 1 Kg and higher.

The results showed that both neat and HEMA EGDMA0.2+SUV DMPC hydrogels were in rigid coupled over the entire range of loads, showing similar friction coefficients for both hydrogels. These results indicate that at such low degree of crosslinking and liposome size, no enhanced shear reduction of the hydrogel was obtained.

Example 12

Wear Measurements

The exemplary neat HEMA EGDMA 2% and the exemplary corresponding hydrogel having DMPC MLV liposomes incorporated therein were subjected to long run friction measurements. The hydrogels were rubbed back and forth at amplitude of 1.5 mm against a metal head in a water bath at 25° C.

A capacitance probe was connected at all times during the shear measurements and monitored and recorded the height of the sample.

FIG. 15 presents a photograph of a sample of neat HEMA EGDMA 2% hydrogel (right-hand side) and an exemplary HEMA EGDMA 2% hydrogel containing DMPC MLV liposomes (left-hand side), according to some embodiments of the present invention, which have been subjected to a load of 5 Kg against a metal head in pure water at a temperature of 25° C.

As can be seen in FIG. 15, the neat HEMA EGDMA 2% hydrogel crushed after about 6 minutes while the HEMA EGDMA 2% hydrogel having DMPC MLV liposomes incorporated therein sustained the measurement and was intact after 60 minutes experiment.

The height of the exemplary sample of HEMA EGDMA 2% hydrogel having DMPC MLV liposomes incorporated therein decreased by only 14.5 microns at the end of the 60 minutes run.

Wear tests were performed under lower normal load of 1 kg which was applied on different hydrogel samples while shearing against a metal head in pure water at T=25° C. for 2 hours, and the results are presented in FIG. 16.

FIG. 16 presents a photograph of a sample of neat HEMA EGDMA 2% hydrogel (right-hand side), an exemplary HEMA EGDMA 2% hydrogel containing MLV HSPC liposomes (center), and an exemplary HEMA EGDMA 2% hydrogel containing MLV DMPC liposomes (left-hand side), according to some embodiments of the present invention, which have been subjected to a load of 1 Kg against a metal head in pure water at a temperature of 25° C.

The wear of the neat HEMA hydrogel sample was higher (57 microns; not shown) compared to the corresponding sample having HSPC MLV liposomes incorporated therein (12 microns; not shown) and the sample having DMPC MLV liposomes incorporated therein (no wear) hydrogels.

Example 13

The rheological and tribological properties of HEMA hydrogels with MLV hydrogenated soy phosphatidylcholine (HSPC) and MLV DMPC liposomes, which were prepared in the presence of a polymer prior to the hydrogel-encapsulation step, were tested.

The exemplary polymers used in the preparation of the liposomed were poly(2-hydroxyethyl methacrylate) (pHEMA), alginate and hyaluronic acid.

Materials:

Water used was purified Barnsted NanoPure systems to 18.2 MΩ cm resistance with total organic content levels of less than about 1 ppb. All phosphatidylcholines lipids were purchased from lipoid, GmbH. 2-hydroxyethyl methacrylate (HEMA), ammonium persulfate (APS), N,N,N',N'-tetramethylethylenediamine (TMEDA), ethylene glycol methacrylate (EGDMA) were purchased from Sigma-Aldrich and used as received. All polymers, poly(2-hydroxyethyl methacrylate) (pHEMA) of average Mw of 20,000 g/mol, hyaluronic acid sodium salt from rooster comb and alginic acid sodium salt from brown algae medium viscosity, were purchased from Sigma-Aldrich.

Liposomes Preparation:

Multilamellar vesicles (MLV) composed of 1,2-dimyristoyl-sn-glycero-3-phosphocholine (DMPC) and HSPC were prepared by hydrating the lipids in at least 5° C. above the lipid $T_M$, followed by sonication. Where liposomes were prepared in the presence of a polymer, the polymer solution was prepared in advance at a polymer concentration of 1 mg/1 ml, and after full dissolution of the polymer, the polymer solution was heated at least 5° C. above the lipid $T_M$ and added to the lipids, followed by mixing.

Hydrogel Preparation:

Neat hydrogels containing 2% (molar percent with respect to the monomer) crosslinking agent were prepared as follows: HEMA (3.2 g), EGDMA (100 mg) and APS aqueous solution (2 ml, 53 mM) were vigorously stirred for 30 minutes until fully mixed. TMEDA (50 µl) was added to the mixture, stirred for 20 seconds and poured into a 6 cm diameter petri dish. The gels were allowed to crosslink over 4-5 hours, followed by rinsing in distilled water for 3 days to remove unreacted materials. The obtained gels, referred to as HEMA EGDMA 2%, were cut into pieces for tribological tests and other characterization methods. Liposome-loaded hydrogels were prepared similarly. The APS aqueous solution was replaced by a liposome suspension with the same APS content.

Liposome Size and Zeta Potential Measurements:

Size and zeta potential of the different liposomes in pure water and in different polymer solutions at concentration of 1 mg/ml were determined using the Malvern Zetasizer. Briefly, Zeta (ξ) potential is a measure of the surface electrical charge of particles, and is often being used to characterize colloids. Zeta (ξ) absolute value 5 mV or higher indicates on a charged surface of the colloid, which corresponds to stable colloidal dispersion as a result from repealing interactions between two colloids.

Table 18 presents Zeta potential measurements of the different polymer solutions in pure water and when mixed with DMPC and HSPC liposomes, as measured for neat HEMA EGDMA 2% hydrogel, HEMA EGDMA 2%+MLV HSPC 45 mM and HEMA EGDMA 2%+MLV DMPC 45 mM.

TABLE 18

Zeta potential values for the neat polymer and the mixed polymer/liposome solutions

| polymer | Neat hydrogel | +MLV HSPC 45 mM | +MLV DMPC 45 mM |
|---|---|---|---|
| pHEMA | −20 ± 5 mV | zero | zero |
| Alginate | −50 ± 12 mV | −16 ± 7 mV | −19 ± 7 mV |
| HA | −30 ± 5 mV | zero | zero |

As can be seen in Table 18, MLV's with pHEMA or HA polymer dispersions showed a zero value of ξ (meaning |ξ|<5 mV) as MLV's with alginate showed a negatively charged zeta (Table 1).

Size measurements of the samples indicates that the MLV DMPC liposomes in pure water have three populations of $D_1=35\pm5$ nm, $D_2=122\pm14$ nm and $D_3=570\pm79$ nm. DLS data of the MLV HSPC liposomes showed $D=550\pm100$ nm.

Table 19 presents DLS measurements of the various MLV HSPC and MLV DMPC liposome suspensions in pure water and in different polymers.

TABLE 19

| DLS measurement | MLV HSPC | MLV DMPC |
|---|---|---|
| pure water | 540 ± 100 nm | 35 ± 5 nm, 122 ± 14 nm, 570 ± 79 nm |
| pHEMA | 474 ± 60 nm | — |
| Alginate | 635 ± 135 nm | 622 ± 250 nm |
| HA | 580 ± 230 nm | 180 ± 75 nm, 630 ± 190 nm |

As can be seen in Table 19, mixing MLV DMPC with HA and alginate as polymers result in smaller particle size, as the population of size of 35±5 nm disappeared upon mixing. The difficulty in measuring the size of the pHEMA/MLV DMPC suspension indicates a plurality of size populations.

Cryo-SEM Freeze Fracture Imaging:

Fresh samples were flash frozen to afford cryofixation, and then fractured by breaking the solid sample while maintained at liquid nitrogen temperature. The cold fractured surface sometimes "etched" by increasing the temperature to about −100° C. for several minutes to let some ice sublime.

The neat HEMA EGDMA 2% sample, the HEMA EGDMA 2%+MLV DMPC/polymer sample and the HEMA EGDMA 2%+MLV HSPC/polymer sample were imaged. These freeze fracture images of the hydrogel with liposomes/polymer showed no significantly different from the freeze fracture images of the HEMA with liposomes prepared with no added polymer for each of the liposome type (images not shown).

Dynamic Mechanical Characterization of Hydrogels:

Samples were subjected to a strain sweep test in which they were deformed at different shear strains, and the moduli were recorded to define the linear viscoelastic zone in which the modulus G' is independent of the applied strain. Each sample was then subjected to a frequency sweep test. A sinusoidal deformation of constant peak amplitude was applied over the range of frequencies from 0.05-100 Hz under a stress of 50 Pa at 25° C.

Table 20 presents the result of the frequency sweep test of a HEMA EGDMA 2% hydrogels.

TABLE 20

| HEMA EGDMA 2% | Pure water | | pHEMA | | Alginate | | HA | |
|---|---|---|---|---|---|---|---|---|
|  | +HSPC | +DMPC | +HSPC | +DMPC | +HSPC | +DMPC | +HSPC | +DMPC |
| G' [Pa] | $6.3 \times 10^4$ | $6.2 \times 10^4$ | $1.3 \times 10^5$ | $1.1 \times 10^5$ | $7.8 \times 10^4$ | $7.4 \times 10^4$ | $4.2 \times 10^4$ | $3.2 \times 10^4$ |
| G'' [Pa] | $1.3 \times 10^4$ | $1 \times 10^4$ | $2.7 \times 10^4$ | $8 \times 10^3$ | $2 \times 10^4$ | $1.2 \times 10^4$ | $6.5 \times 10^3$ | $5.2 \times 10^3$ |

As can be seen in Table 20, the storage shear modulus, G' was higher than the loss shear modulus, over the entire frequency region indicating that the elastic response of the material is stronger than the viscous response, representative of a solid-like behavior. The storage modulus was fairly constant throughout the entire frequency range, although a slight increase is observed with increasing frequency.

Friction Measurements Gel Vs. Metal Head:

Friction tests were carried out using a CETR© tribometer, UMT model with a high sensor which enables application of high normal loads. HEMA hydrogels were measured using the tribometer in order to calculate the friction coefficient between the hydrogel to a metal head used in artificial hip joint replacements.

In order to investigate the hydrogels' friction coefficient, all hydrogels were measured using varying range of loads, corresponding to varying range of pressures. The different loads that were used were: 40 g, 150 g, 500 g, 1000 g, and also higher loads—the highest load was limited by the breaking point of the hydrogel. The pressure at each contact point was calculated as described hereinabove. The effective friction coefficient μ was measured by applying a certain normal load $F_N$ and using the tribometer obtained directly the lateral force $F_L$ from the sliding region in the trace. Dividing the lateral force by the normal force affords the friction coefficient $\mu=F_L/F_N$.

The testing parameters were as follows: sliding velocity of 1 mm/sec, sliding amplitudes of 1-1.5 mm and dwell time of 5 seconds. Experiments were conducted at temperature of 37±1° when samples were immersed in pure water. The kinetic friction coefficient was calculated as the average value at the sliding region, and the results were calculated as the mean of 2-5 independent experiments using a fresh hydrogel sample in each case, and 300 back-and-forth cycles per measurement.

FIG. 17 presents a comparative bar plot of the effective friction coefficients measured for neat HEMA hydrogel, and for various exemplary HSPC liposome-encapsulating HEMA hydrogels, according to some embodiments of the present invention, comparing the effect of adding MLV HSPC liposomes prepared with and without the presence of a polymer on the friction coefficient (μ).

Unless stated otherwise, the "#" symbol used in any of the figures presented in this document represents measurements where the shear trace exhibited a sawtooth wave form, indicating rigid coupling between the two surfaces. In such cases the improvement in friction reduction due to the inclusion of liposomes in the hydrogel was greater than what is seen in the trace plots since the surfaces stick one to the other, and no sliding motion is present between the two surfaces. In other cases, due to the high loads the hydrogel broke down. Therefore, the "#" represents high friction either due to case of no sliding or/and mechanical failure of the hydrogel.

FIG. 18 presents a comparative bar plot of the effective friction coefficients measured for neat HEMA hydrogel, and for various exemplary DMPC liposome-encapsulating HEMA hydrogels, according to some embodiments of the present invention, comparing the effect of adding MLV DMPC liposomes prepared with and without the presence of a polymer on the friction coefficient (μ).

As can be seen FIG. 18, when HEMA hydrogels were prepared with MLV DMPC prepared in the presence of a polymer, the effect of the polymer was to lower the friction coefficient, and improved the lubrication capabilities of these hydrogels when measured at 37° C. in pure water.

Moreover, the addition of DMPC/polymer complexes to the HEMA hydrogels resulted in a tendency of the hydrogel to sustain much higher pressures in comparison to the hydrogels containing MLV DMPC liposomes (without a polymer). The HEMA hydrogels with MLV DMPC broke after increasing the pressure above 16.9 atm while the HEMA hydrogels with MLV DMPC with pHEMA/HA sustain much higher pressures up to 39.5/28.2 atm, respectively.

Table 21 and Table 22 summarize the results of the friction coefficient measurements described hereinabove for the DMPC MLV and the HSPC MLV liposomes respectively, comparing hydrogel containing the same while prepared with and without the presence of various polymers, according to some embodiments of the present invention.

TABLE 21

| Load [Kg]/ P [atm] | neat | +MLV DMPC | +MLV DMPC/ pHEMA | +MLV DMPC/ HA | +MLV DMPC/ Alginate |
| --- | --- | --- | --- | --- | --- |
| 0.15/1 | 0.6 ± 0.05 | 0.03 ± 0.01 | 0.017 ± 0.005 | 0.03 ± 0.005 | 0.008 ± 0.005 |
| 0.5/2.3 | 0.6 ± 0.05 | 0.033 ± 0.01 | 0.017 ± 0.005 | 0.022 ± 0.005 | 0.007 ± 0.005 |
| 1/5.6 | | 0.035 ± 0.01 | 0.017 ± 0.005 | 0.027 ± 0.005 | 0.006 ± 0.005 |
| 3/16.9 | | 0.035 ± 0.01 | 0.025 ± 0.005 | 0.022 ± 0.005 | 0.0074 ± 0.005 |
| 5/28.2 | | | 0.024 ± 0.005 | 0.02 ± 0.005 | |
| 7/39.5 | | | 0.023 ± 0.005 | | |

TABLE 22

| Load [Kg]/ P [atm] | neat | +MLV HSPC | +MLV HSPC/ pHEMA | +MLV HSPC/ HA | +MLV HSPC/ Alginate |
| --- | --- | --- | --- | --- | --- |
| 0.15/1 | 0.6 ± 0.05 | 0.01 ± 0.005 | 0.06 ± 0.005 | 0.021 ± 0.005 | 0.027 ± 0.005 |
| 0.5/2.3 | 0.6 ± 0.05 | 0.0118 ± 0.005 | 0.039 ± 0.005 | 0.014 ± 0.005 | 0.02 ± 0.005 |
| 1/5.6 | | 0.014 ± 0.005 | 0.022 ± 0.005 | 0.021 ± 0.005 | 0.05 ± 0.005 |
| 3/16.9 | | 0.016 ± 0.005 | 0.024 ± 0.005 | 0.025 ± 0.005 | 0.044 ± 0.005 |

Wear Measurements:

Neat HEMA EGDMA 2%, HEMA EGDMA 2%+MLV DMPC and HEMA EGDMA 2% encapsulating MLV DMPC prepared in the presence of pHEMA (HEMA EGDMA 2%+MLV DMPC/pHEMA), according to some embodiments of the present invention, were subjected to long run friction measurements. The hydrogels were rubbed back and forth at amplitude of 1.5 mm against a metal head in a water bath at 37°. A capacitance probe was connected all time during the shear measurements and monitored and recorded the height of the sample. The neat hydrogel exhibited continues reduction in the height of the sample, and during 44 minutes of sliding, before the sample was crushed, a reduction of about 100 microns was recorded. The HEMA EGDMA 2%+MLV DMPC/pHEMA sample showed a remarkable resistance to wear as during the first 60 minutes of shearing the reduction of the height of the sample was of only about 3 microns. The friction coefficient of the HEMA EGDMA 2%+MLV DMPC/pHEMA sample during 2 hours of shearing was of 0.015±0.005, and the sample remained intact. The HEMA EGDMA 2%+MLV DMPC sample showed a reduction of about 100 microns in height of the sample after 1 hour of measurement. The friction coefficient during 1 hour of measurement was of 0.04±0.015, and after about 71 minutes the sample broke.

Example 14

The effect of the level of crosslinking of hydrogels containing different concentrations of SUV or MLV liposomes, on the friction coefficient μ of the hydrogel/liposome composition was investigated at different temperatures T=25° C. and T=37° C.

Neat HEMA hydrogels containing 2%, 1%, 0.22% and 0.1% (molar percent with respect to the monomer) crosslinking agent were prepared as follows: HEMA (3.2 g), EGDMA (100 mg, 50 mg, 11 mg, and 5 mg) and APS aqueous solution (2 ml, 53 mM) were vigorously stirred for 30 minutes until fully mixed. TMEDA (50 μl) was added to the mixture, stirred for 20 seconds and poured into a 6 cm diameter petri dish. The gels were allowed to cure over 4 hours, followed by rinsing in distilled water for 3 days to remove unreacted materials.

The obtained gels were cut into pieces for tribological tests and other characterization methods. Liposome-loaded hydrogels were prepared similarly. The APS aqueous solution was replaced by a liposome suspension with the same APS content.

Varying Concentration of Small Unilammelar Vesicles (SUVs):

HEMA hydrogels containing different concentrations of SUV DMPC and SUV HSPC (diameter range from 56-70 nm for the SUV DMPC, and 76-116 nm for the SUV HSPC liposomes) liposomal hydrogels ranging from zero (neat hydrogel) to 12 mM were prepared as described hereinabove. Due to differences in the molecular weights of the DMPC and the HSPC lipids, the same liposome concentration in the hydrogel dictates different weight/volume ratios for these two lipids.

FIGS. 19-22 present the results of the friction coefficient measurements conducted for various HEMA hydrogels containing SUV liposomes against a metal head under different loads and temperature.

FIG. 19 presents a comparative bar-plot, showing the results of the friction coefficient measurements conducted at 25° C. for neat HEMA EGDMA 0.22% and HEMA EGDMA 0.22%+SUV DMPC or HSPC at a liposome concentrations of 2 mM, 4 mM and 12 mM.

FIG. 20 presents a comparative bar-plot, showing the results of the friction coefficient measurements conducted at 25° C. for neat HEMA EGDMA 1% and HEMA EGDMA 1%+SUV DMPC or HSPC at a liposome concentrations of 2 mM and 12 mM.

FIG. 21 presents a comparative bar-plot, showing the results of the friction coefficient measurements conducted at 37° C. for neat HEMA EGDMA 0.22% and HEMA EGDMA 0.22%+SUV DMPC or HSPC at a liposome concentrations of 2 mM, 4 mM and 12 mM.

FIG. 22 presents a comparative bar-plot, showing the results of the friction coefficient measurements conducted at 37° C. for neat HEMA EGDMA 1% and HEMA EGDMA 1%+SUV DMPC or HSPC at a liposome concentrations of 2 mM and 12 mM.

The results of the friction coefficient measurements described hereinabove are summarized in Tables 23-26 below.

TABLE 23

| | | | HEMA hydrogels EGDMA = 0.22% | | | | | |
|---|---|---|---|---|---|---|---|---|
| T = 25° | | neat | SUV DMPC | | | SUV HSPC | | |
| Load [Kg] | | 0 mM | 2 mM | 4 mM | 12 mM | 2 mM | 4 mM | 12 mM |
| 0.04 | | 0.2 ± 0.01 | 0.12 ± 0.01 | 0.014 ± 0.005 | 0.017 ± 0.003 | 0.2 ± 0.01 | 0.015 ± 0.005 | 0.022 ± 0.005 |
| 0.15 | | 0.5 ± 0.01 | 0.47 ± 0.01 | 0.017 ± 0.005 | 0.016 ± 0.003 | | 0.016 ± 0.005 | 0.022 ± 0.005 |
| 0.5 | | | | | | | 0.013 ± 0.005 | 0.02 ± 0.005 |

TABLE 24

| | | HEMA hydrogels EGDMA = 1% | | | | |
|---|---|---|---|---|---|---|
| T = 25° | | neat | SUV DMPC | | SUV HSPC | |
| Load [Kg] | | 0 mM | 2 mM | 12 mM | 2 mM | 12 mM |
| 0.04 | | 0.27 ± 0.008 | 0.02 ± 0.005 | 0.0058 ± 0.003 | 0.039 ± 0.005 | 0.037 ± 0.005 |
| 0.15 | | 0.33 ± 0.009 | 0.015 ± 0.005 | 0.0046 ± 0.003 | 0.021 ± 0.005 | 0.029 ± 0.005 |
| 0.5 | | | 0.067 ± 0.005 | 0.0075 ± 0.005 | 0.02 ± 0.005 | 0.029 ± 0.005 |

TABLE 24-continued

| | HEMA hydrogels EGDMA = 1% | | | | |
|---|---|---|---|---|---|
| T = 25° | neat | SUV DMPC | | SUV HSPC | |
| Load [Kg] | 0 mM | 2 mM | 12 mM | 2 mM | 12 mM |
| 1 | | 0.042 ± 0.005 | 0.0085 ± 0.005 | | 0.02 ± 0.005 |
| 3 | | | 0.013 ± 0.005 | | |

TABLE 25

| | HEMA hydrogels EGDMA = 0.22% | | | | | | |
|---|---|---|---|---|---|---|---|
| T = 37° | neat | SUV DMPC | | | SUV HSPC | | |
| Load [Kg] | 0 mM | 2 mM | 4 mM | 12 mM | 2 mM | 4 mM | 12 mM |
| 0.04 | 0.183 ± 0.007 | 0.3 ± 0.009 | 0.2 ± 0.007 | 0.03 ± 0.007 | 0.08 ± 0.005 | 0.03 ± 0.005 | 0.068 ± 0.005 |
| 0.15 | 0.32 ± 0.01 | 0.21 ± 0.009 | 0.25 ± 0.007 | 0.085 ± 0.007 | 0.095 ± 0.005 | 0.08 ± 0.005 | 0.064 ± 0.005 |
| 0.5 | | | 0.19 ± 0.007 | 0.26 ± 0.007 | 0.107 ± 0.005 | 0.044 ± 0.005 | 0.054 ± 0.005 |
| 1 | | | 0.15 ± 0.007 | 0.2 ± 0.007 | 0.07 ± 0.005 | 0.057 ± 0.005 | 0.056 ± 0.005 |

TABLE 26

| | HEMA hydrogels EGDMA = 1% | | | | |
|---|---|---|---|---|---|
| T = 37° | neat | SUV DMPC | | SUV HSPC | |
| Load [Kg] | 0 mM | 2 mM | 12 mM | 2 mM | 12 mM |
| 0.04 | 0.272 ± 0.01 | 0.3 ± 0.008 | 0.0033 ± 0.003 | 0.047 ± 0.005 | 0.07 ± 0.005 |
| 0.15 | 0.34 ± 0.01 | 0.2 ± 0.009 | 0.003 ± 0.003 | 0.03 ± 0.005 | 0.07 ± 0.005 |
| 0.5 | | | 0.015 ± 0.005 | 0.032 ± 0.005 | 0.06 ± 0.005 |
| 1 | | | 0.038 ± 0.005 | 0.022 ± 0.005 | 0.06 ± 0.005 |

Varying Concentration of Multilamellar Vesicles (MLVs):

HEMA hydrogels were prepared with different MLV HSPC and MLV DMPC liposome concentration that were incorporated inside the hydrogels as described hereinabove.

FIGS. 23-28 present the results of the friction coefficient measurements conducted for various HEMA hydrogels containing MLV liposomes against a metal head under different loads and temperature.

FIG. 23 presents a comparative bar-plot, showing the results of the friction coefficient measurements conducted at 25° C. for neat HEMA EGDMA 0.1% and HEMA EGDMA 0.1%+MLV DMPC or HSPC at a liposome concentrations of 2 mM and 18 mM.

FIG. 24 presents a comparative bar-plot, showing the results of the friction coefficient measurements conducted at 25° C. for neat HEMA EGDMA 1% and HEMA EGDMA 1%+MLV DMPC or HSPC at a liposome concentrations of 0.4 mM, 2 mM and 18 mM.

FIG. 25 presents a comparative bar-plot, showing the results of the friction coefficient measurements conducted at 25° C. for neat HEMA EGDMA 2% and HEMA EGDMA 2%+MLV DMPC or HSPC at a liposome concentrations of 2 mM and 18 mM.

FIG. 26 presents a comparative bar-plot, showing the results of the friction coefficient measurements conducted at 37° C. for neat HEMA EGDMA 0.1% and HEMA EGDMA 0.1%+MLV DMPC or HSPC at a liposome concentrations of 2 mM and 18 mM.

FIG. 27 presents a comparative bar-plot, showing the results of the friction coefficient measurements conducted at 37° C. for neat HEMA EGDMA 1% and HEMA EGDMA 1%+MLV DMPC or HSPC at a liposome concentrations of 0.4 mM, 2 mM and 18 mM.

FIG. 28 presents a comparative bar-plot, showing the results of the friction coefficient measurements conducted at 37° C. for neat HEMA EGDMA 2% and HEMA EGDMA 2%+MLV DMPC or HSPC at a liposome concentrations of 2 mM and 18 mM.

TABLE 27

| | HEMA hydrogels EGDMA = 0.1% | | | | |
|---|---|---|---|---|---|
| T = 25° | neat | MLV DMPC | | MLV HSPC | |
| Load [Kg] | 0 mM | 2 mM | 18 mM | 2 mM | 18 mM |
| 0.04 | 0.2 ± 0.01 | 0.059 ± 0.005 | 0.068 ± 0.005 | 0.04 ± 0.005 | 0.035 ± 0.005 |
| 0.15 | 0.2 ± 0.01 | 0.095 ± 0.005 | 0.066 ± 0.005 | 0.159 ± 0.01 | 0.033 ± 0.005 |

TABLE 27-continued

| | HEMA hydrogels EGDMA = 0.1% | | | | |
|---|---|---|---|---|---|
| T = 25° | neat | MLV DMPC | | MLV HSPC | |
| Load [Kg] | 0 mM | 2 mM | 18 mM | 2 mM | 18 mM |
| 0.5 | | 0.142 ± 0.03 | 0.058 ± 0.005 | | 0.07 ± 0.008 |
| 1 | | | | | 0.045 ± 0.005 |

TABLE 28

| | HEMA hydrogels EGDMA = 1% | | | | |
|---|---|---|---|---|---|
| T = 25° | neat | MLV DMPC | | MLV HSPC | |
| Load [Kg] | 0 mM | 2 mM | 18 mM | 2 mM | 18 mM |
| 0.04 | 0.27 ± 0.008 | 0.0152 ± 0.008 | 0.011 ± 0.005 | 0.014 ± 0.005 | 0.04 ± 0.006 |
| 0.15 | 0.33 ± 0.009 | 0.053 ± 0.01 | 0.015 ± 0.006 | 0.012 ± 0.005 | 0.025 ± 0.005 |
| 0.5 | | 0.11 ± 0.01 | 0.015 ± 0.006 | 0.03 ± 0.007 | 0.0185 ± 0.005 |
| 1 | | | 0.021 ± 0.006 | 0.012 ± 0.007 | 0.014 ± 0.005 |
| 3 | | | 0.03 ± 0.009 | 0.05 ± 0.01 | |
| 5 | | | 0.036 ± 0.013 | | |
| 7 | | | 0.0350.014 | | |

TABLE 29

| | HEMA hydrogels EGDMA = 2% | | | | |
|---|---|---|---|---|---|
| T = 25° | neat | MLV DMPC | | MLV HSPC | |
| Load [Kg] | 0 mM | 2 mM | 18 mM | 2 mM | 18 mM |
| 0.04 | 0.6 ± 0.05 | 0.2 ± 0.03 | 0.03 ± 0.01 | 0.028 ± 0.005 | 0.03 ± 0.008 |
| 0.15 | 0.6 ± 0.05 | 0.5 ± 0.05 | 0.01 ± 0.003 | 0.025 ± 0.005 | 0.025 ± 0.007 |
| 0.5 | | | 0.01 ± 0.003 | 0.03 ± 0.005 | 0.014 ± 0.004 |
| 1 | | | 0.01 ± 0.003 | 0.02 ± 0.005 | 0.01 ± 0.005 |
| 3 | | | 0.01 ± 0.003 | 0.05 ± 0.005 | 0.01 ± 0.005 |
| 5 | | | 0.011 ± 0.0038 | | |
| 7 | | | 0.012 ± 0.005 | | |

TABLE 30

| | HEMA hydrogels EGDMA = 0.1% | | | | |
|---|---|---|---|---|---|
| T = 37° | neat | MLV DMPC | | MLV HSPC | |
| Load | 0 mM | 2 mM | 18 mM | 2 mM | 18 mM |
| 0.04 | 0.27 ± 0.03 | 0.21 ± 0.005 | 0.118 ± 0.01 | 0.023 ± 0.005 | 0.03 ± 0.005 |
| 0.15 | 0.27 ± 0.03 | 0.26 ± 0.005 | 0.2 ± 0.03 | 0.158 ± 0.01 | 0.026 ± 0.005 |
| 0.5 | | | 0.15 ± 0.03 | | 0.03 ± 0.005 |
| 1 | | | | | 0.056 ± 0.005 |

TABLE 31

| | HEMA hydrogels EGDMA = 1% | | | | |
|---|---|---|---|---|---|
| T = 37° | neat | MLV DMPC | | MLV HSPC | |
| Load [Kg] | 0 mM | 2 mM | 18 mM | 2 mM | 18 mM |
| 0.04 | 0.272 ± 0.01 | 0.075 ± 0.008 | 0.07 ± 0.01 | 0.02 ± 0.008 | 0.025 ± 0.005 |
| 0.15 | 0.34 ± 0.01 | 0.055 ± 0.008 | 0.062 ± 0.008 | 0.03 ± 0.008 | 0.015 ± 0.005 |
| 0.5 | | 0.05 ± 0.008 | 0.05 ± 0.01 | 0.074 ± 0.008 | 0.014 ± 0.005 |

TABLE 31-continued

| | | HEMA hydrogels EGDMA = 1% | | | |
|---|---|---|---|---|---|
| T = 37° | neat | MLV DMPC | | MLV HSPC | |
| Load [Kg] | 0 mM | 2 mM | 18 mM | 2 mM | 18 mM |
| 1 | | 0.03 ± 0.008 | 0.04 ± 0.015 | 0.03 ± 0.008 | 0.017 ± 0.005 |
| 3 | | 0.08 ± 0.008 | 0.038 ± 0.013 | | |

TABLE 32

| | | HEMA hydrogels EGDMA = 2% | | | |
|---|---|---|---|---|---|
| T = 37° | neat | MLV DMPC | | MLV HSPC | |
| Load [Kg] | 0 mM | 2 mM | 18 mM | 2 mM | 18 mM |
| 0.04 | 0.6 ± 0.05 | 0.056 ± 0.008 | 0.04 ± 0.01 | 0.056 ± 0.01 | 0.04 ± 0.01 |
| 0.15 | 0.5 ± 0.05 | 0.047 ± 0.008 | 0.03 ± 0.015 | 0.034 ± 0.007 | 0.01 ± 0.005 |
| 0.5 | | 0.1 ± 0.008 | 0.033 ± 0.013 | 0.026 ± 0.006 | 0.0118 ± 0.005 |
| 1 | | 0.077 ± 0.008 | 0.035 ± 0.015 | 0.107 ± 0.02 | 0.014 ± 0.005 |
| 3 | | 0.078 ± 0.008 | 0.035 ± 0.013 | 0.365 ± 0.05 | 0.016 ± 0.005 |

The results of the friction coefficient measurements described hereinabove are summarized in Tables 27-32 below.

HEMA hydrogels with 0.22% and 1% crosslinking, incorporating SUV DMPC liposomes at a concentration ≤2 mM showed relatively high μ values compared with similar hydrogels having liposomes at a concentration of 12 mM. Hydrogels with low concentrations of SUV HSPC (<2 mM) showed relatively low μ values.

HEMA hydrogels with 0.1% and 2% crosslinking incorporating MLV HSPC or MLV DMPC liposomes showed an increase in μ value when liposome concentration was reduced from about 18 mM to about 2 mM and below.

HEMA hydrogels with 1% crosslinking, incorporating MLV liposomes showed an increase in μ values at liposomes concentration between 0.4 to 2 mM, depending on the lipid species and the temperature of the measurement.

Example 15

HEMA-Methacrylic Acid Hydrogels

The effect of adding methacrylic acid (MA or MAAc) to the hydrogel during the HEMA hydrogel/liposome preparation was tested.

Hydrogel Preparation:

Neat hydrogels were prepared as follows: HEMA (1.425 grams), EGDMA at 0.75% (molar percent with respect to the HEMA monomer), methacrylic acid (MA, 75 mg) and APS aqueous solution (2 ml, 53 mM) were vigorously stirred for 30 minutes until fully mixed. TMEDA (50 μl) was added to the mixture, stirred for 20 seconds and poured into a 6 cm diameter petri dish. The gels were allowed to cure over 4-5 hours, followed by rinsing in distilled water for 3 days to remove unreacted materials. The obtained gels were cut into pieces for tribological tests and other characterization methods. Liposome-loaded hydrogels were prepared similarly. The APS aqueous solution was replaced by a liposome suspension with the same APS content.

Hydrogel Water Content:

The water adsorbed by a hydrogel is quantitatively represented by the equilibrium water content (EWC) which is the ratio of the weight of water in the hydrogel to the weight of the hydrogel at equilibrium hydration. The weight of water in the hydrogel is the difference between the weight of the hydrated hydrogel to the dry gel.

The gel in its hydrated form was weighed and then put in an oven until complete dryness of the sample to give its dry weight. EWC of The HEMA-MA neat hydrogel was found to be about 84%, and the EWC of the HEMA-MA hydrogels with liposomes (either MLV DMPC or MLV HSPC) was found to be about 82%.

Dynamic Mechanical Characterization of Hydrogels:

Samples were subjected to a strain sweep test in which they were deformed at different shear strains, and the moduli were recorded to define the linear viscoelastic zone in which the modulus G' is independent of the applied strain. Each sample was then subjected to a frequency sweep test. A sinusoidal deformation of constant peak amplitude was applied over the range of frequencies from 0.05-20 Hz under a stress of 5 Pa at 20° C.

Table 33 presents the results of the frequency sweep at 1 Hz test of a HEMA-MA hydrogels, based on two independent measurements of each hydrogel.

TABLE 33

| | G' [Pa] | G" [Pa] |
|---|---|---|
| neat HEMA-MA | 5300 | 935 |
| HEMA-MA MLV HSPC 30 mM | 9300 | 1330 |
| HEMA-MA MLV HSPC 20 mM | 4100 | 930 |
| HEMA-MA MLV DMPC 30 mM | 3580 | 740 |

Friction Measurements Hydrogel Vs. Metal Head:

Friction forces were measured between the different HEMA-MA hydrogels to a metal head at amplitudes of 1 mm, sliding velocity of 1 mm/sec. Friction coefficient was calculated based on 2-4 measurements from different contact area taken from a 1-2 independent hydrogels preparations.

The results, presented in FIG. 29 and FIG. 30, and the below Tables 34 and 35 respectively, show that the incorporation of MLV HSPC liposomes inside the HEMA-MA hydrogels decrease friction coefficient by a factor of 5, from μ=0.26 for the neat hydrogel down to μ=0.05 for the hydrogel with the 30 mM MLV HSPC. Incorporation of MLV DMPC liposomes at the same concentration did not lower friction coefficient as µ=0.026. The encapsulation of HSPC liposomes not only lowered friction coefficient but also increased the possible working load showing sliding motion between the hydrogel surface to the metal head, from load of less than 40 grams to a load of 500 grams.

Changing the concentration of MLV HSPC liposomes from 30 mM to 20 mM and 10 mM showed a connection between concentration and friction coefficient µ. At concentration of 10 mM MLV HSPC liposomes no shear reduction was observed compared with the neat hydrogel.

FIG. 29 presents a comparative bar-plot, showing the results of the friction coefficient measurements conducted at 25° C. for neat HEMA-MA EGDMA 0.75% and HEMA EGDMA 0.75%+MLV DMPC or HSPC at a liposome concentrations of 10-30 mM.

FIG. 30 presents a comparative bar-plot, showing the results of the friction coefficient measurements conducted at 37° C. for neat HEMA EGDMA 0.75% and HEMA-MA EGDMA 0.75%+MLV HSPC at a liposome concentration of 20 mM.

TABLE 34

| 25° C. | 10 g load | 40 g load | 150 g load | 300 g load | 500 g load |
|---|---|---|---|---|---|
| HEMA-AA neat | 0.26 ± 0.02 | # | | | |
| HEMA-AA MLV HSPC 30 mM | 0.05 ± 0.005 | 0.05 ± 0.005 | 0.05 ± 0.005 | 0.04 ± 0.005 | 0.04 ± 0.005 |
| HEMA-AA MLV HSPC 20 mM | 0.062 ± 0.005 | 0.06 ± 0.005 | 0.063 ± 0.005 | 0.068 ± 0.005 | # |
| HEMA-AA MLV HSPC 10 mM | 0.4 ± 0.02 | # | | | |
| HEMA-AA MLV DMPC 30 mM | 0.26 ± 0.02 | # | | | |

TABLE 35

| 37° C. | 10 g load | 40 g load | 150 g load | 300 g load | 500 g load |
|---|---|---|---|---|---|
| HEMA-AA neat | 0.19 ± 0.02 | # | | | |
| HEMA-AA MLV HSPC 20 mM | 0.04 ± 0.005 | 0.04 ± 0.005 | 0.031 ± 0.005 | 0.025 ± 0.005 | 0.022 ± 0.005 |

Example 16

Methacrylamide/Polyethyleneoxide Dimethacrylate (MAA-PEOdMA) Hydrogels

This study investigated the use of the hydrogel-forming agent methacrylamide (MMA or MAAm) and the crosslinking agent polyethyleneoxide dimethacrylate (also known as poly(ethylene glycol) dimethacrylate, PEOdMA or pEGDMA) in the formation of the hydrogel. In this example, the crosslinking agent was 9EGDMA, or (ethylene glycol)$_9$ dimethacrylate.

Methacrylamide (MMA) and the PEOdMA (ethylene glycol)$_9$ dimethacrylate (9EGDMA) having a MW of 550, were purchased from Sigma-Aldrich and used as received.

Hydrogel Preparation:

Hydrogels with initial methacrylamide concentration of 31% by weight and PEOdMA at a concentration of 7.8 molar % were prepared by photo-initiated radical crosslinking in the presence of the water soluble photoinitiator Irga 2959 0.3% by weight. The hydrogels solutions were stirred till the solution turned clear, and then they were poured to a 6 glass petri dish. The samples were cured by exposure to UV light for 15 minutes. For preparation of hydrogels containing liposomes, pure water was replaced with either MLV DMPC or MLV HSPC of concentration of 39 mM.

Hydrogel Water Content:

Hydrogels in their hydrated form were weighed and then put in an oven until complete dryness of the sample afforded the dry weight. EWC of the MAA-PEOdMA neat hydrogel was found to be 66.6%, and the EWC of the MAA-PEOdMA hydrogels with MLV DMPC or MLV HSPC liposomes was 67.5% and 65%, respectively.

Dynamic Mechanical Characterization of Hydrogels:

Samples were subjected to a strain sweep test in which they were deformed at different shear strains, and the moduli were recorded to define the linear viscoelastic zone in which the modulus G' is independent of the applied strain. Each sample was then subjected to a frequency sweep test. A sinusoidal deformation of constant peak amplitude was applied over the range of frequencies from 0.05-100 Hz under a stress of 20 Pa at 25° C.

Table 36 presents the results of the frequency sweep at 1 Hz test of a MAA hydrogels.

TABLE 36

| | G' [Pa] | G" [Pa] |
|---|---|---|
| MMA-PEOdMA neat | $3.8 \times 10^4$ | $1 \times 10^3$ |
| MMA-PEOsMA MLV HSPC mM | $8.2 \times 10^4$ | $5 \times 10^3$ |
| MMA-PEOsMA MLV DMPC mM | $7.6 \times 10^4$ | $3.2 \times 10^3$ |

Friction Measurements Hydrogel Vs. Metal Head:

Friction forces were measured between the different MAA-PEOdMA hydrogels against a metal head at amplitudes of 1 mm, sliding velocity of 1 mm/sec. Friction coefficient was calculated based on 4 measurements from 2 different contact area taken from a 2 independent hydrogels preparations for the neat and the DMPC incorporated liposomes, and of 2 measurements of different contact points taken from the same hydrogel for the HSPC incorporated liposomes.

At temperature of 25° C. the incorporation of DMPC liposomes into the MAA-PEOdMA hydrogels reduced friction coefficient from µ=0.13 to µ=0.02 or 0.0245, a reduction of a factor of about 5. The incorporation of HSPC liposomes showed a reduction in the friction coefficient of a factor of about 4. Heating the experimental system to temperature of 37° C. showed a reversed trend as the DMPC MAA-PEOdMA hydrogels showed no efficient shear reduction and the HSPC MAA-PEOdMA hydrogels reduced friction coefficient up to a factor of 5.

Table 37 presents the results of the friction coefficient measured at 25° C. between different MAA-PEOdMA hydrogels against a metal head at amplitudes of 1 mm.

TABLE 37

| 25° C. | 40 g load | 150 g load | 500 g load |
|---|---|---|---|
| MAA-PEOdMA neat | 0.13 ± 0.04 | 0.121 ± 0.01 | 0.12 ± 0.005 |
| MAA-PEOdMA MLV DMPC | 0.02 ± 0.007 | 0.020.008 | 0.0245 ± 0.01 |
| MAA-PEOdMA MLV HSPC | 0.03 ± 0.01 | 0.03 ± 0.01 | 0.03 ± 0.01 |

Table 38 presents the results of the friction coefficient measured at 37° C. between different MAA-PEOdMA hydrogels against a metal head at amplitudes of 1 Mm.

TABLE 38

| 37° C. | 40 g load | 150 g load | 500 g load |
|---|---|---|---|
| MAA-PEOdMA neat | 0.069 ± 0.02 | 0.1 ± 0.02 | 0.08 ± 0.01 |
| MAA-PEOdMA MLV DMPC | 0.084 ± 0.03 | 0.093 ± 0.02 | 0.073 ± 0.01 |
| MAA-PEOdMA MLV HSPC | 0.02 ± 0.01 | 0.02 ± 0.01 | 0.019 ± 0.01 |

Example 17

Acrylic Acid/N,N-Dimethacrylamide Hydrogels

The use of acrylamide (AA or AAm) and N,N-dimethacrylamide (nnDMAA) as the hydrogel-forming agents was studied.

Acrylic acid (AA), N,N-dimethacrylamide (nnDMAA), crosslinking agent N,N-methylenebis(acrylamide) (MBA or MBAm), ammonium persulfate (APS), and N,N,N',N'-tetramethylethylenediamine (TMEDA), were purchased from Sigma-Aldrich and used as received.

Hydrogel Preparation:

Neat hydrogels were prepared as follows: AA and nnDMAA were mixed in different molar ratios of 1:1 (G1), 1:2 (G2) and 2:1 (G3) in 0.5% (w/v) of APS and 0.2% (w/v) of MBA. Total monomers concentration was of 20% (v/v). Hydrogel with 40% of monomer concentration (v/v) at 1:1 molar ratio was prepared as well (G4). Hydrogels encapsulating liposomes were prepared by replacing the pure water with liposome suspension of MLV DMPC at 45 mM. All hydrogels were vigorously stirred for 30 minutes until fully mixed. TMEDA (50 µl) was added to the mixture, stirred for 20 seconds and poured into a 6 cm diameter petri dish and the hydrogels were placed on a hot plate of 35° C. for 3-5 minutes. The hydrogels were allowed to cure over 4-5 hours, followed by rinsing in distilled water for 3 days to remove unreacted materials. The obtained hydrogels were cut into pieces for tribological tests and other characterization methods. Liposome-loaded hydrogels were prepared similarly. The APS aqueous solution was replaced by a liposome suspension with the same APS content.

Hydrogels in their hydrated form were weighed and then put in an oven until complete dryness of the sample afforded the dry weight. EWC of The G1, G2 and G3 AA-nnDMAA neat hydrogels was found to be about 98% and G4 AA-nnDMAA neat hydrogel water content was found to be about 92%. For the DMPC incorporated hydrogels, EWC of G1, G2 and G3 was about 98%, and for G4 about 91%.

Dynamic Mechanical Characterization of Hydrogels:

Samples were subjected to a strain sweep test in which they were deformed at different shear strains, and the moduli were recorded to define the linear viscoelastic zone in which the modulus G' is independent of the applied strain. Each sample was then subjected to a frequency sweep test. A sinusoidal deformation of constant peak amplitude was applied over the range of frequencies from 0.05-20 Hz under a stress of 2 Pa at 25° C.

Table 39 presents the result of the frequency sweep at 1 Hz test for the AA-nnDMAA hydrogels.

TABLE 39

| | G' [Pa] | G'' [Pa] |
|---|---|---|
| G1 AA-nnDMAA neat | 423 | 50 |
| G2 AA-nnDMAA neat | 80 | 33 |
| G3 AA-nnDMAA neat | 1066 | 118 |
| G4 AA-nnDMAA neat | 186 | 66 |
| G1 AA-nnDMAA MLV DMPC 45 mM | 625 | 93 |
| G2 AA-nnDMAA MLV DMPC 45 mM | 1728 | 146 |
| G3 AA-nnDMAA MLV DMPC 45 mM | 783 | 70 |
| G4 AA-nnDMAA MLV DMPC 45 mM | 90 | 73 |

Friction Measurements Hydrogel Vs. Metal Head:

Friction forces were measured between the AA-nnDMAA hydrogels against a metal head at amplitudes of 1 mm, sliding velocity of 1 mm/sec. Friction coefficient was calculated based on 2 from different contact area, and the results are presented in Table 40.

TABLE 40

| Results at 37° | 10 g | 40 g |
|---|---|---|
| G1 AA-nnDMAA neat | # | # |
| G2 AA-nnDMAA neat | # | # |
| G3 AA-nnDMAA neat | # | # |
| G4 AA-nnDMAA neat | # | # |
| G1 AA-nnDMAA MLV DMPC | # | # |
| G2 AA-nnDMAA MLV DMPC | 0.0125 ± 0.007 | # |
| G3 AA-nnDMAA MLV DMPC | 0.013 ± 0.007 | # |
| G4 AA-nnDMAA MLV DMPC | 0.012 ± 0.007 | # |

As can be seen in Table 40, the incorporation of MLV DMPC liposomes inside the AA-nnDMAA hydrogels decrease friction coefficient from a rigid coupling for the neat hydrogels G1-G4 to μ=0.012-0.013 for the G2-G4 hydrogel with the 45 mM MLV DMPC. The friction coefficient of the G1 hydrogel did not decrease upon adding liposomes, as the shear trace reveal a rigid coupling scenario. Above a load of 10 g the hydrogel with the incorporated liposomes turn into rigid coupling.

Example 18

Gelatin-Methacrylate Hydrogels

The effect of incorporation of liposomes into gelatin methacrylate hydrogels on the mechanical properties of these hydrogels was tested.

Materials:

Phosphate buffer, sodium hydroxide, methacrylic anhydride and gelatin (type A from porcine skin) and 2-hydroxy-4'-(2-hydroxyethoxy)-2-methylpropiophenone (Irga 2959) were purchased from Sigma Aldrich.

Dialysis was conducted using dialysis membrane (MWCO 12 kDa-14 kDa) from CelluSep membranes.

Synthesis of Methacrylated Gelatin:

Gelatin methacrylate (GM) was synthesized as previously described [Van Den Bulcke, A. I., et al., *Biomacromolecules*, 2000, 1(1), p. 31-38]. Briefly, gelatin (4 grams) was dissolved in phosphate buffer (40 ml, pH 7.4) at 40° C. The pH of the solution was then adjusted to 7.5 using NaOH solution. 2 ml of methacrylic anhydride was added drop wise after gelatin was completely dissolved. During the methacrylation reaction the mixture was stirred and the pH of the solution was kept at the range of 7-7.5 for two hours of reaction time at 50° C. for 30 minutes. Thereafter, the mixture was diluted with PBS and dialyzed for 2 days against distilled water at 40° C. The reaction product was freeze-dried and stored at −20° C. until use.

Liposomes Preparation:

Multilamellar vesicles (MLV) composed of 1,2-dimyristoyl-sn-glycero-3-phosphocholine (DMPC) and hydrogenated soy phosphatidylcholine (HSPC) were prepared by hydrating the lipids in at least 5° C. above the lipid TM, followed by sonication.

Hydrogel Preparation:

Hydrogels with initial gelatin methacrylate concentration of 20% by weight were prepared by photo-initiated radical crosslinking in the presence of the water soluble photoinitiator Irga 2959. The hydrogels solutions were stirred and heated to 40° C. until the solution turned clear, and then poured to a glass petri dish. Hydrogels with liposomes were prepared by replacing water with 45 mM MLV DMPC liposome suspension. The samples were cured by exposure to UV light for 15 minutes.

Rheological Measurements:

Dynamic rheological tests were performed to characterize the visco-elastic properties of the gelatin methacrylate hydrogels. The measurements were carried out using a mars III rheometer, using a parallel plate model.

Friction Measurements:

Round samples of diameter of 21 mm were cut from the GM hydrogels and were glued onto a plastic petri dish. The plastic petri dish was filled with water and the system was heated to 37° C.±0.5° C. Friction force was measured between the GM hydrogels to a metal head of diameter of 28 mm. Friction tests were carried out using a UMT nanobruker tribometer. A normal load of 10 grams was applied, the lateral force (Fs) was measured and the friction coefficient was calculated according to μ=Fs/Fn.

Determination of Degree of Methacrylation:

Samples of 30 mg of GM and unmodified gelatin were dissolved each in 500 μL of deuterium oxide and the level of methacrylation of gelatin was analyzed using $^1$H NMR spectroscopy.

Compared to the unmodified gelatin, new peaks were observed in the NMR spectra of the GM at 5.3 ppm≤δ≤6.2 ppm. These peaks were assigned to the methyl function of the introduced methacrylic groups. The degree of methacrylation was defined as the percentage of the amino acid lysine that was modified. For the quantification of the degree of methacrylation, the NMR spectrum was normalized to the signal of the phenylalanine (6.9-7.5 ppm), which represents the concentration of gelatin. Thereafter, the GM spectra were integrated to obtain the areas A, and the degree of methacrylation (DM) was determined by: DM (%)=(1−A (Lysine methylene of GM)/A(Lysine methylene of unmodified gelatin)). The DM was calculated to be 75% (about 1.3% in terms of degree of crosslinking, or molar percent of a crosslinking agent to hydrogel-forming agent).

Dynamic Mechanical Properties Measurements:

Samples were subjected to a strain sweep test in which they were deformed at different shear strains, and the moduli were recorded to define the linear viscoelastic zone in which the modulus G' is independent of the applied strain. Each sample was then subjected to a frequency sweep test. A sinusoidal deformation of constant peak amplitude was applied over the range of frequencies from 0.05-20 Hz under a stress of 20 Pa at 25° C. and 37° C.

Table 41 presents the results of the friction coefficient measured at 25° C. and 37° C. of the frequency sweep at 1 Hz test of the Gelatin-MA hydrogels.

TABLE 41

|  | G' [Pa]<br>T = 25° C. | G" [Pa]<br>T = 25° C. | G' [Pa]<br>T = 37° C. | G" [Pa]<br>T = 37° C. |
| --- | --- | --- | --- | --- |
| Gelatin-MA neat | 3752 | 97 | 4730 | 451 |
| Gelatin-MA + MLV DMPC | 8000 | 390 | 7600 | 524 |

Hydrogel Water Content:

The equilibrium water content (EWC) of gelatin-methacrylate hydrogels were determined as described hereinabove. EWC of the neat gelatin-MA hydrogels was about 82%, and the EWC of the DMPC gelatin-MA hydrogels was about 86%.

Friction Coefficient Measurements:

Friction forces were measured between the gelatin-MA hydrogels against a metal head at amplitudes of 1 mm in pure water at temperature of 37° C. Friction coefficient was calculated based on 2 measurements from different contact area.

The neat gelatin-MA hydrogels showed that already at normal load of 10 grams after about 2-3 minutes of shearing, the trace was of a rigid coupling, meaning that there was no sliding in the hydrogel-metal interface, and that the two parts were moving together. The probe that monitored the height of the sample showed that under load of 10 grams at T=37° C. after about 130 seconds from the beginning of shearing, there was a dramatic decrease in the height of the sample which is accompanied by the rigid coupling trace.

The gelatin-MA hydrogels with the incorporation of MLV DMPC liposomes show that the friction coefficient at load of 10 grams is of μ=0.056±0.02. The height of the hydrogel sample with the liposomes during the measurement is constant over a running period of one hour, indicating of improved wear as well as reduction of µ.

Shearing the gelatin-MA hydrogel over a range of velocities indicates that the friction coefficient is not a function of the sliding velocity when velocity range from 0.01 mm per second to 5 mm per second. This may implies that the lubrication mechanism of the hydrogel is that of boundary lubrication rather than a hydrodynamic effect, which may be related to the incorporation of the liposomes into the hydrogel.

Example 19

This study investigates the influence of inclusion of cholesterol at varying concentrations into the lipid composition of the liposomes, on the properties of hydrogels encapsulating these liposomes at different measurement temperatures of 25° C. and 37° C.

The exemplary liposomes which were prepared were SUV DPPC, MLV DMPC and MLV HSPC having cholesterol at an amount of 0%, 5%, 10%, 15% and 40% in terms of molar percentage, relative to the total amount of liposome lipids.

Cholesterol-containing MLV DMPC and MLV HSPC liposomes were incorporated into HEMA EGDMA 2% hydrogels for friction coefficient measurements against a metal head.

Cholesterol-containing SUV DPPC liposomes with cholesterol levels of 0%, 5%, 15% and 40% were incorporated into HEMA EGDMA 1% and 2% and were tested as well.

Liposomes concentration inside the hydrogel solution before curing was 18 mM for the MLV liposomes, and 10.5 mM for the SUV liposomes.

Friction Coefficient for HEMA EGDMA2% with MLV of DMPC and HSPC with Cholesterol:

FIG. 31 presents a comparative bar-plot, showing the results of the friction coefficient measurements conducted at 25° C. for HEMA EGDMA 2%+MLV HSPC/Cholesterol, comparing the effect of various cholesterol concentrations of 0%, 10%, 15% and 40%.

Table 42 also presents the friction coefficient measurements shown in FIG. 31.

TABLE 42

HEMA EGDMA 2% + MLV HSPC/Cholesterol, T = 25° C.

| Load [Kg] | 0% cholesterol | 10% cholesterol | 15% cholesterol | 40% cholesterol |
|---|---|---|---|---|
| 0.04 | 0.02 ± 0.005 | 0.02 ± 0.005 | 0.014 ± 0.005 | 0.273 ± 0.01 |
| 0.15 | 0.025 ± 0.007 | 0.015 ± 0.005 | 0.016 ± 0.005 | 0.22 ± 0.008 |
| 0.5 | 0.014 ± 0.005 | 0.02 ± 0.005 | 0.018 ± 0.005 | 0.18 ± 0.01 |
| 1 | 0.01 ± 0.005 | 0.02 ± 0.005 | 0.015 ± 0.005 | 0.06 ± 0.005 |
| 3 | 0.01 ± 0.005 | 0.018 ± 0.005 | 0.035 ± 0.005 | |

As can be seen in FIG. 31 and Table 42, friction coefficient measurements of HEMA hydrogels with MLV HSPC/cholesterol liposomes incorporated inside the hydrogel measured at 25° C. showed that the friction coefficient did not change as the MLV HSPC contained low cholesterol concentrations of 10% and 15%. Increasing the MLV HSPC liposome cholesterol levels inside the HEMA hydrogels to 40% result in an increase of friction coefficient.

FIG. 32 presents a comparative bar-plot, showing the results of the friction coefficient measurements conducted at 25° C. for HEMA EGDMA 2%+MLV DMPC/Cholesterol, comparing the effect of various cholesterol concentrations of 0%, 10%, 15% and 40%.

Table 43 presents the friction coefficient measurements shown in FIG. 32.

TABLE 43

HEMA EGDMA 2% + MLV DMPC/Cholesterol, T = 25° C.

| Load [Kg] | 0% cholesterol | 10% cholesterol | 15% cholesterol | 40% cholesterol |
|---|---|---|---|---|
| 0.04 | 0.01 ± 0.005 | 0.015 ± 0.005 | 0.015 ± 0.005 | 0.027 ± 0.005 |
| 0.15 | 0.01 ± 0.005 | 0.029 ± 0.005 | 0.04 ± 0.005 | 0.02 ± 0.005 |
| 0.5 | 0.01 ± 0.005 | 0.0395 ± 0.005 | 0.066 ± 0.005 | 0.03 ± 0.005 |
| 1 | 0.01 ± 0.005 | 0.03 ± 0.005 | 0.049 ± 0.005 | 0.03 ± 0.005 |
| 3 | 0.01 ± 0.005 | 0.037 ± 0.005 | 0.033 ± 0.005 | 0.028 ± 0.005 |
| 5 | 0.011 ± 0.005 | | | |
| 5 | 0.012 ± 0.005 | | | |

As can be seen in FIG. 32 and Table 43, friction coefficient measurements of HEMA hydrogels with MLV DMPC/Cholesterol liposomes at 25° C. show that already at low cholesterol levels of the MLV DMPC liposomes of 10%, friction coefficient increase, resulting in lowering the maximum applied load/pressure that such hydrogel can sustain before damage occurs.

FIG. 33 presents a comparative bar-plot, showing the results of the friction coefficient measurements conducted at 37° C. for HEMA EGDMA 2%+MLV HSPC/Cholesterol, comparing the effect of various cholesterol concentrations 0%, 10%, 15% and 40%.

Table 44 presents the friction coefficient measurements shown in FIG. 33.

TABLE 44

HEMA EGDMA 2% + MLV HSPC/Cholesterol, T = 37° C.

| Load [Kg] | 0% cholesterol | 10% cholesterol | 15% cholesterol | 40% cholesterol |
|---|---|---|---|---|
| 0.04 | 0.034 ± 0.007 | 0.024 ± 0.005 | 0.045 ± 0.01 | 0.16 ± 0.01 |
| 0.15 | 0.01 ± 0.005 | 0.025 ± 0.005 | 0.05 ± 0.01 | 0.2 ± 0.01 |
| 0.5 | 0.012 ± 0.005 | 0.027 ± 0.005 | 0.052 ± 0.01 | 0.18 ± 0.01 |
| 1 | 0.014 ± 0.005 | 0.015 ± 0.005 | 0.047 ± 0.01 | 0.1 ± 0.01 |
| 3 | 0.016 ± 0.005 | | | |

As can be seen in FIG. 33 and Table 44, heating the experimental setup to 37° C. does not change the effect of friction coefficient for the MLV HSPC/Cholesterol liposomes compared to the similar experiment at 25° C.

FIG. 34 presents a comparative bar-plot, showing the results of the friction coefficient measurements conducted at 37° C. for HEMA EGDMA 2%+MLV DMPC/Cholesterol, comparing the effect of various cholesterol concentrations of 0%, 10%, 15% and 40%.

Table 45 presents the friction coefficient measurements shown in FIG. 34.

TABLE 45

HEMA EGDMA 2% + MLV DMPC/Cholesterol, T = 37° C.

| Load [Kg] | 0% cholesterol | 10% cholesterol | 15% cholesterol | 40% cholesterol |
|---|---|---|---|---|
| 0.04 | 0.02 ± 0.01 | 0.007 ± 0.003 | 0.066 ± 0.01 | 0.9 ± 0.1 |
| 0.15 | 0.02 ± 0.01 | 0.005 ± 0.003 | 0.094 ± 0.01 | 0.66 ± 0.02 |
| 0.5 | 0.025 ± 0.01 | 0.0067 ± 0.003 | 0.0106 ± 0.01 | |
| 1 | 0.035 ± 0.01 | 0.0042 ± 0.003 | 0.083 ± 0.01 | |
| 3 | 0.035 ± 0.01 | 0.0087 ± 0.003 | 0.066 ± 0.01 | |
| 5 | | 0.01 ± 0.005 | 0.06 ± 0.01 | |

As can be seen in FIG. 34 and Table 45, raising the temperature to 37° C. for the hydrogels with the MLV DMPC/cholesterol liposomes revealed that incorporation of 10% of cholesterol inside the MLV DMPC liposome decrease the friction coefficient. Above 10% of cholesterol, namely for the 15% and 40%, an increase in friction coefficient was observed.

Hence, it can be seen that incorporation of cholesterol inside MLV HSPC and measurements at both temperatures of 25° C. and 37° C. had a relatively small effect at low cholesterol concentrations of 10% and 15%, and for higher cholesterol concentration of 40%, the friction coefficient relatively increased. Incorporation of cholesterol inside MLV DMPC and measurements at temperature of 37° C. decreased friction for the low cholesterol concentration of 10% and increased friction coefficient for the higher cholesterol levels.

Friction Coefficient of HEMA EGDMA 1% and 2% with SUV DPPC with Cholesterol:

SUV DPPC liposomes were prepared with different cholesterol concentrations of 0%, 5%, 15% and 40% relative to the total amount of lipid composition of the liposome. Friction coefficients of HEMA hydrogels with 1% and 2% molar percent of EGDMA crosslinking agent, and containing SUV DPPC/cholesterol were measured and calculated using a tribometer.

FIG. 35 presents a comparative bar-plot, showing the results of the friction coefficient measurements conducted at 25° C. for HEMA EGDMA 1%+SUV DPPC containing cholesterol at concentrations of 0%, 5%, 15% and 40%.

FIG. 36 presents a comparative bar-plot, showing the results of the friction coefficient measurements conducted at 25° C. for HEMA EGDMA 2%+SUV DPPC containing cholesterol at concentrations of 0%, 5%, 15% and 40%.

FIG. 37 presents a comparative bar-plot, showing the results of the friction coefficient measurements conducted at 37° C. for HEMA EGDMA 1%+SUV DPPC containing cholesterol at concentrations of 0%, 5%, 15% and 40%.

FIG. 38 presents a comparative bar-plot, showing the results of the friction coefficient measurements conducted at 37° C. for HEMA EGDMA 2%+SUV DPPC containing cholesterol at concentrations of 0%, 5%, 15% and 40%.

Tables 46, 47, 48 and 49 summarize the results presented in FIGS. 35, 36, 37 and 38.

TABLE 46

HEMA EGDMA 1% + SUV DPPC/Cholesterol, T = 25° C.

| Load [Kg] | 0% cholesterol | 5% cholesterol | 15% cholesterol | 40% cholesterol |
|---|---|---|---|---|
| 0.04 | 0.03 ± 0.005 | 0.031 ± 0.007 | 0.28 ± 0.07 | 0.23 ± 0.07 |
| 0.15 | 0.02 ± 0.005 | 0.14 ± 0.008 | 0.32 ± 0.07 | 0.3 ± 0.07 |
| 0.5 | 0.02 ± 0.005 | 0.156 ± 0.008 | | |
| 1 | 0.036 ± 0.005 | | | |

TABLE 47

HEMA EGDMA 2% + SUV DPPC/Cholesterol, T = 25° C.

| CLoad [Kg] | 0% cholesterol | 5% cholesterol | 15% cholesterol | 40% cholesterol |
|---|---|---|---|---|
| 0.04 | 0.04 ± 0.005 | 0.01 ± 0.005 | 0.2 ± 0.01 | 0.24 ± 0.03 |
| 0.15 | 0.025 ± 0.005 | 0.009 ± 0.005 | 0.21 ± 0.01 | 0.19 ± 0.01 |
| 0.5 | 0.018 ± 0.005 | 0.008 ± 0.005 | 0.16 ± 0.01 | 0.16 ± 0.01 |
| 1 | 0.018 ± 0.005 | 0.016 ± 0.005 | 0.135 ± 0.005 | 0.11 ± 0.01 |

TABLE 48

HEMA EGDMA 1% + SUV DPPC/Cholesterol, T = 37° C.

| Load [Kg] | 0% cholesterol | 5% cholesterol | 15% cholesterol | 40% cholesterol |
|---|---|---|---|---|
| 0.04 | 0.009 ± 0.005 | 0.009 ± 0.005 | 0.017 ± 0.005 | 0.013 ± 0.005 |
| 0.15 | 0.013 ± 0.005 | 0.011 ± 0.005 | 0.018 ± 0.005 | 0.08 ± 0.01 |
| 0.5 | 0.015 ± 0.005 | 0.01 ± 0.005 | 0.011 ± 0.005 | |
| 1 | 0.035 ± 0.005 | 0.016 ± 0.005 | 0.027 ± 0.007 | |
| 3 | | 0.018 ± 0.005 | 0.036 ± 0.008 | |

TABLE 49

HEMA EGDMA 2% + SUV DPPC/Cholesterol, T = 37° C.

| Load [Kg] | 0% cholesterol | 5% cholesterol | 15% cholesterol | 40% cholesterol |
|---|---|---|---|---|
| 0.04 | 0.039 ± 0.008 | 0.013 ± 0.005 | 0.07 ± 0.01 | 0.31 ± 0.01 |
| 0.15 | 0.068 ± 0.008 | 0.03 ± 0.005 | 0.11 ± 0.01 | 0.27 ± 0.01 |
| 0.5 | 0.064 ± 0.008 | 0.047 ± 0.005 | 0.11 ± 0.01 | 0.21 ± 0.01 |
| 1 | 0.034 ± 0.008 | 0.1 ± 0.005 | 0.14 ± 0.01 | 0.17 ± 0.01 |

As can be seen in FIGS. 35, 36, 37 and 38 and in Tables 46, 47, 48 and 49, hydrogels having a 1% crosslinking agent showed that addition of cholesterol results in an increase of the friction coefficient, while the hydrogels with a higher percentage of crosslinking agent showed a decrease in the friction coefficient upon adding low levels of cholesterol (as low as 5%), and increasing cholesterol levels to 10% and 15% increased the friction coefficient. Heating the hydrogels to 37° C. for the 1% of crosslinking hydrogels having low levels of cholesterol resulted in a decrease of the friction coefficient under high loads. Hydrogels having 2% crosslinking that were measured at 37° C. showed that at low loads, adding 5% cholesterol reduced the friction coefficient while at the higher loads, adding cholesterol increased the friction coefficient.

In general, it can be summarized that that the effect of the addition of low levels (5-10%) of cholesterol to liposomes encapsulated in a hydrogel, is a decrease in the observed friction coefficient $\mu$ compared to corresponding hydrogels containing high levels (40%) of cholesterol, for which $\mu$ is increased, depending on the lipid specie and the temperature.

Specifically, adding cholesterol into MLV HSPC liposomes that were incorporated in HEMA EGDMA 2% hydrogels at low levels (10% and 15% at T=25° C. and 10% for T=37° C., did not affect friction coefficient $\mu$. Higher levels of cholesterol than the above result in an increase of $\mu$.

Adding 10%, 15% and 40% cholesterol into MLV HSPC liposomes that were incorporated in HEMA EGDMA 2% hydrogels, resulted in an increasing $\mu$ at T=25° C. At T=37° C. adding 10% (low level) of cholesterol resulted in a decrease of $\mu$, and increasing cholesterol levels to 15% and 40% result in an increasing $\mu$.

Adding cholesterol into SUV DPPC liposomes that were incorporated into HEMA hydrogels with 1% or 2% of crosslinking agent showed that for the 1% crosslinking level adding cholesterol increased $\mu$ at T=25° C. At T=37° C. adding low level of cholesterol (5% and 15%) did not have a notable effect on $\mu$, while at higher levels of cholesterol (40%) $\mu$ increased. For the 2% crosslinking level, adding 15% and 40% cholesterol increased $\mu$, while adding 5% cholesterol to the liposomes decreases $\mu$ at the low loads region and at T=37° C. and at the high loads region for T=25° C.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising a hydrogel or a composite material containing a hydrogel, and a plurality of liposomes dispersed throughout the bulk of said hydrogel, the composition being characterized by a shear storage modulus (G') of at least 1000 Pa at a temperature of 25° C. and a frequency of 1 Hz,
    wherein:
    an average diameter of said liposomes is larger than 80 nm; and/or
    a degree of crosslinking of said hydrogel is higher than 0.2 molar percent, wherein said crosslinking comprises covalent crosslinking.

2. The composition or composite of claim 1, wherein a concentration of said liposomes is higher than 4 mM.

3. The composition or composite of claim 1, wherein an average diameter of said liposomes is larger than 80 nm.

4. The composition or composite of claim 3, wherein a degree of covalent crosslinking of said hydrogel is higher than 0.2 molar percent.

5. The composition or composite of claim 3, wherein a degree of covalent crosslinking of said hydrogel is 0.2 molar percent or lower.

6. The composition or composite of claim 1, wherein a degree of covalent crosslinking of said hydrogel is higher than 0.2 molar percent and an average diameter of said liposomes is 80 nm or lower.

7. The composition or composite of claim 1, wherein said liposomes further comprise an additional agent selected from the group consisting of a polymer, a hydrogel-forming polymer, cholesterol, a liposome-stabilizing agent, a labeling agent, a bioactive agent and a therapeutically active agent.

8. The composition or composite of claim 7, wherein a concentration of said cholesterol ranges from 1 molar percent to 50 molar percent relative to a total lipid amount of said liposome.

9. The composition or composite of claim 1, wherein said hydrogel comprises a hydrogel-forming agent being selected from the group consisting of hydroxyethyl methacrylate (HEMA), hydroxyethyl acrylate (HEA), acrylamide (AAm), methacrylamide (MAAm), acrylic acid (AAc), methacrylic acid (MAAc), hydroxyethyl acrylate (HEA), hexyl methacrylate, N-isopropylacrylamide (NiPAAm)), N-isopropylmethacrylamide, polylactic acid, polyamide, polyethylene-terephthalate (PET), polyvinyl alcohol, polyurethane, polycaprolactone, polyethylene-glycol (PEG), polyethyl-eneoxide dimethacrylate (PEOdMA), N,N-dimethacrylamide (nnDMAA), hyaluronic acid (HA), HA methacrylate, peptides, saccharides, gelatin, gelatin methacrylate, chitosan, chitosan methacrylate, glycol chitosan, glycol chitosan methacrylate, alginate, alginate methacrylate, cellulose, siloxanes, polysiloxanes, and any oligomer and/or polymer thereof, in any combination thereof.

10. The composition or composite of claim 9, wherein said hydrogel-forming agent is gelatin methacrylate, and wherein a degree of methacrylation in said gelatin methacrylate ranges from 10 percents to 90 percents.

11. The composition or composite of claim 1, being in a dry form.

12. The composition or composite of claim 1, wherein said liposomes are selected from the group consisting of small unilamellar vesicles (SUV), large unilamellar vesicles (LUV) and multilamellar vesicles (MLV).

13. The composition or composite of claim 1, wherein said liposomes comprise at least one phosphatidylcholine phospholipid.

14. The composition or composite of claim 1, wherein said composite material comprises a material selected from the group consisting of a woven mesh of fibers, non-woven fibers, a plurality of rods and a net.

15. The composition or composite of claim 1, being characterized by a dynamic friction coefficient in aqueous medium that ranges from 0.001 to 0.08 under a pressure of at least 1 atmosphere.

16. The composition or composite of claim 15, wherein said friction coefficient is substantially maintained at room temperature and/or at 37° C. over a period of at least 60 minutes under essentially constant load and temperature.

17. The composition or composite of claim 15, wherein said friction coefficient is substantially maintained at room temperature and/or at 37° C. after at least one dehydration-rehydration cycle.

18. A process for preparing the composition or composite of claim 1, the process comprising:
    mixing an aqueous suspension of said liposomes with a hydrogel-forming agent in the presence of a covalent crosslinking agent,
    thereby obtaining the composition.

19. The process of claim 18, wherein said suspension further comprises an initiator.

20. The process of claim 18, wherein said suspension further comprises a catalyst.

21. The process of claim 18, further comprising dehydrating the composition.

22. The process of claim 21, further comprising, subsequent to said dehydrating, rehydrating the composition.

23. The process of claim 18, wherein said hydrogel-forming agent is selected from the group consisting of hydroxyethyl methacrylate (HEMA), hydroxyethyl acrylate (HEA), acrylamide (AAm), methacrylamide (MAAm), acrylic acid (AAc), methacrylic acid (MAAc), hydroxyethyl acrylate (HEA), hexyl methacrylate, N-isopropylacrylamide (NiPAAm), N-isopropylmethacrylamide, polylactic acid, polyamide, polyethylene-terephthalate (PET), polyvinyl alcohol, polyurethane, polycaprolactone, polyethylene-glycol (PEG), polyethyleneoxide dimethacrylate (PEOdMA), N,N-dimethacrylamide (nnDMAA), hyaluronic acid (HA), HA methacrylate, gelatin, gelatin methacrylate, chitosan, chitosan methacrylate, glycol chitosan, glycol chitosan methacrylate, alginate, alginate methacrylate, cellulose, a siloxane, a polysiloxane, and any combination thereof.

24. The process of claim 18, wherein said covalent crosslinking agent is selected from the group consisting of poly(ethylene glycol)$_n$ dimethacrylate (EGDMA), N,N'-methylenebis(acrylamide) (MBAm), N,N'-methylenebis(2- methylacrylamide), methylene diacrylate, methylene bis(2-methylacrylate), diethylene glycol diacrylate, hexamethylene diacrylate, oxybis(methylene) bis(2-methylacrylate) and oxybis(ethane-2,1-diyl) bis(2-methylacrylate).

25. A composition or composite prepared by the process of claim 18.

26. An article-of-manufacturing comprising the composition or composite of claim 1.

27. The article-of-manufacturing of claim 26, selected from the group consisting of an implantable medical device, a drug-delivery system, a solid body, a disc, a fiber, a fabric, a tube, a film, a rod, a ring, a tubular mesh and any combination thereof.

28. A method of treating a living organism suffering from a medical condition associated with loss of or damaged cartilage, comprising replacing at least a portion of said cartilage with the composition or composite of claim 1.

29. The method of claim 28, wherein said medical condition is selected from the group consisting of a skeletal joint replacement or reconstruction, vertebrate replacement or reconstruction, tendon replacement, tissue regeneration and reduction of tissue irritation by an implantable device.

* * * * *